US009574000B2

(12) United States Patent
Langermann et al.

(10) Patent No.: US 9,574,000 B2
(45) Date of Patent: Feb. 21, 2017

(54) ANTI-HUMAN B7-H4 ANTIBODIES AND THEIR USES

(71) Applicants: MEDIMMUNE, LLC, Gaithersburg, MD (US); The Johns Hopkins University, Baltimore, MD (US)

(72) Inventors: Solomon Langermann, Baltimore, MD (US); Linda Liu, Clarksville, MD (US); Sheng Yao, Columbia, MD (US); Lieping Chen, Hamden, CT (US); Michael Glen Overstreet, Crownsville, MD (US)

(73) Assignees: MedImmune, LLC, Gaithersburg, MD (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/654,074

(22) PCT Filed: Dec. 19, 2013

(86) PCT No.: PCT/US2013/076701
§ 371 (c)(1),
(2) Date: Jun. 19, 2015

(87) PCT Pub. No.: WO2014/100483
PCT Pub. Date: Jun. 26, 2014

(65) Prior Publication Data
US 2015/0315275 A1 Nov. 5, 2015

Related U.S. Application Data

(60) Provisional application No. 61/739,272, filed on Dec. 19, 2012, provisional application No. 61/739,353, filed on Dec. 19, 2012, provisional application No. 61/739,287, filed on Dec. 19, 2012.

(51) Int. Cl.
| | |
|---|---|
| *C07K 16/18* | (2006.01) |
| *C07K 16/28* | (2006.01) |
| *A61K 39/395* | (2006.01) |
| *C07K 16/30* | (2006.01) |
| *G01N 33/574* | (2006.01) |
| *A61K 39/00* | (2006.01) |

(52) U.S. Cl.
CPC ........... *C07K 16/2827* (2013.01); *C07K 16/30* (2013.01); *C07K 16/3069* (2013.01); *G01N 33/574* (2013.01); *A61K 2039/505* (2013.01); *C07K 2317/24* (2013.01); *C07K 2317/30* (2013.01); *C07K 2317/31* (2013.01); *C07K 2317/34* (2013.01); *C07K 2317/56* (2013.01); *C07K 2317/73* (2013.01); *C07K 2317/732* (2013.01); *C07K 2317/76* (2013.01); *C07K 2317/77* (2013.01); *C07K 2317/92* (2013.01)

(58) Field of Classification Search
CPC ..... C07K 16/28; C07K 16/2827; C07K 16/46; C07K 16/461; C07K 16/464; A61K 39/395; A61K 39/39533; A61K 39/39541
See application file for complete search history.

(56) References Cited

U.S. PATENT DOCUMENTS

| | | | |
|---|---|---|---|
| 7,931,896 | B2 | 4/2011 | Chen |
| 7,964,195 | B2 | 6/2011 | Papkoff et al. |
| 2008/0160036 | A1 | 7/2008 | Chen et al. |
| 2009/0011444 | A1 | 1/2009 | Chen et al. |

FOREIGN PATENT DOCUMENTS

| | | |
|---|---|---|
| WO | 2004/101756 | 11/2004 |
| WO | 2011016238 A1 | 2/2011 |
| WO | 2012145493 A1 | 10/2012 |

OTHER PUBLICATIONS

Patent Examination Report No. 1, issued in corresponding Australian Patent Application No. 2013361275, dated Nov. 19, 2015 (3 pages).
Sica, G.L. et al., 2003, "B7-H4, a Molecule of the B7 Family, Negatively Regulates T Cell Immunity", Immunity, vol. 18, Issue 6, pp. 849-861.

*Primary Examiner* — Misook Yu
*Assistant Examiner* — Anne Holleran
(74) *Attorney, Agent, or Firm* — Melissa Hunter-Ensor; Elbert Chiang; Greenberg Traurig, LLP

(57) ABSTRACT

Anti-human B7-H4 antibody "6H3", antigen-binding fragments, derivatives, and humanized variants thereof that are capable of immunospecifically binding to B7-H4, and the uses of such molecules in the diagnosis and the treatment of cancer and other diseases are disclosed. In preferred embodiments, the molecules are used to retard or prevent tumor growth, inhibit tumor-mediated suppression, eliminate tumors and/or deplete or block the activity of tumor-associated macrophages ("TAMs") so as to alter their activity and/or decrease TAM-mediated immune suppression.

15 Claims, 30 Drawing Sheets

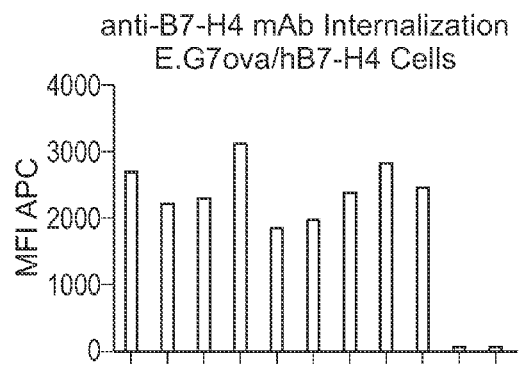
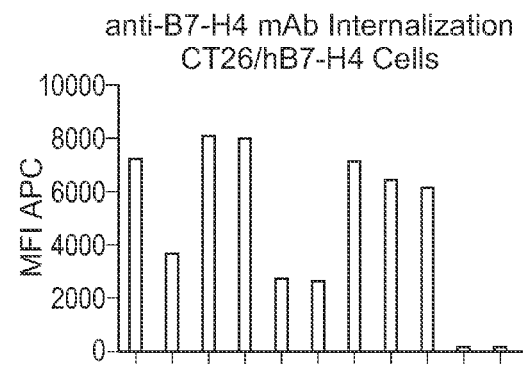
FIG. 18A    FIG. 18B
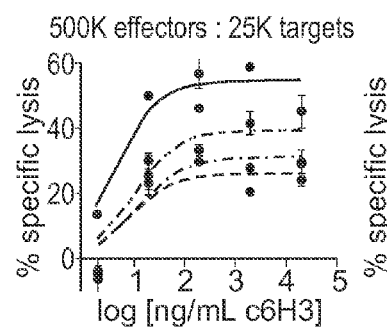
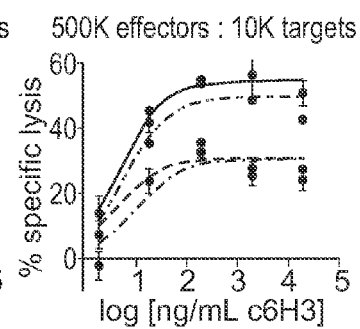
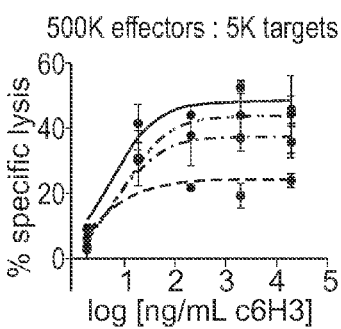
FIG. 19A    FIG. 19B    FIG. 19C
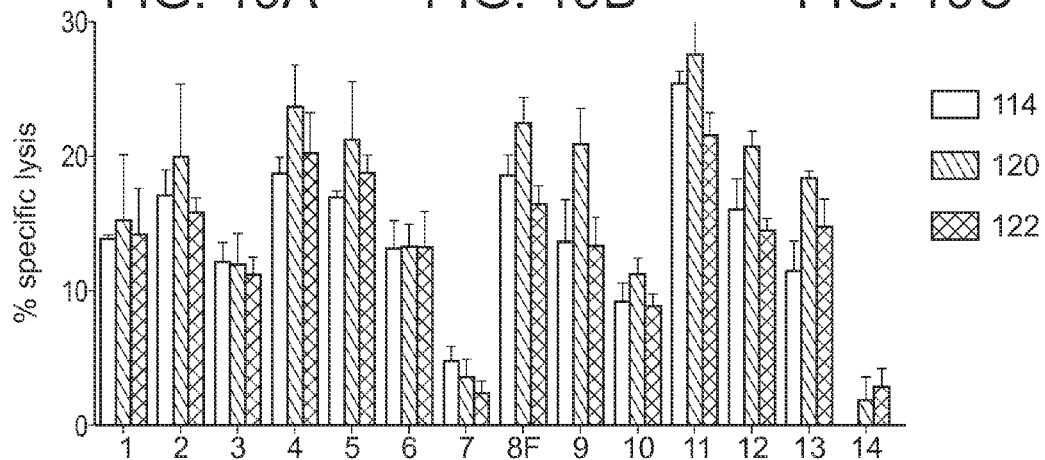
FIG. 20

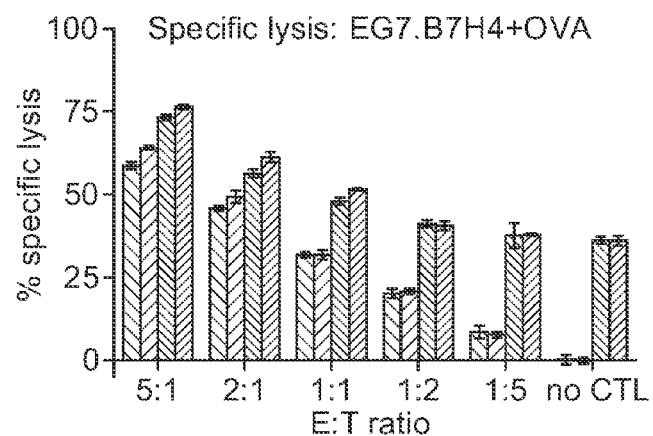
FIG. 26
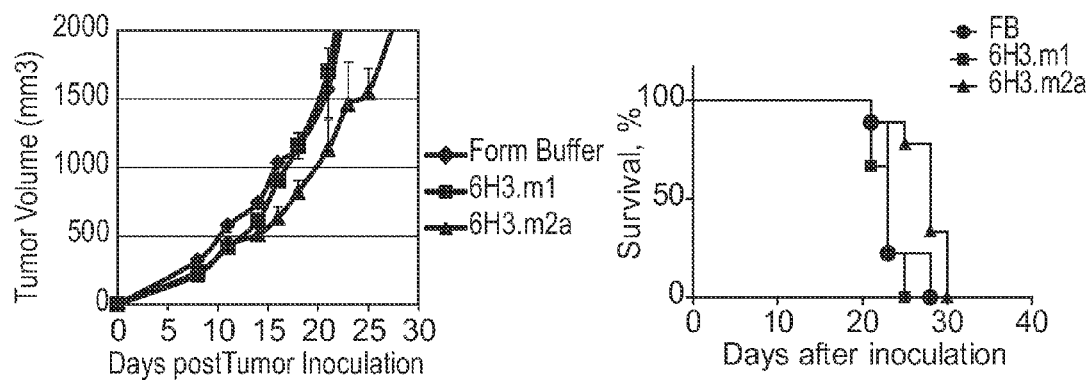
FIG. 27A
FIG. 27B
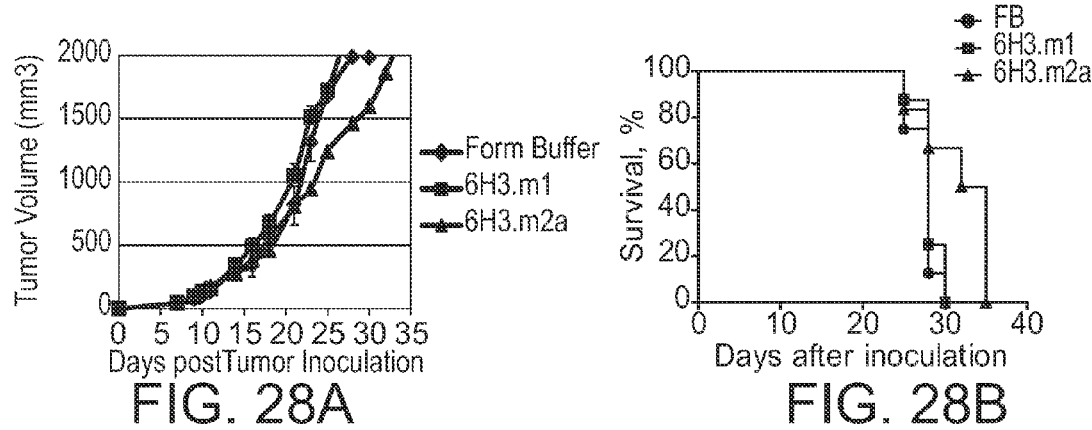
FIG. 28A
FIG. 28B

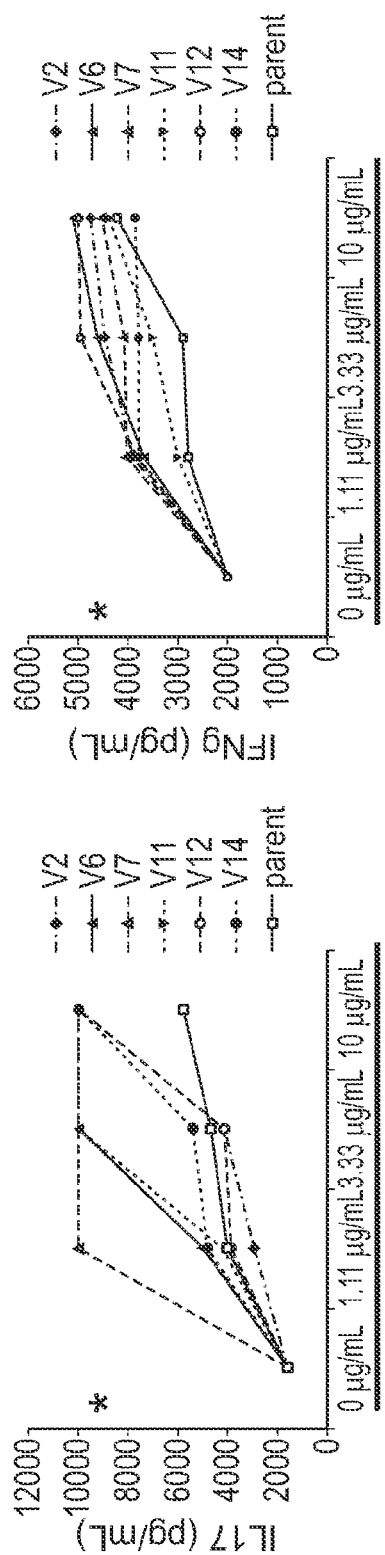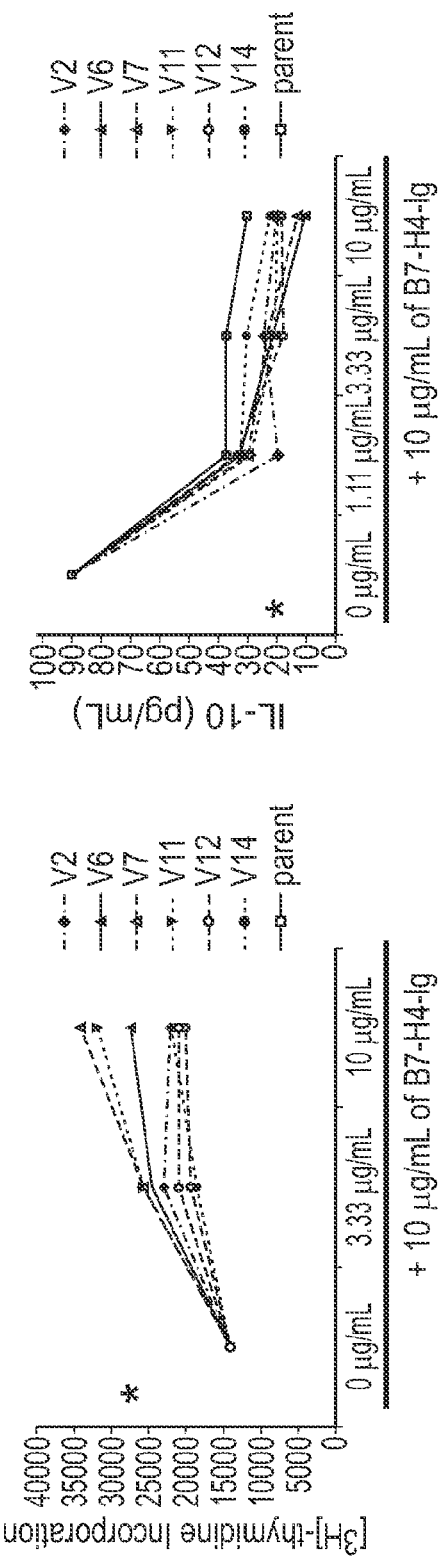

ANTI-HUMAN B7-H4 ANTIBODIES AND THEIR USES

CROSS-REFERENCE TO RELATED APPLICATIONS

This application is a 371 application of International Application No. PCT/US2013/076701, filed Dec. 19, 2013, which claims the benefit of and priority to U.S. Ser. No. 61/739,272 filed Dec. 19, 2012, U.S. Ser. No. 61/739,287 filed Dec. 19, 2012, and U.S. Ser. No. 61/739,353 filed Dec. 19, 2012, each of which is incorporated by reference in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

FIELD OF THE INVENTION

The present invention relates to anti-B7-H4 binding molecules including murine anti-human B7-H4 antibody "6H3" and chimeric and humanized variants thereof, and their antigen-binding fragments and to derivatives thereof that are capable of immunospecifically binding to B7-H4 and the uses of such molecules in the diagnosis and the treatment of cancer and other diseases. The invention particularly concerns the use of such molecules to retard or prevent tumor growth, inhibit tumor-mediated suppression, eliminate tumors and/or deplete or block the activity of tumor-associated macrophages ("TAMs") so as to alter their activity and/or decrease TAM-mediated immune suppression.

BACKGROUND OF THE INVENTION

A. Cell Mediated Immune Responses

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, natural killer cells (NK), and antigen-specific cytotoxic T-lymphocytes by T cells, and the release of various cytokines in response to the recognition of an antigen (Dong, C. et al. (2003) "*Immune Regulation by Novel Costimulatory Molecules,*" Immunolog. Res. 28(1): 39-48).

The ability of T cells to optimally mediate an immune response against an antigen requires two distinct signaling interactions (Viglietta, V. et al. (2007) "*Modulating Co-Stimulation,*" Neurotherapeutics 4:666-675; Korman, A. J. et al. (2007) "*Checkpoint Blockade in Cancer Immunotherapy,*" Adv. Immunol. 90:297-339). First, antigen that has been arrayed on the surface of antigen-presenting cells (APC) must be presented to an antigen-specific naive CD4+ T cell. Such presentation delivers a signal via the T cell receptor (TCR) that directs the T cell to initiate an immune response that will be specific to the presented antigen. Second, a series of co-stimulatory signals, mediated through interactions between the APC and distinct T cell surface molecules, triggers first the activation and proliferation of the T cells and ultimately their inhibition. Thus, the first signal confers specificity to the immune response whereas the second signal serves to determine the nature, magnitude and duration of the response.

The immune system is tightly controlled by co-stimulatory ligands and receptors. These molecules provide the second signal for T cell activation and provide a balanced network of positive and negative signals to maximize immune responses against infection while limiting immunity to self (Wang, L. et al. (Mar. 7, 2011) "*VISTA, A Novel Mouse Ig Superfamily Ligand That Negatively Regulates T Cell Responses,*" J. Exp. Med. 10.1084/jem.20100619:1-16; Lepenies, B. et al. (2008) "*The Role Of Negative Costimulators During Parasitic Infections,*" Endocrine, Metabolic & Immune Disorders—Drug Targets 8:279-288). Of particular importance is binding between the B7.1 (CD80) and B7.2 (CD86) ligands of the APC and the CD28 and CTLA-4 receptors of T-lymphocytes (Sharpe, A. H. et al. (2002) "*The B7-CD28 Superfamily,*" Nature Rev. Immunol. 2:116-126; Dong, C. et al. (2003) "*Immune Regulation by Novel Costimulatory Molecules,*" Immunolog. Res. 28(1):39-48; Lindley, P. S. et al. (2009) "*The Clinical Utility Of Inhibiting CD28-Mediated Costimulation,*" Immunol Rev. 229:307-321). Binding of B7.1 or of B7.2 to CD28 stimulates T cell activation; binding of B7.1 or B7.2 to CTLA4 inhibits such activation (Dong, C. et al. (2003) "*Immune Regulation by Novel Costimulatory Molecules,*" Immunolog. Res. 28(1): 39-48; Lindley, P. S. et al. (2009) "*The Clinical Utility Of Inhibiting CD28-Mediated Costimulation,*" Immunol. Rev. 229:307-321; Greenwald, R. J. et al. (2005) "*The B7 Family Revisited,*" Ann. Rev. Immunol. 23:515-548). CD28 is constitutively expressed on the surface of T cells (Gross, J., et al. (1992) "*Identification And Distribution Of The Costimulatory Receptor CD28 In The Mouse,*" J. Immunol. 149: 380-388), whereas CTLA4 expression is rapidly up-regulated following T-cell activation (Linsley, P. et al. (1996) "*Intracellular Trafficking Of CTLA4 And Focal Localization Towards Sites Of TCR Engagement,*" Immunity 4:535-543). Since CTLA4 is the higher affinity receptor (Sharpe, A. H. et al. (2002) "*The B7-CD28 Superfamily,*" Nature Rev. Immunol. 2:116-126), binding first initiates T cell proliferation (via CD28) and then inhibits it (via nascent expression of CTLA4), thereby dampening the effect when proliferation is no longer needed.

Further investigations into the ligands of the CD28 receptor have led to the identification and characterization of a set of related B7 molecules (the "B7 Superfamily") (Coyle, A. J. et al. (2001) "*The Expanding B7 Superfamily: Increasing Complexity In Costimulatory Signals Regulating T Cell Function,*" Nature Immunol. 2(3):203-209; Sharpe, A. H. et al. (2002) "*The B7-CD28 Superfamily,*" Nature Rev. Immunol. 2:116-126; Greenwald, R. J. et al. (2005) "*The B7 Family Revisited,*" Ann. Rev. Immunol. 23:515-548; Collins, M. et al. (2005) "*The B7 Family Of Immune-Regulatory Ligands,*" Genome Biol. 6:223.1-223.7; Loke, P. et al. (2004) "*Emerging Mechanisms Of Immune Regulation: The Extended B7 Family And Regulatory T Cells.*" Arthritis Res. Ther. 6:208-214; Korman, A. J. et al. (2007) "*Checkpoint Blockade in Cancer Immunotherapy,*" Adv. Immunol. 90:297-339; Flies, D. B. et al. (2007) "*The New B7s: Playing a Pivotal Role in Tumor Immunity,*" J. Immunother. 30(3): 251-260; Agarwal, A. et al. (2008) "*The Role Of Positive Costimulatory Molecules In Transplantation And Tolerance,*" Curr. Opin. Organ Transplant. 13:366-372; Lenschow, D. J. et al. (1996) "*CD28/B7 System of T Cell Costimulation,*" Ann. Rev. Immunol. 14:233-258; Wang, S.

et al. (2004) "*Co-Signaling Molecules Of The B7-CD28 Family In Positive And Negative Regulation Of T Lymphocyte Responses,*" Microbes Infect. 6:759-766). There are at least eight members of the family: B7.1 (CD80), B7.2 (CD86), the inducible co-stimulator ligand (ICOS-L; B7-H2), the programmed cell death-1 ligand 1 (PD-L1; B7-H1), the programmed cell death-1 ligand 2 (PD-L2; B7-DC), B7-H3 (B7-RP2), B7-H4 (also referred to as B7x and B7S1; Sica, G. L. et al. (2003) "*B7-H4, A Molecule Of The B7 Family, Negatively Regulates T Cell Immunity,*" Immunity 18:849-861; Zang, X. et al. (2003) *B7x: A Widely Expressed B7 Family Member That Inhibits T Cell Activation,*" Proc. Natl. Acad. Sci. (USA) 100:10388-10392; Prasad, D. V. et al. (2003) *B7S1, A Novel B7 Family Member That Negatively Regulates T Cell Activation,*" Immunity 18:863-873) and B7-H6 (Brandt, C. S. et al. (2009) "*The B7 family member B7-H6 is a tumor cell ligand for the activating natural killer cell receptor NKp30 in humans*", J Exp Med. 206(7):1495-503).

Soluble forms of B7-CD28 family molecules are also implicated in the progression of rheumatoid diseases. Studies have shown that soluble PD-1 could be detected in rheumatoid arthritis (RA) patients and that the levels of soluble PD-1 correlated with TNF-α concentration in synovial fluid. Soluble B7-H4 (sH4) has been detected in ovarian cancer patients as a potential biomarker, and results from a study of 68 patients with RA and 24 healthy volunteers indicated that soluble B7-H4 was present in blood of 65% of patients with RA, compared with only 13% of healthy people (Simon, I. et al. (2006) "*B7-H4 Is A Novel Membrane-Bound Protein And A Candidate Serum And Tissue Biomarker For Ovarian Cancer,*" Cancer Res. 66(3): 1570-1575, Azuma, T. et al. (2009) "*Potential Role Of Decoy B7-H4 In The Pathogenesis Of Rheumatoid Arthritis: A Mouse Model Informed By Clinical Data,*" PLoS Med., 6(10):e1000166). The levels of soluble B7-H4 were significantly higher in RA patients (96.1 ng/ml) relative to healthy people (<5 ng/ml).

In vivo studies in a murine model indicate that both overexpression of sH4 and deletion of B7-H4 caused inflammation (Azuma, T. et al. (2009) "*Potential Role Of Decoy B7-H4 In The Pathogenesis Of Rheumatoid Arthritis: A Mouse Model Informed By Clinical Data,*" PLoS Med. 6(10):e1000166). Symptoms in the mice appeared earlier and were more severe than controls, and inflammatory effects of soluble B7-H4 were shown to be dependent on neutrophils. Using a protein that mimics the normal signaling by B7-H4, disease development was prevented in the mice.

B. B7-H4 cDNA encoding the human B7-H4 protein was identified and cloned from placental cDNA (Sica, G. L. et al. (2003) "*B7-H4, A Molecule Of The B7 Family, Negatively Regulates T Cell Immunity,*" Immunity 18:849-861; Zang, X. et al. (2003) *B7x: A Widely Expressed B7 Family Member That Inhibits T Cell Activation,*" Proc. Natl. Acad. Sci. (USA) 100:10388-10392). B7-H4 is discussed in U.S. Pat. Nos. 7,931,896; 7,875,702; 7,847,081; 7,622,565; in United States Patent Publications No. 2011/0085970; 2011/0020325; 2010/0256000; 2010/0240585; 2010/0227343; 2010/0227335; 2010/0158936; 2010/0092524; 2010/0028450; 2009/0275633; 2009/0215084; 2009/0176317; 2009/0142342; 2009/0118175; 2009/0087416; 2009/0048122; 2009/0022747; 2009/0018315; 2008/0206235; 2008/0160036; 2008/0177039; 2008/0050370; 2007/0218032; 2007/0184473; 2007/0172504; 2007/0160578; 2007/0122378; 2007/0036783; 2006/0003452; in European Patent Publications Nos. EP 2124998 and EP 2109455; and in PCT Patent Publications WO 2011/026132A2; WO 2011/026122A2; WO 2011/005566A2; WO 2010/144295A1; WO 2010/102177A1; WO 2010/102167A1; WO 2009/111315A2; WO 2009/073533A2; WO 2008/092153A2; WO 2008/083239A2; WO 2008/083228A2; WO 2007/124361A2; WO 2007/122369A2; WO 2007/109254A2; WO 2007/087341A2; WO 2007/082154A2; WO 2007/067682A2; WO 2007/067681A2; WO 2007/041694A2; WO 2006/138670A2; WO 2006/133396A2; WO 2006/121991A2; WO 2006/066229A2; and WO 2006/007539A1.

Anti-B7-H4 antibodies are disclosed in U.S. Pat. Nos. 7,888,477; 7,737,255; 7,619,068; 6,962,980, and in United States Patent Publication No. 20080199461. WO/2013/025779 is of particular relevance.

Human B7-H4 protein possesses 282 amino acid residues, which have been categorized as including an amino terminal extracellular domain, a large hydrophobic transmembrane domain and a very short intracellular domain (consisting of only 2 amino acid residues). Like other B7 family members, B7-H4 possesses a pair of Ig-like regions in its extracellular domain. The B7-H4 protein has an overall structure of a type I transmembrane protein. The protein has minimal (about 25%) homology with other B7 family members (Zang, X. et al. (2003) *B7x: A Widely Expressed B7 Family Member That Inhibits T Cell Activation,*" Proc. Natl. Acad. Sci. (USA) 100:10388-10392).

The human B7-H4 cDNA sequence has been used to identify a murine B7-H4 homolog. The level of identity between the murine and human orthologs (approximately 87%) suggests that B7-H4 is highly conserved evolutionarily (Sica, G. L. et al. (2003) "*B7-H4, A Molecule Of The B7 Family, Negatively Regulates T Cell Immunity,*" Immunity 18:849-861; Zang, X. et al. (2003) *B7x: A Widely Expressed B7 Family Member That Inhibits T Cell Activation,*" Proc. Natl. Acad. Sci. (USA) 100:10388-10392). The extensive homology increases to 91% for the IgV domains of the proteins, which are believed to be involved in binding the B7-H4 receptor (Stamper, C. C. et al. (2001) "*Crystal Structure Of The B7-1/CTLA-4 Complex That Inhibits Human Immune Responses,*" Nature 410: 608-611; Schwartz, J. C. et al. (2001) "*Structural Basis For Co-Stimulation By The Human CTLA-4/B7-2 Complex,*" Nature 410:604-608).

In contrast to other B7 members, B7-H4 mRNA is widely expressed. Its expression has been found in the brain, heart, kidney, liver, lung, ovary, pancreas, placenta, prostate, skeletal muscle, skin, small intestine, spleen, stomach, testis, thymus, thymus, and uterus (Sica, G. L. et al. (2003) "*B7-H4, A Molecule Of The B7 Family, Negatively Regulates T Cell Immunity,*" Immunity 18:849-861; Zang, X. et al. (2003) *B7x: A Widely Expressed B7 Family Member That Inhibits T Cell Activation,*" Proc. Natl. Acad. Sci. (USA) 100:10388-10392; Prasad, D. V. et al. (2003) *B7S1, A Novel B7 Family Member That Negatively Regulates T Cell Activation,*" Immunity 18:863-873; Prasad, D. V. et al. (2003) *B7S1, A Novel B7 Family Member That Negatively Regulates T Cell Activation,*" Immunity 18:863-873).

Despite the widespread expression of B7-H4 mRNA, the presence of B7-H4 protein on the surface of normal cells seems to be limited (Sica, G. L. et al. (2003) "*B7-H4, A Molecule Of The B7 Family, Negatively Regulates T Cell Immunity,*" Immunity 18:849-861; Choi, I. H. et al. (2003) "*Genomic Organization And Expression Analysis Of B7-H4, An Immune Inhibitory Molecule Of The B7 Family,*" J. Immunol. 171:4650-4654). Although freshly isolated human T cells, B cells, monocytes, and dendritic cells do not express B7-H4 on their cell surfaces (as determined via FACS analysis), its expression can be induced on such cells after in vitro stimulation lipopolysaccharides (LPS), phytohemagglutinin (PHA), gamma interferon (IFN-γ), phorbol 12-myristate 13-acetate (PMA), or ionomycin (Sica, G. L. et al. (2003) "*B7-H4, A Molecule Of The B7 Family, Negatively Regulates T Cell Immunity,*" Immunity 18:849-861). The finding of such a wide distribution of B7-H4 expression indicates that the function of B7-H4 is quite distinct from that of other inhibitory B7 molecules (see, Zang, X. et al. (2003) *B7x: A Widely Expressed B7 Family Member That Inhibits T Cell Activation,*" Proc. Natl. Acad. Sci. (USA) 100:10388-10392).

Consistent with this finding and the observation that the extracellular domain of B7-H4 has only about 25% amino acid homology with other B7 family members, B7-H4 does not bind to known B7 family receptors (i.e., CTLA-4, ICOS, PD-1 or CD28). Efforts to identify a B7-H4-specific receptor have revealed that such a receptor is expressed on activated T cells (Sica, G. L. et al. (2003) "*B7-H4, A Molecule Of The B7 Family, Negatively Regulates T Cell Immunity,*" Immunity 18:849-861). Binding of B7-H4 fusion protein to its putative receptor on T cells was found to significantly inhibit T cell proliferation and cytokine (IL-2 and IL-10) production and such inhibition was found to be non-reversible by CD28 costimulation (Zang, X. et al. (2003) *B7x: A Widely Expressed B7 Family Member That Inhibits T Cell Activation,*" Proc. Natl. Acad. Sci. (USA) 100:10388-10392; Prasad, D. V. et al. (2003) *B7S1, A Novel B7 Family Member That Negatively Regulates T Cell Activation,*" Immunity 18:863-873). B7-H4 has been found to arrest cell cycle progression of T cells in $G_0/G_1$ phase (Sica, G. L. et al. (2003) "*B7-H4, A Molecule Of The B7 Family, Negatively Regulates T Cell Immunity,*" Immunity 18:849-861) indicating that the protein mediates its inhibitory effects by arresting the cell cycle rather than by inducing apoptosis.

Anti-B7-H4 antibodies have been found to greatly increase the levels of IL-2 production by spleen cells in vitro, and to lead to a stronger immune response in vivo (Prasad, D. V. et al. (2003) *B7S1, A Novel B7 Family Member That Negatively Regulates T Cell Activation,*" Immunity 18:863-873; Zang, X. et al. (2003) *B7x: A Widely Expressed B7 Family Member That Inhibits T Cell Activation,*" Proc. Natl. Acad. Sci. (USA) 100:10388-10392; Prasad, D. V. et al. (2003) *B7S1, A Novel B7 Family Member That Negatively Regulates T Cell Activation,*" Immunity 18:863-873).

An absence of B7-H4 has been demonstrated to lead to resistance to *Listeria monocytogenes* infection through the direct regulation of the growth of neutrophil progenitors (Zhu, G. et al. (2009) "*B7-H4 Deficient Mice Display Augmented Neutrophil-Mediated Innate Immunity,*" Blood 113:1759-1769; Wei, J. et al. (2011) "*Tissue-Specific Expression Of B7x Protects From CD4 T Cell-Mediated Autoimmunity,*" J. Exper. Med. 208(8):1683-1694). As such B7-H4 has been proposed to play a role in immunity, especially autoimmunity and resistance to infection. Thus agonist anti-B7-H4 antibodies and soluble protein agonists of B7-H4 have been proposed for the treatment of inflammatory disorders (U.S. Pat. No. 7,931,896; United States Patent Publications Nos. 2007/0122378; 2008/0160036; 2009/0142342; and 2011/0020325; European Patent Publication No. EP 2124998; PCT Patent Publications Nos. WO 2006/133396; WO 2007/041694; WO 2008/083228; WO 2009/111315; WO 2010/144295; WO 2011/005566; WO 2011/026122; and WO 2011/026132).

The in vivo significance of B7-H4 is additionally demonstrated by the high levels of B7-H4 expression found in numerous tumor tissues, for example, human ovarian cancers (Choi, I. H. et al. (2003) "*Genomic Organization And Expression Analysis Of B7-H4, An Immune Inhibitory Molecule Of The B7 Family,*" J. Immunol. 171:4650-4654; Kryczek, I. et al. (2006) "*B7-H4 Expression Identifies A Novel Suppressive Macrophage Population In Human Ovarian Carcinoma,*" J. Exp. Med. 203(4):871-881; Bignotti, E. et al. (2006) "*Differential Gene Expression Profiles Between Tumor Biopsies And Short Term Primary Cultures Of Ovarian Serous Carcinomas: Identification Of Novel Molecular Biomarkers For Early Diagnosis And Therapy,*" Gynecol. Oncol. 103:405-416; Tringler, B. et al. (2006) "*B7-H4 Overexpression In Ovarian Tumors,*" Gynecol. Oncol. 100: 44-52; Simon, I. et al. (2006) "*B7-h4 Is A Novel Membrane-Bound Protein And A Candidate Serum And Tissue Biomarker For Ovarian Cancer,*" Cancer Res. 66:1570-1575; Salceda, S. et al. (2005) "*The Immunomodulatory Protein B7-H4 Is Overexpressed In Breast And Ovarian Cancers And Promotes Epithelial Cell Transformation,*" Exp. Cell Res. 306:128-141), non-small-cell lung cancer (Sun, Y. et al. (2006) "*B7-H3 And B7-H4 Expression In Non-Small-Cell Lung Cancer,*" Lung Cancer 53:143-151), ductal and lobular breast cancer (Salceda, S. et al. (2005) "*The Immunomodulatory Protein B7-H4 Is Overexpressed In Breast And Ovarian Cancers And Promotes Epithelial Cell Transformation,*" Exp. Cell Res. 306:128-141; Tringler, B. et al. (2005) "*B7-H4 Is Highly Expressed In Ductal And Lobular Breast Cancer,*" Clin. Cancer Res. 11:1842-1848), and renal cell carcinoma (Krambeck, A. E. et al. (2006) "*B7-H4 Expression In Renal Cell Carcinoma And Tumor Vasculature: Associations With Cancer Progression And Survival,*" Proc. Natl. Acad. Sci. (USA) 103:10391-10396). The expression of B7-H4 on tumor cells has been found to correlate with adverse clinical and pathologic features, including tumor aggressiveness (Krambeck, A. E. et al. (2006) "*B7-H4 Expression In Renal Cell Carcinoma And Tumor Vasculature: Associations With Cancer Progression And Survival,*" Proc. Natl. Acad. Sci. (U.S.A.) 103(2): 10391-10396).

C. Tumor-Associated Macrophages (TAMs)

The association between inflammation and cancer dates back more than a century to observations noting infiltration of large numbers of white blood cells into tumor sites (Balkwill, F. et al. (2001) "*Inflammation And Cancer: Back To Virchow?,*" Lancet 357:539-545; Coussens, L. M. et al. (2002) "*Inflammation and Cancer,*" Nature 420:860-867). Several studies have now identified two main pathways linking inflammation and cancer: an intrinsic and an extrinsic pathway (Allavena, P. et al. (2008) "*Pathways Connecting Inflammation and Cancer,*" Curr. Opin. Genet. Devel. 18:3-10; Colotta, F. (2009) "*Cancer-Related Inflammation, The Seventh Hallmark of Cancer: Links to Genetic Instability,*" Carcinogenesis 30(7): 1073-1081; Porta, C. et al. (2009) "*Cellular and Molecular Pathways Linking Inflammation and Cancer,*" Immunobiology 214:761-777). The intrinsic pathway includes genetic alterations that lead to inflammation and carcinogenesis, whereas the extrinsic pathway is characterized by microbial/viral infections or autoimmune diseases that trigger chronic inflammation in tissues associated with cancer development. Both pathways activate pivotal transcription factors of inflammatory mediators (e.g., NF-κB, STAT3, and HIF-1) and result in the recruitment of leukocytes that play a key role in inflammation (Solinas, G. et al. (2009) "*Tumor-Associated Macrophages (TAM) As Major Players Of The Cancer-Related Inflammation,*" J. Leukoc. Biol. 86(5):1065-1073).

TAMs provide a link between inflammation and cancer. Macrophages are immune system cells derived from activated blood monocytes. They are primarily recognized as participating in inflammatory responses induced by pathogens or tissue damage by acting to remove (i.e., phagocytose) pathogens, dead cells, cellular debris, and various components of the extra-cellular matrix (ECM). Macrophages have been found to constitute an important constituent in the tumor microenvironment and to represent up to 50% of the tumor mass.

In addition to mediating phagocytosis, macrophages secrete pro-angiogenic growth factors and matrix-remodeling proteases, and thus play a role in the development of the vascular infrastructure (i.e., angiogenesis) needed for tumor development and growth (Pollard, J. W. (2009) "*Trophic Macrophages In Development And Disease*," Nat. Rev. Immunol. 9:259-270). As such, the presence of macrophages within a tumor appears to assist the growth of the tumor. A number of studies provide evidence that the presence of tumor-associated macrophages within the tumor is a negative prognostic factor of survival (Farinha, P. et al. (2005) "*Analysis Of Multiple Biomarkers Shows That Lymphoma-Associated Macrophage (LAM) Content Is An Independent Predictor Of Survival In Follicular Lymphoma (FL)*," Blood 106:2169-2174; Dave, S. S. et al. (2004) "*Prediction Of Survival In Follicular Lymphoma Based On Molecular Features Of Tumor-Infiltrating Immune Cells*," N. Engl. J. Med. 351:2159-2169; Solinas, G. et al. (2009) "*Tumor-Associated Macrophages (TAM) As Major Players Of The Cancer-Related Inflammation*," J. Leukoc. Biol. 86(5):1065-1073).

Incipient tumors need to generate their own vasculature to enable oxygen and nourishment delivery to the expanding tumor cells. Thus, the progression of tumors requires coordinated signaling between tumor cells and non-malignant cells in the tumor microenvironment (Kaler, P. et al. (2010) "*Tumor Associated Macrophages Protect Colon Cancer Cells from TRAIL-Induced Apoptosis through IL-1β-Dependent Stabilization of Snail in Tumor Cells*," PLos ONE 5(7):e11700 1-13). It is now well established that TAMs, as well as neutrophils, fibroblasts and other cells cooperate with tumor cells to facilitate angiogenesis in tumors (Nucera, S. et al. (2011) "*The Interplay Between Macrophages And Angiogenesis In Development, Tissue Injury And Regeneration*," Int. J. Dev. Biol. doi: 10.1387/ijdb.103227sn; Zamarron, B. F. et al. (2011) "*Dual Roles Of Immune Cells And Their Factors In Cancer Development And Progression*," Int. J. Biol. Sci. 7(5):651-658; Liu, J. et al. (2011) "*Tumor-Associated Macrophages Recruit CCR6+ Regulatory T Cells And Promote The Development Of Colorectal Cancer Via Enhancing CCL20 Production In Mice*," PLoS One. 6(4):e19495; Rigo, A. et al. (2010) "*Macrophages May Promote Cancer Growth Via A GM-CSF/HB-EGF Paracrine Loop That Is Enhanced By CXCL12*," Molec. Cancer 9(273):1-13; Lin, J. Y. et al. (2011) "*Clinical Significance Of Tumor-Associated Macrophage Infiltration In Supraglottic Laryngeal Carcinoma*," Chin. J. Cancer 30(4):280-286; Vergati, M. (2011) "*The Consequence Of Immune Suppressive Cells In The Use Of Therapeutic Cancer Vaccines And Their Importance In Immune Monitoring*," J. Biomed. Biotechnol. 2011: 182413).

B7-H4 has been shown to be over-expressed in TAMs including those present in ovarian tumors (Kryczek, I. et al. (2006) "*B7-H4 Expression Identifies A Novel Suppressive Macrophage Population In Human Ovarian Carcinoma*," J. Exp. Med. 203(4):871-881; Kryczek, I. et al. (2007) "*Relationship Between B7-H4, Regulatory T Cells, And Patient Outcome In Human Ovarian Carcinoma*," Cancer Res. 67(18):8900-8905).

Despite all prior advances in the treatment of inflammation and cancer, a need remains for improved compositions capable of providing enhanced immunotherapy for the treatment of cancer. Therefore, compositions and their use to treat cancer and other diseases and conditions are provided.

It is an object of the invention to provide compositions and methods for inducing surface B7-H4 internalization to suppress B7-H4 mediated immune evasion for a treatment of cancer, or bacteria or viral infections.

It is another object of the invention to provide compositions and methods for B7-H4 mAb-payload drug-conjugate to target B7-H4 positive tumors for a treatment of cancer.

SUMMARY OF THE INVENTION

B7-H4 binding molecules including murine anti-human B7-H4 antibody "6H3", and chimeric and humanized variants thereof, and their antigen-binding fragments and to derivatives thereof that are capable of immunospecifically binding to B7-H4 and the uses of such molecules in the diagnosis and the treatment of cancer and other diseases are disclosed. Uses of such molecules to retard or prevent tumor growth, inhibit tumor-mediated suppression, eliminate tumors and/or deplete or block the activity of B7-H4-expressing cells, including but not limited to, tumor-associated macrophages ("TAMs"). Reducing or blocking the activity of B7-H4 can alter TAM activity and/or decrease TAM-mediated immune suppression are also disclosed.

For example, molecules, including an antigen-binding fragment of the anti-human B7-H4 antibody 6H3 that immunospecifically binds to human B7-H4 are provided. In some embodiments, the B7-H4 binding molecules are able to bind to B7-H4 arrayed on the surface of a live cell and/or the B7-H4 binding molecules are able to bind to soluble B7-H4 or to B7-H4 expressed at an endogenous concentration. In a particular embodiment, the B7-H4 binding molecules are able to substantially block an activity of soluble B7-H4 or membrane-bound B7-H4.

Molecules including an antigen-binding fragment of the antibody 6H3, wherein the molecules immunospecifically binds to human B7-H4 are disclosed. For example, molecules are provided that can immunospecifically bind to human B7-H4:
  (I) arrayed on the surface of a cell (especially a live cell);
  (II) arrayed on the surface of a cell (especially a live cell) at an endogenous concentration;
  (III) arrayed on the surface of a live cell, and modulates binding between B7-H4 and its cellular receptor;
  (IV) arrayed on the surface of a live cell, and inhibits immune suppression by tumor-associated macrophages;
  (V) arrayed on the surface of a live cell, and modulates an activity of a tumor-associated macrophage;
  (VI) arrayed on the surface of a live tumor cell and inhibits tumor-mediated suppression;
  (VII) arrayed on the surface of a live tumor cell and causes tumor-specific cell lysis
or any combination thereof.

Humanized variants of murine anti-human B7-H4 antibody "6H3" and their antigen-binding fragments and to derivatives thereof that are capable of immunospecifically binding to B7-H4 and the uses of such molecules in the diagnosis and the treatment of cancer and other diseases are also provided. Uses of such molecules to retard or prevent tumor growth, inhibit tumor-mediated suppression, eliminate tumors and/or deplete or block the activity of tumor-associated macrophages ("TAMs") so as to alter their activity and/or decrease TAM-mediated immune suppression are also disclosed.

For example, molecules, including an antigen-binding fragment of a humanized variant of anti-human B7-H4 antibody 6H3 that immunospecifically binds to human B7-H4, wherein the antigen-binding fragment includes:

(1) a light chain variable region of a humanized variant of anti-human B7-H4 antibody 6H3, wherein said light chain variable region has the amino acid sequence of any of SEQ ID NO:18-23; and (2) a heavy chain variable region of a humanized variant of anti-human B7-H4 antibody 6H3, wherein said heavy chain variable region has the amino acid sequence of any of SEQ ID NO:24-29 are provided.

In a particular embodiment the human B7-H4 binding molecules are able to bind to B7-H4 arrayed on the surface of a live cell and/or the B7-H4 binding molecules are able to bind to soluble B7-H4 or to B7-H4 expressed at an endogenous concentration, and particularly the B7-H4 binding molecules are able to substantially block an activity of soluble B7-H4 or membrane-bound B7-H4.

Thus molecules including an antigen-binding fragment of a humanized variant of antibody 6H3, wherein the molecule immunospecifically binds to human B7-H4 are provided. For example, molecules are provided that can immunospecifically bind to human B7-H4:

(I) arrayed on the surface of a cell (especially a live cell);
(II) arrayed on the surface of a cell (especially a live cell) at an endogenous concentration;
(III) arrayed on the surface of a live cell, and modulates binding between B7-H4 and its cellular receptor;
(IV) arrayed on the surface of a live cell, and inhibits immune suppression by tumor-associated macrophages;
(V) arrayed on the surface of a live cell, and modulates an activity of a tumor-associated macrophage;
(VI) arrayed on the surface of a live tumor cell and inhibits tumor-mediated suppression;
(VII) arrayed on the surface of a live tumor cell and causes tumor-specific cell lysis or any combination thereof.

Also disclosed are embodiments of such molecules wherein such molecules are detectably labeled or include a conjugated toxin, drug, receptor, enzyme, receptor ligand. In some embodiments the disclosed molecules are capable of being internalized into the cell and of mediating the death of the cell.

The live cell can be a tumor cell, a pathogen-infected cell or a macrophage.

The molecule can be a monoclonal antibody, a human antibody, a chimeric antibody, a humanized antibody, or an antigen binding fragment thereof.

The molecules can be an IgG1 or IgG4 antibody. The molecules can have ADCC activity, can have direct tumor killing activity, can have ADC activity, and/or can inhibit TAM-mediated and/or tumor-mediated suppression.

The molecule can be a bispecific, trispecific or multispecific antibody, for example, one that is capable of binding B7-H4 and a different molecule on the same cell.

Pharmaceutical compositions including the disclosed B7-H4 binding molecules, and their use for the treatment of cancer or infectious disease are disclosed. The pharmaceutical compositions can include a therapeutically effective or prophylactically effective amount of one or more B7-H4 binding molecules, and a physiologically acceptable carrier or excipient, wherein the molecule antagonizes a B7-H4-mediated suppression to up-modulate an immune response.

The pharmaceutical compositions can be used for the treatment of cancer or infectious disease (especially a chronic viral infection) in a subject exhibiting a symptom of the cancer or infectious disease or for the prevention of cancer or infectious disease in a subject in advance of the exhibition of the symptom. Therefore, prophylactic uses are also provided.

Pharmaceutical compositions for the treatment of inflammation, including a therapeutically effective or prophylactically effective amount of one or more B7-H4 binding molecules, and a physiologically acceptable carrier or excipient, wherein the molecule enhances B7-H4-mediated suppression to down-modulate an immune response are also disclosed.

The pharmaceutical compositions can be used for the treatment of inflammation (especially an autoimmune disease, a graft vs host disease, a host vs graft disease, or a transplantation rejection response, and the use is the treatment of the autoimmune disease, a graft vs host disease, a host vs graft disease, or a transplantation rejection response).

The disclosed molecules can be used in a cytologic assay for diagnosing the presence of a disease (especially cancer or a disease affecting T cell number or health) in a subject. In a particular embodiment, the cytologic assay includes assaying cells of the subject for their ability to bind to the molecule.

The disclosed molecules can be used to determine the suitability of a subject for treatment of a tumor with an anti-cancer agent. The use can include determining the effective or actual concentration of tumor-associated macrophages in the tumor, and/or the level of B7-H4 expression on tumor cells. In a particular embodiment, the dose of the anti-cancer agent or the treatment with the anti-cancer agent is set or adjusted based on the determined effective or actual concentration of the tumor-associated macrophages.

A therapeutically effective amount of the disclosed pharmaceutical compositions can be used for treating cancer in a patient. In some embodiments, the patient is identified as exhibiting high levels of B7-H4 expression on tumor cells and/or an elevated effective concentration of B7-H4-expressing tumor-associated macrophages.

A therapeutically effective amount of the disclosed pharmaceutical compositions can also be used to stimulate, enhance, or increase an immune stimulating response, to reduce, delay, or prevent an immune inhibitory response, or a combination thereof in a subject. In some embodiments, the subject has or is likely to develop cancer or a tumor, or has or is likely to develop an infection. In some embodiments, the pharmaceutical composition is effective to stimulate, enhance or increase an immune stimulating response against cancer cells or infected cells.

In some embodiments, treatment of a tumor or cancer additionally includes chemotherapy, a hormonal therapy, a biological therapy, an immunotherapy, a radiation therapy or surgery.

In some embodiments one or more of the disclosed B7-H4 binding molecules, contact a tumor cell, a pathogen-infected cell or a macrophage.

In particular embodiments, the B7-H4 binding molecule modulates binding between B7-H4 and its cellular receptor.

BRIEF DESCRIPTION OF THE DRAWINGS

FIG. 3B: CD8, isotype control; FIG. 3C: CD4, Anti-B7-H4 Antibody 6H3; FIG. 3D: CD8, Anti-B7-H4 Antibody 6H3).

FIG. 11A is a series of histograms showing the results of flow cytometry measurements of CypHer5B fluorescence of 293T B7-H4 transfectants 0, 1 and 3 hours after incubation with CypHer labeled antibody 6H3. FIG. 11B is a line graph showing B7-H4 surface staining and CyperHer fluorescence over time.

FIGS. 13A and 13B are images of 6H3-stained salivary gland tissue; FIG. 13C shows two different but related serous cystic lesions of the ovary.

FIGS. 18A and 18B are a bar graphs showing internalization of anti-B7-H4 antibodies in E.G7ova/hB7-H4 cells (FIG. 18A) and CT26/hB7-H4 cells (FIG. 18B) (from left to right along the x-axis): human chimeric 6H3, humanized 6H3 V2, humanized 6H3 V6, humanized 6H3 V7, humanized 6H3 V9, humanized 6H3 V12, humanized 6H3 V14, 6H3.m1 (mouse IgG1), 6H3.m2a (mouse IgG2a), negative control (anti-PD-1 antibody), and no treatment.

FIG. 19A-19C are line graphs showing the % specific lysis of EG7.B7H4 target cells by effector cells for four different healthy peripheral blood mononucleated cell (PBMC) donors (117, 119, 121, 122) as a function of chimeric 6H3 antibody concentration (log (ng/ml)) at three different effector cell:target cell ratios: 500,000:25,000 (FIG. 19A), 500,000:10,000 (FIG. 19B), and 500,000:5,000 (FIG. 19C) in an assay designed to measure antibody-dependent cell-mediated cytotoxicity (ADCC).

FIG. 20 is a bar graph showing the % specific lysis of EG7.B7H4 target cells by effector cells from three different donors peripheral blood mononucleated cell (PBMC) (114, 121, 122) for 14 different humanized variants of 6H3 in an assay designed to measure antibody-dependent cell-mediated cytotoxicity (ADCC) (antibody concentration 10 ng/ml; target cell:effector cell ratio of 1:20).

FIG. 24A shows RFU (relative fluorescent units—black corrected) for various antibodies and antibody concentrations at control, 1:2 complement, and 1:5 complement dilutions. For each complement dilution the cluster of bars represent, from left to right: formulation buffer, 50 µg/ml IgG1 (negative control), 5 µg/ml IgG1 (negative control), 0.5 µg/ml IgG1 (negative control), 50 µg/ml chimeric 6H3, 5 µg/ml chimeric 6H3, 0.5 µg/ml chimeric 6H3, 50 µg/ml HERCEPTIN®, 5 µg/ml HERCEPTIN®, 0.5 µg/ml HERCEPTIN®. FIG. 24B shows the specific lysis for various antibodies and antibody concentrations at control, 1:2 complement, and 1:5 complement dilutions. For each complement dilution the cluster of bars represent, from left to right: 50 µg/ml chimeric 6H3, 5 µg/ml chimeric 6H3, 0.5 µg/ml chimeric 6H3, 50 µg/ml HERCEPTIN®, 5 µg/ml HERCEPTIN®, 0.5 µg/ml HERCEPTIN®.

FIG. 26 is a bar graph showing the % specific lysis of EG7.B7H4+OVA target cells at different effector cell:target cell ratios in the presence of control IgG or chimeric 6H3 antibody in a CTL-mediated lysis assay. For each effector cell:target cell ratio the cluster of bars represent, from left to right: 1 µg/ml control IgG, 10 µg/ml control IgG, 1 µg/ml chimeric 6H3, and 10 µg/ml chimeric 6H3.

FIG. 27A is line graph showing tumor volume ($mm^3$) over time (days post tumor inoculation) in a first experiment utilizing a Lewis Lung Carcinoma (LCC) tumor mouse model where tumor-bearing mice were treated with formulation buffer control (-♦-), 6H3.m1 (-■-) or 6H3.m2a (-▲-). FIG. 27B is Kaplan-Meier curve showing % survival of mice over time (days post tumor inoculation) in a Lewis Lung Carcinoma (LCC) tumor mouse model where mice were treated with formulation buffer control (-●-), 6H3.m1 (-■-), or 6H3.m2a (-▲-).

FIG. 28A is line graph showing tumor volume ($mm^3$) over time (days post tumor inoculation) in a second experiment utilizing a Lewis Lung Carcinoma (LCC) tumor mouse model where tumor-bearing mice were treated with formulation buffer control (-♦-), 6H3.m1 (-■-) or 6H3.m2a (-▲-). FIG. 28B is Kaplan-Meier curve showing % survival of mice over time (days post tumor inoculation) in a Lewis Lung Carcinoma (LCC) tumor mouse model where mice were treated with formulation buffer control (-●-), 6H3.m1 (-■-), or 6H3.m2a (-▲-).

FIGS. 38A-38D are line graphs showing secretion of IL-17 (FIG. 38A), IFNγ (FIG. 38B), proliferation ([$^3$H]-thymidine incorporation) (FIG. 38C), and secretion of IL-10 secretion (FIG. 38D) for cells treated with B7-H4-Ig fusion protein in combination with various concentrations (0, 1.11 µ/g/ml, 3.33 µ/g/ml, or 10 µ/g/ml) of chimeric 6H3 ("parent") or a humanized variant of 6H3. * with Control Ig.

DETAILED DESCRIPTION OF THE INVENTION

Figure 1A:
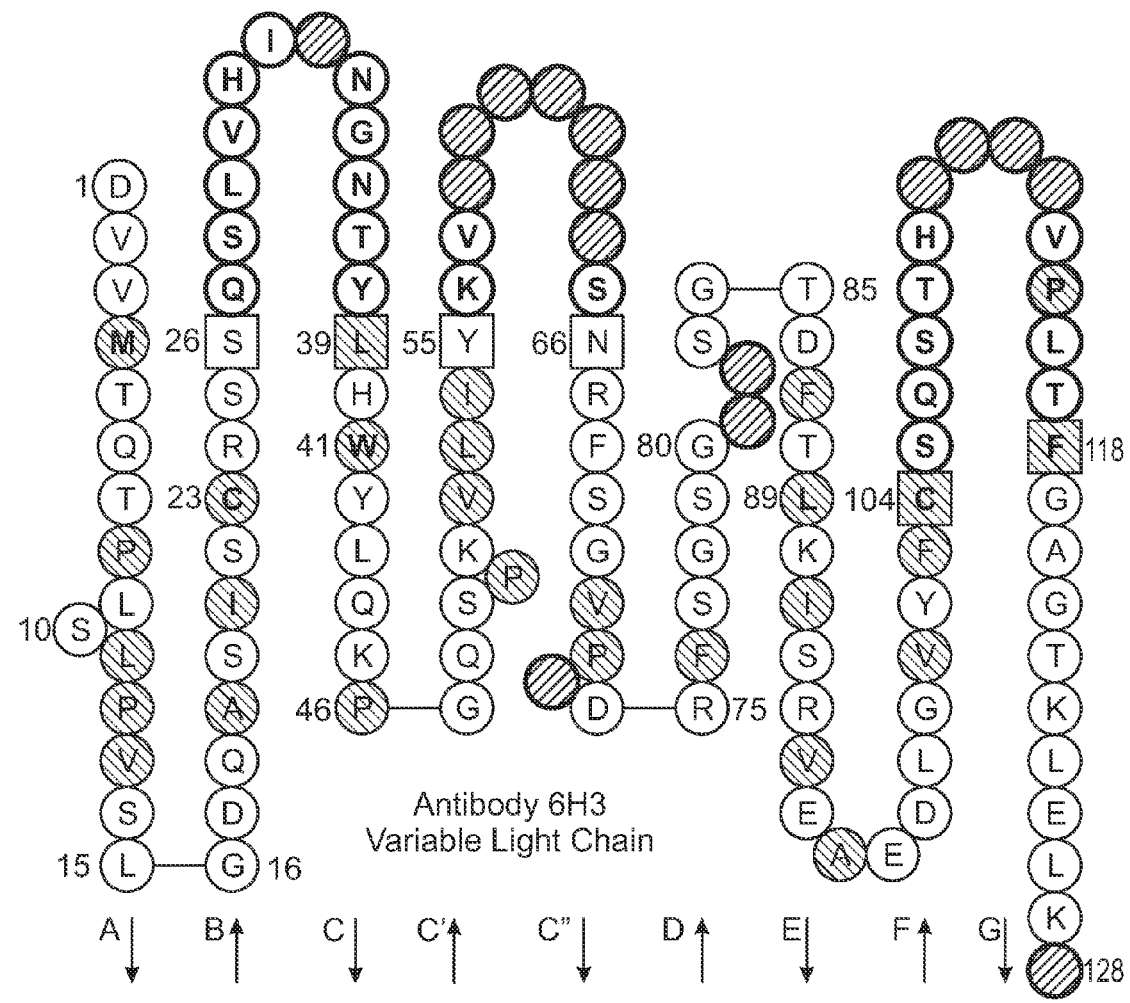
FIGS. 1A-1B are diagrams showing Collier Perles 2D representations of the variable domains of the light chain (FIG. 1A) and heavy chain (FIG. 1B) of murine antibody 6H3. The three CDR loops of the chains are shown at the top of the diagrams.

The high levels of B7-H4 expression found in numerous tumor tissues, for example, human ovarian cancers, points to a key role for B7-H4 in mediating immune suppression. Also, TAMs expressing B7-H4 have been found to suppress tumor-associated antigen-specific T cell immunity (Kryczek, I. et al. (2006) "*B7-H4 Expression Identifies A Novel Suppressive Macrophage Population In Human Ovarian Carcinoma,*" J. Exp. Med. 203(4):871-881). The intensity of B7-H4 expression in TAMs correlates significantly with Treg cell numbers in the tumor. Furthermore, B7-H4 expressed on TAMs, is associated with poor patient outcome (Kryczek, I. et al. (2006) "*B7-H4 Expression Identifies A Novel Suppressive Macrophage Population In Human Ovarian Carcinoma,*" J. Exp. Med. 203(4):871-881). Previously published data also showed that TAMs spontaneously produce chemokine CCL22 that mediates Treg cell trafficking into the tumor, and Treg cell-induced B7-H4 expression on antigen-presenting cells (APC), including TAMs themselves (Kryczek, I. et al. (2006) "*Cutting Edge: Induction Of B7-H4 On APCs Through IL-10: Novel Suppressive Mode For Regulatory T Cells,*" J. Immunol. 177(1):40-44). Taken together, such findings indicate that tumor cells and TAMs expressing B7-H4 play a very important role on immune suppression in the tumor microenvironment allowing the tumor to avoid detection by the immune system ("immune evasion"). By blocking B7-H4, modulating its surface expression, modulating B7-H4-mediated signal transduction, or depleting TAMs, disclosed molecules that are capable of immunospecifically binding to B7-H4, or preventing interaction with its native receptor, provide a strategy as an effective immunotherapy for cancer.

Molecules that are capable of immunospecifically binding to B7-H4, as well as uses of such molecules in the diagnosis and the treatment of cancer and other diseases are provided. Use of the molecules to retard or prevent tumor growth, inhibit tumor-mediated suppression, eliminate tumors and/or deplete or block the activity of tumor-associated macrophages ("TAMs") so as to alter their activity and/or decrease TAM-mediated immune suppression are also provided.

In particular, such molecules and particularly such molecules that are hIgG1 or hIgG4 antibodies, can be used to target B7-H4-expressing cells, tumors or TAMs and screen for various functional activities, including modulating the interaction between B7-H4 and its receptor(s), modulation of B7-H4 levels and attenuation of negative signaling and/or depletion of B7-H4 positive cells. Using recombinant DNA technology, such molecules can be engineered to include constant regions to form Fc domains having little or no Fc receptor (FcR) binding activity, enhanced antibody-dependent cell-mediated cytotoxicity (ADCC) or enhanced complement dependent cytotoxicity (CDC) activities. Such recombinant molecules can be used as modulatory molecules to decrease or prevent B7-H4 on tumors or TAMs from interacting with inhibitory receptor(s) on T cells or other cells in the tumor microenvironment, thereby releasing T cells or other functional cells from B7-H4 check point ("break")/suppressive signaling. In contrast, such molecules can be engineered to include constant regions to form functional Fc domains, and which therefore may induce ADCC or CDC, causing depletion of the tumor cells or TAMs expressing B7-H4, which potentially releases T cells or other functional cells from check point blockade, in addition to other activities such as B7-H4 modulation from the surface of suppressive cells, or direct killing of B7-H4 expressing cells. Anti-B7-H4 antibodies with ADCC activity can be particularly useful for simultaneously depleting B7-H4-expressing tumor cells and inhibiting TAM-mediated immune suppression.

In a specific aspect, the present disclosure provides an Fc variant, wherein the Fc region includes at least one modification (e.g., amino acid substitutions, amino acid insertions, amino acid deletions) at one or more positions selected from the group consisting of 228, 234, 235 and 331 as numbered by the EU index as set forth in Kabat et al. (1991, NIH Publication 91-3242, National Technical Information Service, Springfield, Va.).

In one aspect, the modification is at least one substitution selected from the group consisting of 228P, 234F, 235E, 235F, 235Y, and 331S as numbered by the EU index as set forth in Kabat.

In another specific aspect, the present disclosure provides an Fc variant, wherein the Fc region is an IgG4 Fc region and comprises at least one modification at one or more positions selected from the group consisting of 228 and 235 as numbered by the EU index as set forth in Kabat. In still another specific aspect, the Fc region is an IgG4 Fc region and the non-naturally occurring amino acids are selected from the group consisting of 228P, 235E and 235Y as numbered by the EU index as set forth in Kabat.

In another specific aspect, the present disclosure provides an Fc variant, wherein the Fc region includes at least one non-naturally occurring amino acid at one or more positions selected from the group consisting of 239, 330 and 332 as numbered by the EU index as set forth in Kabat. In one aspect, the modification is at least one substitution selected from the group consisting of 239D, 330L, 330Y, and 332E as numbered by the EU index as set forth in Kabat. See, U.S. Pat. No. 7,317,091, incorporated herein by referenced in its entirety.

In a specific aspect, the present disclosure provides an Fc variant, wherein the Fc region includes at least one non-naturally occurring amino acid at one or more positions selected from the group consisting of 252, 254, and 256 as numbered by the EU index as set forth in Kabat. In one aspect, the modification is at least one substitution selected from the group consisting of 252Y, 254T and 256E as numbered by the EU index as set forth in Kabat. See, U.S. Pat. No. 7,083,784, incorporated herein by reference in its entirety.

In certain aspects, the present disclosure provides an Fc variant, wherein the Fc region includes a non-naturally occurring amino acid at position 428 as numbered by the EU index as set forth in Kabat. In one aspect, the modification at position 428 is selected from the group consisting of 428T, 428L, 428F, and 428S as numbered by the EU index as set forth in Kabat. See, U.S. Pat. No. 7,670,600, incorporated herein by reference in its entirety. In another aspect, an Fc variant may further include a non-naturally occurring amino acid at position 434 as numbered by the EU index as set forth in Kabat. In one aspect, the modification at position 434 is selected from the group consisting of 434A, 434S, and 434F as numbered by the EU index as set forth in Kabat. In other aspects, the present disclosure provides an Fc variant, wherein the Fc region includes a non-naturally occurring amino acid at positions 428 and 434 as numbered by the EU index as set forth in Kabat. In a specific aspect, the Fc region comprises 428L, 434S. See, U.S. Pat. No. 8,088,376.

```
The amino acid sequence of human B7-H4 is:
                                          (SEQ ID NO: 1)
MASLGQILFW SIISIIIILA GAIALIIGFG ISGKHSITVT

TVASAGNIGE DGILSCTFEP DIKLSDIVIQ WLKEGVLGLV

HEFKEGKDEL SEQDEMFRGR TAVFADQVIV GNASLRLKNV

QLTDAGTYKC YIITSKGKGN ANLEYKTGAF SMPEVNVDYN

ASSETLRCEA PRWFPQPTVV WASQVDQGAN FSEVSNTSFE

LNSENVTMKV VSVLYNVTIN NTYSCMIEND IAKATGDIKV

TESEIKRRSH LQLLNSKASL CVSSFFAISW ALLPLSPYLM LK

The amino acid sequence of murine B7-H4 is
                                          (SEQ ID NO: 2):
MASLGQIIFW SIINIIIILA GAIALIIGFG ISGKHFITVT

TFTSAGNIGE DGTLSCTFEP DIKLNGIVIQ WLKEGIKGLV

HEFKEGKDDL SQQHEMFRGR TAVFADQVVV GNASLRLKNV

QLTDAGTYTC YIRTSKGKGN ANLEYKTGAF SMPEINVDYN
```

-continued

```
ASSESLRCEA PRWFPQPTVA WASQVDQGAN FSEVSNTSFE

LNSENVTMKV VSVLYNVTIN NTYSCMIEND IAKATGDIKV

TDSEVKRRSQ LQLLNSGPSP CVFSSAFVAG WALLSLSCCL MLR
```

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen (and in particular, the antigen B7-H4) if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region. A molecule is said to "physiospecifically bind" a second molecule if such binding exhibits the specificity and affinity of a receptor to its cognate binding ligand. B7-H4 molecules (e.g., B7-H4 proteins or fusion molecules, etc.) are said to be capable of "physiospecifically binding" to a target region or conformation ("epitope") of a receptor or of B7-H4 if such binding involves the B7-H4-receptor recognition sites. A molecule can be capable of physiospecifically binding to more than one other molecule.

The disclosed molecules can have the ability to "deplete" (i.e., partially or completely decrease) the concentration of B7-H4 expressing cells, including, but not limited to TAMs, present within a tumor or block the activity of the B7-H4 expressing cells. Such depletion can relate to the absolute numbers of macrophages present within (or recruited to) a tumor, or it can relate to the concentration of active macrophages (i.e., the concentration of macrophages within or recruited to a tumor that possesses a capability to mediate a pro-angiogenic or pro-tumorigenic effect). Preferably, such depletion will provide at least a 10% change in a measurable immune system activity (for example, macrophage count, angiogenic potential, vascularization, macrophage viability, etc.), more preferably, at least a 50% change in such activity, or at least a 2-fold, 5-fold, 10-fold, or still more preferably, at least a 100-fold change in such activity.

As used herein the term "modulate" relates to a capacity to alter an effect or result. For example, polypeptides that include murine anti-human B7-H4 antibody 6H3, or a chimeric or humanized variant thereof, or any of their antigen-binding fragments that immunospecifically bind human B7-H4 or molecules that physiospecifically bind B7-H4 or its cognate receptor) that are capable of modulating the binding between B7-H4 and its cognate receptor and/or of modulating the signal transduction that occurs as a consequence of B7-H4-cognate receptor binding are provided. Such modulation can be partial (i.e., attenuating, but not abolishing, an activity of B7-H4) or it can completely abolish such activity (e.g., neutralize the ability of B7-H4 to mediate signal transduction). Modulation can include internalization of the receptor following binding of the antibody or a reduction in expression of the receptor on the target cell. In a further embodiment, such modulation can enhance or otherwise agonize the interaction between B7-H4 and its cognate receptor, facilitating B7-H4-cognate receptor binding or signal transduction. In a still further embodiment, such modulation can alter the nature of the interaction between B7-H4 and its cognate receptor so as to alter the nature of the elicited signal transduction. For example, the molecules can, by binding to B7-H4, alter the ability of such molecules to bind to other receptors and thereby alter their overall activity. Preferably, such modulation will provide at least a 10% change in a measurable immune system activity, more preferably, at least a 50% change in such activity, or at least a 2-fold, 5-fold, 10-fold, or still more preferably, at least a 100-fold change in such activity. Such modulation can therefore result in attenuating or in completely abolishing the ability of B7-H4 (for example, on tumor cells) to bind to its cognate receptor and therefore decrease (or prevent) the inhibition of the immune response mediated by B7-H4. As such, treatments for cancer, infectious disease, and other diseases in which an enhanced immune response is desired are also disclosed. Alternatively, B7-H4-binding molecules can exert a modulating activity on tumor specific B7-H4 that could impact the growth, development, viability, activity, etc. of the tumor directly.

The term "substantially," as used in the context of binding or exhibited effect, is intended to denote that the observed effect is physiologically or therapeutically relevant. Thus, for example, a molecule is able to substantially block an activity of soluble B7-H4 or membrane-bound B7-H4 if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "co-stimulatory" signals that are mediated by B7-H4 encompass positive co-stimulatory signals (e.g., signals that result in enhancing an activity) and negative co-stimulatory signals (e.g., signals that result in inhibiting an activity).

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multispecific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Production and use of "derivatives" of any of the disclosed antibodies and antigen-binding fragments are also disclosed. The term "derivative" refers to an antibody or antigen-binding fragment thereof that immunospecifically binds to human B7-H4 but which differs in amino acid sequence from murine anti-human B7-H4 antibody 6H3 by including one, two, three, four, five or more amino acid substitutions, additions, deletions or modifications relative to antibody 6H3. Preferably such derivatives will have substantially the same immunospecificity and/or characteristics, or the same immunospecificity and characteristics as antibody 6H3. The amino acid substitutions or additions of such derivatives can include naturally occurring (i.e., DNA-encoded) or non-naturally occurring amino acid residues. The term "derivative" encompasses, for example, chimeric or humanized variants of antibody 6H3, as well as variants having altered CHL hinge, CH2, CH3 or CH4 regions, so as to form, for example antibodies, etc., having variant Fc regions that exhibit enhanced or impaired effector or binding characteristics. The term "derivative" additionally encompasses non amino acid modifications, for example, amino acids that can be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RHI,*" Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha (1-6) Dextran Increases Its Affinity For Antigen,*" J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region,*" J. Immunol. 143(8): 2595-2601; Routledge, E. G. et al. (1995) "*The Effect Of Aglycosylation On The Immunogenicity Of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity.*," J. Biol. Chem. 277(30): 26733-26740).

A "chimeric antibody" is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397. Chimeric antibodies including one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332).

The antibodies disclosed herein include "humanized antibodies" (see, e.g., European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J. Immunol.* 169:1119-1125; Caldas et al., 2000, *Protein Eng.* 13:353-360; Morea et al., 2000, *Methods* 20:267-79; Baca et al., 1997, *J. Biol. Chem.* 272:10678-10684; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-973; Jones et al., 1986, *Nature* 321:522-525; Reichmann et al., 1988, *Nature* 332:323-329; and Presta, 1992, *Curr. Op. Struct. Biol.* 2:593-596). As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, preferably about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies can include residues which are not found in the recipient antibody or in the donor antibody. These modifications are made to further refine antibody performance. In general, the humanized antibody will include substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will include at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations).

In a particularly preferred embodiment, the antibodies and antigen-binding fragments are selected for their ability to bind to tumors or TAMs and to thereby deplete such cells or modulate their activity.

Human, chimeric or humanized derivatives of the murine anti-human B7-H4 antibody 6H3 are particularly preferred for in vivo use in humans, however, murine antibodies or antibodies of other species can be advantageously employed for many uses (for example, in vitro or in situ detection assays, acute in vivo use, etc.). Such a human or humanized antibody can include amino acid residue substitutions, deletions or additions in one or more non-human CDRs. The humanized antibody derivative can have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Such human antibodies can be made by a variety of methods known in the art including phage display methods using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Such human antibodies can be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

In some embodiments the disclosed antibodies are monospecific. Of particular interest are bispecific derivatives of such antibodies, trispecific derivatives of such antibodies or derivative antibodies of greater multi-specificity, that exhibit specificity to different immune system targets in addition to their specificity for human B7-H4. For example, such antibodies can bind to both human B7-H4 and to an antigen that is important for targeting the antibody to a particular cell type or tissue (for example, to an antigen associated with a cancer antigen of a tumor being treated). In another embodiment, such multispecific antibody binds to molecules (receptors or ligands) involved in alternative immunomodulatory pathways, such as B7-H1, PD-1, CTLA4, TIM3, TIM4, OX40, CD40, GITR, 4-1-BB, LIGHT or LAG3, in order to enhance the immunomodulatory effects and combine multiple mechanisms of action, such as ligand blocking, immune cell activation and direct tumor targeting, in one molecule. For example, B7-H1 is also expressed on tumors and TAMs and a bi-specific antibody targeting both B7-H1 and B7-H4 would provide enhanced inhibition of TAM-mediated immune suppression, as well as enhanced inhibition of tumor-mediated B7-H1+ and B7-H4+ immune suppression. Furthermore, a bi-specific antibody targeting both PD-1 and B7-H4 would inhibit TAM-mediated immune suppression, inhibit tumor-mediated immune suppression (through both the B7-H4 and PD-1 pathways), reinvigorate exhausted T cells to enhance effector CTL recognition, and redirect/target effector CTL to tumor via a PD-1:B7-H4 "bridge." Furthermore, the multispecific antibody can bind to effector molecules such as cytokines (e.g., IL-7, IL-15, IL-12, IL-4 TGF-beta, IL-10, IL-17, IFNg, Flt3, BLys) and chemokines (e.g., CCL21), which can be particularly relevant for modulating both acute and chronic immune responses. Likewise, an internalizing or toxin-conjugated antibody capable of binding B7-H4 can be employed to mediate the intracellular uptake and induced killing of tumor cells that express B7-H4.

Macrophages have been shown to contribute significantly to the initial steps of HIV infection (Carter, C. A. et al. (2008) "*Cell Biology Of HIV-1 Infection Of Macrophages,*" Ann. Rev. Microbiol. 62:425-443; Noursadeghi, M. et al. (2006) "*HIV-1 Infection Of Mononuclear Phagocytic Cells: The Case For Bacterial Innate Immune Deficiency In AIDS,*" Lancet Infect. Dis. 6:794-804). Accordingly, the disclosed antibodies or antigen binding fragments thereof (particularly if conjugated to a toxin) that bind B7-H4 and a macrophage-specific marker such as CD14, CD68, CD163, TLR2 etc.) can be used for preventing HIV infection.

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions can be naturally occurring or consensus framework regions, and preferably human framework regions (see, e.g., Chothia et al., 1998, "*Structural Determinants In The Sequences Of Immunoglobulin Variable Domain,*" *J. Mol. Biol.* 278: 457-479 for a listing of human framework regions).

A human, humanized or chimeric antibody derivative can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, such antibodies also includes at least a portion of an immunoglobulin constant region (Fc), typically that of a human immunoglobulin. The constant domains of such antibodies can be selected with respect to the proposed function of the antibody, in particular the effector function which may be required. In some embodiments, the constant domains of such antibodies are or can include human IgA, IgD, IgE, IgG or IgM domains. In a specific embodiment, human IgG constant domains, especially of the IgG1 and IgG3 isotypes are used, when the humanized antibody derivative is intended for a therapeutic use and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody is intended for therapeutic purposes and antibody effector function is not required. Fc constant domains including one or more amino acid modifications which alter antibody effector functions such as those disclosed in U.S. Patent Application Publication Nos. 2005/0037000 and 2005/0064514.

In some embodiments, the disclosed molecule contains both an antibody light chain as well as at least the variable domain of an antibody heavy chain. In other embodiments, such molecules can further include one or more of the CH1, hinge, CH2, CH3, and CH4 regions of the heavy chain (especially, the CH1 and hinge regions, or the CH1, hinge and CH2 regions, or the CH1, hinge, CH2 and CH3 regions). The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain can be of the $IgG_2$ or $IgG_4$ class. The antibody can include sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework can be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323).

The B7-H4 binding molecules can be produced by any method known in the art useful for the production of polypeptides, e.g., in vitro synthesis, recombinant DNA production, and the like. Preferably, the humanized antibodies are produced by recombinant DNA technology. The antibodies can be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

An exemplary process for the production of the recombinant chimeric antibodies can include the following: a) constructing, by conventional molecular biology methods, an expression vector that encodes and expresses an antibody heavy chain in which the CDRs and variable region of an anti-B7-H4 antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human B7-H4 monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized antibodies can include the following: a) constructing, by conventional molecular biology methods, an expression vector that encodes and expresses an anti-human B7-H4 heavy chain in which the CDRs and a minimal portion of the variable region framework that are required to retain donor antibody binding specificity are derived from the humanized variants of anti-human B7-H4 antibody 6H3, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as murine anti-human B7-H4 monoclonal antibody 6H3, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, are preferably identical. This procedure provides for equal expression of heavy and light chain polypeptides. Alternatively, a single vector can be used which encodes both heavy and light chain polypeptides. The coding sequences for the heavy and light chains can include cDNA or genomic DNA or both. The host cell used to express the recombinant antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands).

Any of the disclosed antibodies can be used to generate antiidiotype antibodies using techniques well known to those skilled in the art (see, e.g., Greenspan, N. S. et al. (1989) "*Idiotypes: Structure And Immunogenicity*," FASEB J. 7:437-444; and Nisinoff, A. (1991) "*Idiotypes: Concepts And Applications*," J. Immunol. 147(8):2429-2438).

A derivative antibody or antibody fragment can be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Substitutions, additions or deletions in the derivatized antibodies can be in the Fc region of the antibody and can thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821. In some embodiments, antibodies whose Fc region have been deleted (for example, an Fab or F(ab)2, etc.) or modified so that the molecule exhibits diminished or no Fc receptor (FcR) binding activity, or exhibits enhanced antibody-dependent cell-mediated cytotoxicity (ADCC) or complement dependent cytotoxicity (CDC) activities. In some embodiments, the antibodies have altered affinity for an activating FcγR, e.g., FcγRIIIA Preferably such modifications also have an altered Fc-mediated effector function. Modifications that affect Fc-mediated effector function are well known in the art (see U.S. Pat. No. 6,194,551, and WO 00/42072). In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

Derivatized antibodies can be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized antibodies can be engineered to increase biological half-lives (see, e.g. U.S. Pat. No. 6,277,375). For example, humanized antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies can also be modified by the methods and coupling agents described by Davis et al. (See U.S. Pat. No. 4,179,337) in order to provide compositions that can be injected into the mammalian circulatory system with substantially no immunogenic response.

The framework residues of the humanized antibodies can be modified. Residues in the framework regions can be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) *Reshaping Human Antibodies For Therapy,*" Nature 332:323-327).

The disclosed B7-H4 binding molecules can be recombinantly fused or chemically conjugated (including both covalently and non-covalently conjugations) to a heterologous molecule (i.e., an unrelated molecule). The fusion does not necessarily need to be direct, but may occur through linker sequences.

In one embodiment such heterologous molecules are polypeptides having at least 10, at least 20, at least 30, at least 40, at least 50, at least 60, at least 70, at least 80, at least 90 or at least 100 amino acids. Such heterologous molecules can alternatively be enzymes, hormones, cell surface receptors, drug moieties, such as: macrophage-specific targeting reagents (such as the intracellular carboxylesterase, hCE1 (Needham, L. A. et al. (2011) "*Drug Targeting To Monocytes And Macrophages Using Esterase-Sensitive Chemical Motif,*" J. Pharmacol. Exp. Ther. DOI:10.1124/jpet.111.183640), chitin and chitosan (Muzzarelli, R. A. (2010) "*Chitins And Chitosans As Immunoadjuvants And Non-Allergenic Drug Carriers,*" Mar Drugs 8(2):292-312), galactosylated low-density lipoprotein (Wu, F. et al. (009) "*Galactosylated LDL Nanoparticles: A Novel Targeting Delivery System To Deliver Antigen To Macrophages And Enhance Antigen Specific T Cell Responses,*" Molec. Pharm. 6(5):1506-1517), N-formyl-Met-Leu-Phe (fMLF), a macrophage-specific chemo-attractant (Wan, L. et al. (2008) "*Optimizing Size And Copy Number For PEG-Fmlf (N-Formyl-Methionyl-Leucyl-Phenylalanine) Nanocarrier Uptake By Macrophages,*" Bioconjug. Chem. 19(1):28-38), maleylated or mannosylated protein, such as maleylated albumin (Anatelli, F. et al. (2006) "*Macrophage-Targeted Photosensitizer Conjugate Delivered By Intratumoral Injection,*" Mol Pharm. 3(6):654-664; Bansal, P. et al. (1999) "*MHC Class I-Restricted Presentation Of Maleylated Protein Binding To Scavenger Receptors,*" J. Immunol. 162(8): 4430-4437); see also Mukhopadhyay, A. et al. (2003) "*Intracellular Delivery Of Drugs To Macrophages,*" Adv. Biochem. Eng. Biotechnol. 84:183-209), toxins (such as abrin, ricin A, *pseudomonas* exotoxin (i.e., PE-40), diphtheria toxin, ricin, gelonin, or pokeweed antiviral protein), proteins (such as tumor necrosis factor, interferon (e.g., α-interferon, (3-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF"), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

In another embodiment, the molecules are conjugated to a second antibody to form an antibody heteroconjugate as described by Segal in U.S. Pat. No. 4,676,980. Such heteroconjugate antibodies can additionally bind to haptens (such as fluorescein, etc.), or to cellular markers (e.g., 4-1-BB, B7-H1, PD-1, CD4, CD8, CD14, CD25, CD27, CD40, CD68, CD163, CTLA4, GITR, LAG-3, OX40, TIM3, TIM4, TLR2, LIGHT, etc.) or to cytokines (e.g., IL-4, IL-7, IL-10, IL-12, IL-15, IL-17, TGF-beta, IFNg, Flt3, BLys) or chemokines (e.g., CCL21), etc.

The Fc portion of the fusion protein can be varied by isotype or subclass, can be a chimeric or hybrid, and/or can be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells*," Mol. Immun 34(6):441-452, Swann, P. G. (2008) "*Considerations For The Development Of Therapeutic Monoclonal Antibodies*," Curr. Opin. Immun. 20:493-499 (2008), and Presta, L. G. (2008) "*Molecular Engineering And Design Of Therapeutic Antibodies*," Curr. Opin. Immun 20:460-470. In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region can include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. Therefore, the Fc domain can the disclosed antibodies and fragments contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduced binding to FcγR, which increases their half-life. Representative IgG2-4 hybrids and IgG4 mutants are described in Angal, S. et al. (1993) "*A Single Amino Acid Substitution Abolishes The Heterogeneity Of Chimeric Mouse/Human (Igg4) Antibody*," Molec. Immunol. 30(1):105-108; Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells*," Mol. Immun. 34(6): 441-452; and U.S. Pat. No. 6,982,323. In some embodiments the IgG1 and/or IgG2 domain is modified; for example, Angal, S. et al. (1993) describe IgG1 and IgG2 variants in which serine 241 is replaced with proline.

In a preferred embodiment, the Fc domain of such molecules contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890. Exemplary variants of human IgG1 Fc domains with reduced binding to CD32B and/or increased binding to CD16A contain F243L, R929P, Y300L, V305I or P296L substitutions. These amino acid substitutions can be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

Techniques for conjugating therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; and Thorpe et al. (1982) "*The Preparation And Cytotoxic Properties Of Antibody-Toxin Conjugates*," Immunol. Rev. 62:119-158.

Any of the disclosed molecules can be fused to marker sequences, such as a peptide, to facilitate purification. In preferred embodiments, the marker amino acid sequence is a hexa-histidine peptide, the hemagglutinin "HA" tag, which corresponds to an epitope derived from the influenza hemagglutinin protein (Wilson, I. A. et al. (1984) "*The Structure Of An Antigenic Determinant In A Protein,*" Cell, 37:767-778) and the "flag" tag (Knappik, A. et al. (1994) "*An Improved Affinity Tag Based On The FLAG Peptide For The Detection And Purification Of Recombinant Antibody Fragments*," Biotechniques 17(4):754-761).

The disclosed B7-H4 binding molecules can be conjugated to a diagnostic or therapeutic agent, or another molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen or to select patients more likely to respond to a particular therapy (such as those with high levels of infiltrating TAMs, and especially those expressing high levels of B7-H4).

In particular, most cancers in humans grow as solid tumors composed of cancer cells intertwined with a supporting group of structures (stroma) that are required for the survival, growth and progression of the tumor. The major components in tumor stroma are fibroblasts, neovasculature and immune cells, including macrophages. Such tumor-associated macrophages are not only one of the most important components of the tumor stroma, but include the antigen presenting cells (APC) that are critical for initiating and maintaining tumor-associated antigen (TAA)-specific T cell immunity.

Tumor environmental macrophages markedly outnumber the other APCs, such as dendritic cells (DCs), that are present within tumors, and represent a prominent subpopulation of APCs in solid tumors (Kryczek, I. et al. (2006) "*B7-H4 Expression Identifies A Novel Suppressive Macrophage Population In Human Ovarian Carcinoma,*" J. Exper. Med. 203(4):871-881). Tumor environmental macrophages that are B7-H4$^+$ significantly suppress T cell activation. B7-H4$^-$ macrophages can be converted into B7-H4$^+$ macrophages by IL-10 and IL-6 in vitro (Kryczek, I. et al. (2006) "*Cutting Edge: Induction Of B7-H4 On APCs Through IL-10: Novel Suppressive Mode For Regulatory T Cells,*" J. Immunol. 177(1):40-44). Since high levels of IL-10 and IL-6 are found in the ovarian tumor environment, the ability of such cytokines to induce B7-H4 expression is considered to be relevant to the increased suppression of T cell activation seen in aggressive tumors. Importantly, such suppressive activity can be reduced by GM-CSF or IL-4, two dendritic cell differentiation cytokines, which act to block B7-H4 expression. Such suppressive activity can also be reduced by blocking B7-H4 activity with the disclosed compositions.

Although the phenotype and the role in tumor immunity played by dendritic cells has been investigated, such studies have not elucidated the roles played by B7-H4$^+$ and B7-H4$^-$ macrophages within the tumor environment of patients with cancer. The disclosed B7-H4 binding molecules have use in elucidating the roles played by B7-H4$^+$ and B7-H4$^-$ macrophages and as a means for evaluating the clinical prognosis of tumors in patients (i.e., the extent of B7-H4$^+$ macrophages to total macrophages correlates with tumor aggressiveness and the severity of cancer). Such evaluations are particularly useful in conjunction with determinations of the extent of B7-H1$^+$ macrophages to total macrophages, since tumor B7-H1 expression and positive tumor B7-H4 expression are independently associated with death from cancer (Krambeck, A. E. et al. (2006) "*B7-H4 Expression In Renal Cell Carcinoma And Tumor Vasculature: Associations With Cancer Progression And Survival,*" Proc. Natl. Acad. Sci. (U.S.A.) 103(2): 10391-10396).

Detection can be facilitated by coupling the molecule, such as antibody or an antigen binding fragment thereof, to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance can be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium) ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La) lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re) rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn,) tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

The disclosed molecules can be attached to solid supports, which are particularly useful for immunoassays or purification of the target antigen or of other molecules that are capable of binding to target antigen that has been immobilized to the support via binding to an antibody or antigen-binding fragment. Such solid supports include, but are not limited to, glass, cellulose, polyacrylamide, nylon, polystyrene, polyvinyl chloride or polypropylene.

Nucleic acid molecules (DNA or RNA) that encode any such antibodies, fusion proteins or fragments, as well as vector molecules (such as plasmids) that are capable of transmitting or of replicating such nucleic acid molecules are also disclosed. The nucleic acids can be single-stranded, double-stranded, can contain both single-stranded and double-stranded portions.

A. Murine Anti-Human B7-H4 Antibody 6H3 and its CDRs

The disclosed murine anti-human B7-H4 antibody 6H3, possesses the ability to modulate an activity of human B7-H4 arrayed on the surface of a human cell (especially when such B7-H4 is expressed at an endogenous concentration). The term "endogenous concentration" refers to the level at which a molecule is natively expressed (i.e., in the absence of expression vectors or recombinant promoters) by a cell (which cell can be a normal cell, a cancer cell or an infected cell).

In one embodiment, such modulation will be caused by the binding of such antibodies to B7-H4 (preferably as endogenously expressed and arrayed). In an alternative embodiment, such modulation will include enhancing or otherwise facilitating the binding of endogenously expressed and arrayed B7-H4

DNA encoding murine anti-human B7-H4 antibody 6H3 was sequenced. The amino acid sequences and encoding polynucleotide sequences of the variable domains of the light and heavy chains are as indicated below. CDR sequences are shown in bold and underlined:

```
Anti-Human B7-H4 Clone 6H3 Light Chain Variable
Region:
                                       (SEQ ID NO: 3)
DVVMTQTPLS LPVSLGDQAS ISCRSSQSLV HINGNTYLHW
YLQKPGQSPK

VLIYKVSNRF SGVPDRFSGS GSGTDFTLKI SRVEAEDLGV
YFCSQSTHVP

LTFGAGTKLE LK

Polynucleotide Encoding the Light Chain Variable
Region:
                                       (SEQ ID NO: 4)
gatgttgtga tgacccaaac tcctctctcc ctgcctgtca
gtcttggaga tcaagcctcc atctcttgca gatctagtca gagccttgta
cacattaatg
```

-continued

```
gaaacaccta tttacattgg tacctgcaga agccaggcca
gtctccaaag gtcctgatct acaaagtttc caaccgattt tctggggtcc
cagacaggtt cagtggcagt ggatcaggga cagatttcac actcaagatc
agcagagtgg aggctgagga tctgggagtt tatttctgct ctcaaagtac
acatgttccg ctcacgttcg gtgctgggac caagctggag ctgaaac
```

Heavy Chain Variable Region:
(SEQ ID NO: 5)
EVQLQQSGPV LVKPGTSVKM SCKASGYTFT DYYMNWVKQS HGKSLEWIGV

INPYNGDTTY NQKFKGKATL TVDKSSSTAY MEVNSLTFED SAVYYCARYP

ESTYWGQGTL VTVSA

Polynucleotide Encoding the Light Chain Variable Region:
(SEQ ID NO: 6)
```
gaggtccagc tgcaacagtc tggacctgta ctggtgaagc
ctgggacttc agtgaagatg tcctgtaagg cttctggata cacattcact
gactactata tgaactgggt gaagcagagc catggaaaga gtcttgagtg
gattggagtt attaatcctt acaacggtga cactacctac aaccagaagt
tcaagggcaa ggccacattg actgttgaca agtcctccag cacagcctac
atggaggtca acagcctgac atttgaggac tctgcagtct attactgtgc
aagatacccg gagagtactt actggggcca agggactctg gtcactgtct
ctgca
```

Figure 1B:
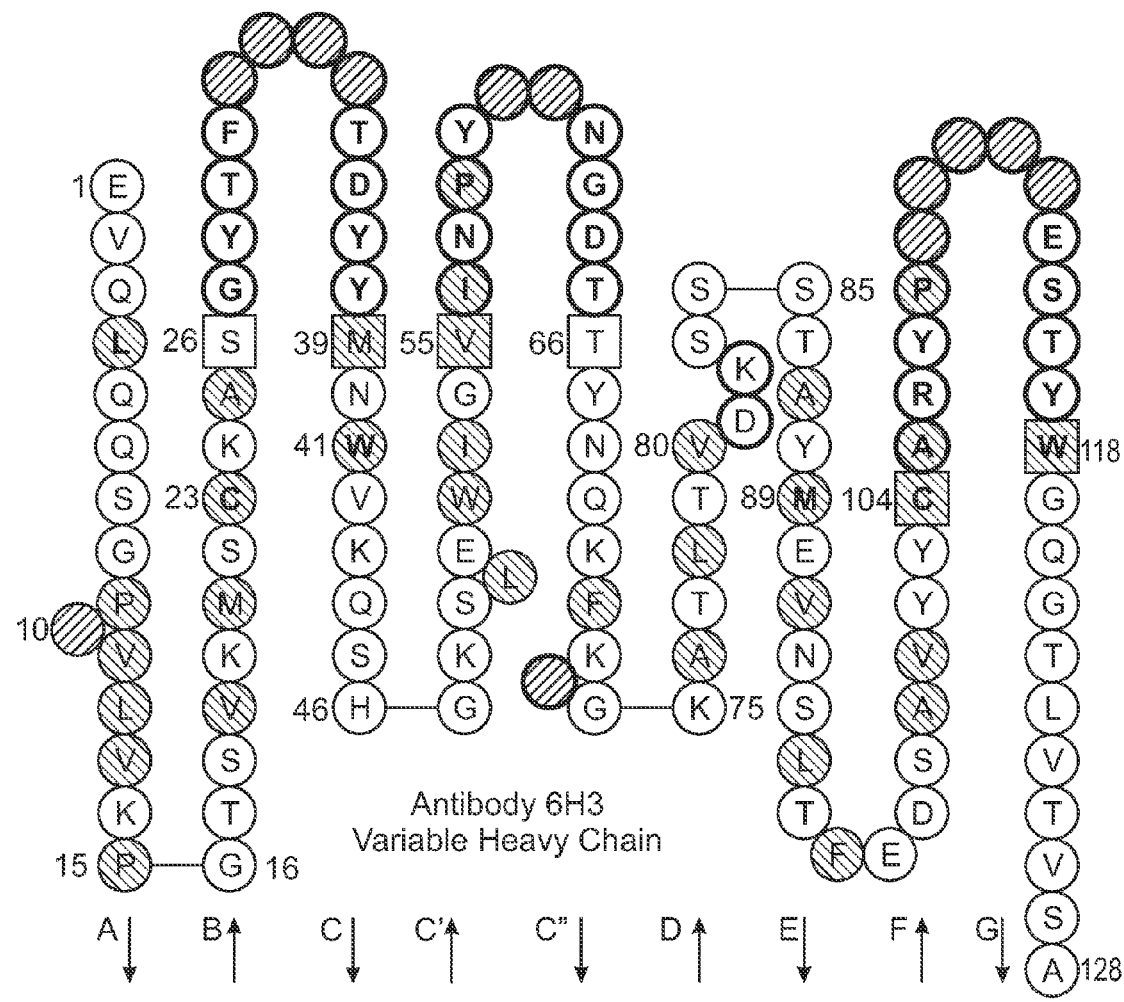

Using the criteria of Chothia and Lesk, light chain CDR1 was concluded to have a Class 4 canonical structure; light chain CDR2 and CDR3 and heavy chain CDR1 were concluded to have Class 1 canonical structures; heavy chain CDR2 was concluded to have a Class 2 canonical structure (Chothia, C. et al. (1987) "*Canonical Structures For The Hypervariable Regions Of Immunoglobulins,*" J. Mol. Biol. 196:901-917). Collier de Perles is a 2D representation of variable domains and provides information on the amino acid positions in beta-strands and loops in the variable domains (Ruiz, M. et al. (2002) "*IMGT Gene Identification And Colliers de Perles Of Human Immunoglobulins With Known 3D Structures,*" Immunogenetics 53(10-11):857-883). Collier de Perles of the murine 6H3 antibody light chain and heavy chain variable regions are shown in FIG. 1A and FIG. 1B, respectively. The three CDR loops of the chains are shown at the top of the diagrams. There are no free Cys residues or N-linked glycosylation sites in the variable light or heavy chain regions.

B. Humanized Variants of Anti-Human B7-H4 Antibody 6H3

The disclosed humanized variants of murine anti-human B7-H4 antibody 6H3, and their antigen-binding derivatives typically include immunospecific or physiospecific B7-H4-binding molecules can have substantially the same, or the same, binding characteristics as murine anti-human B7-H4 antibody 6H3. For example, they can possess the ability to modulate an activity of human B7-H4 arrayed on the surface of a human cell (especially when such B7-H4 is expressed at an endogenous concentration).

Multiple preferred light and heavy chain humanized derivatives of anti-human B7-H4 antibody 6H3 were prepared. The amino acid sequences of the Light Chain Variable Region of preferred humanized variants, derived from the IGKV2-30*02 IGKJ4*01 acceptor framework are shown below (CDRs are shown underlined):

1. VL1A IGKV2-30*02 IGKJ4*01 (Humanized 1):
(SEQ ID NO: 18)
DVVMTQSPLS LPVTLGQPAS ISCRSSQSLV HINGNTYLNW FQQRPGQSPR

RLIYKVSNRD SGVPDRFSGS GSGTDFTLKI SRVEAEDVGV YYCSQSTHVP

LTFGGGTKVE IK

2. VL1B IGKV2-30*02 IGKJ4*01 (Humanized 2):
(SEQ ID NO: 19)
DVVMTQSPLS LPVTLGQPAS ISCRSSQSLV HINGNTYLHW YQQRPGQSPR

VLIYKVSNRF SGVPDRFSGS GSGTDFTLKI SRVEAEDVGV YFCSQSTHVP

LTFGGGTKVE IK

3. VL1C IGKV2-30*02 IGKJ4*01 (Humanized 3):
(SEQ ID NO: 20)
DVVMTQSPLS LPVTLGQPAS ISCRSSQSLV HINGNTYLHW YLQRPGQSPK

VLIYKVSNRF SGVPDRFSGS GSGTDFTLKI SRVEAEDVGV YFCSQSTHVP

LTFGGGTKVE IK

The amino acid sequences of the Light Chain Variable Region of preferred humanized variants of anti-human B7-H4 antibody 6H3, derived from the CAA85590 acceptor framework are shown below (CDRs are shown underlined):

1. VL2A CAA85590 (Humanized 1):
(SEQ ID NO: 21)
DIVMTQTPLS LPVTLGQPAS ISCRSSQSLV HINGNTYLNW FQQRPGQSPR

RLIYKVSNRD SGVPDRFSGS GSGADFTLKI SRVEAEDVGV YYCSQSTHVP

LTFGQGTKVE IK

2. VL2B CAA85590 (Humanized 2):
(SEQ ID NO: 22)
DIVMTQTPLS LPVTLGQPAS ISCRSSQSLV HINGNTYLHW YQQRPGQSPR

VLIYKVSNRF SGVPDRFSGS GSGTDFTLKI SRVEAEDVGV YFCSQSTHVP

LTFGQGTKVE IK

3. VL2C CAA85590 (Humanized 3):
(SEQ ID NO: 23)
DIVMTQTPLS LPVTLGQPAS ISCRSSQSLV HINGNTYLHW YLQRPGQSPK

VLIYKVSNRF SGVPDRFSGS GSGTDFTLKI SRVEAEDVGV YFCSQSTHVP

LTFGAGTKVE IK

The amino acid sequences of the Heavy Chain Variable Region of preferred humanized variants of anti-human B7-H4 antibody 6H3, derived from the IGHV1-46*03 IGHJ4*01 acceptor framework are shown below (CDRs are shown underlined):

```
1. VH1A IGHV1-46*03 IGHJ4*01 (Humanized 1):
                                   (SEQ ID NO: 24)
QVQLVQSGAE VKKPGASVKV SCKASGYTFT DYYMHWVRQA
PGQGLEWMGI

INPYNGDTSY AQKFQGRVTM TRDTSTSTVY MELSSLRSED
TAVYYCARYP

ESTYWGQGTL VTVSS

2. VH1B IGHV1-46*03 IGHJ4*01 (Humanized 2):
                                   (SEQ ID NO: 25)
EVQLVQSGAE VKKPGASVKV SCKASGYTFT DYYMNWVRQA
PGQGLEWMGI

INPYNGDTSY NQKFQGRVTL TVDKSTSTVY MELSSLRSED
TAVYYCARYP

ESTYWGQGTL VTVSS

3. VH1C IGHV1-46*03 IGHJ4*01 (Humanized 3):
                                   (SEQ ID NO: 26)
EVQLVQSGAE VKKPGASVKV SCKASGYTFT DYYMNWVRQA
PGQGLEWIGI

INPYNGDTSY NQKFKGRVTL TVDKSTSTAY MELSSLRSED
TAVYYCARYP

ESTYWGQGTL VTVSS
```

Amino Acid Sequences of the Heavy Chain Variable Region of preferred humanized variants of anti-human B7-H4 antibody 6H3, derived from the ABF83259 acceptor framework are shown below (CDRs are shown underlined):

```
1. VH2A ABF83259 (Humanized 1):
                                   (SEQ ID NO: 27)
QVQLVQSGAE MKKPGASVKV SCKASGYTFT DYYIHWVRQA
PGQSLEWMGW

INPYNGDTKY SQKFQGRVTV ARDTSATTAY MELSSLRSED
TAVYYCARYP

ESTYWGQGTL VTVSS

2. VH2B ABF83259 (Humanized 2):
                                   (SEQ ID NO: 28)
EVQLVQSGAE MKKPGASVKV SCKASGYTFT DYYMNWVRQA
PGQSLEWMGV

INPYNGDTTY NQKFQGRVTV AVDKSATTAY MELSSLRSED
TAVYYCARYP

ESTYWGQGTL VTVSS

3. VH2C ABF83259 (Humanized 3):
                                   (SEQ ID NO: 29)
EVQLVQSGAE MKKPGASVKV SCKASGYTFT DYYMNWVRQA
PGQSLEWIGV

INPYNGDTTY NQKFQGRVTV TVDKSATTAY MELSSLRSED
TAVYYCARYP

ESTYWGQGTL VTVSS
```

Antibodies, and their antigen-binding fragments that include any of the 36 combinations of the disclosed humanized variants of anti-human B7-H4 antibody 6H3 are provided. Specifically, such antibodies include the humanized variant combinations shown in Table 1:

TABLE 1

Humanized Variants of anti-B7-H4 Antibody 6H3

| Humanized Variant No. | Light Chain | SEQ ID NO. | Heavy Chain | SEQ ID NO. |
|---|---|---|---|---|
| H1 | VL1A IGKV2-30*02 IGKJ4*01 (Humanized 1) | 18 | VH1A IGHV1-46*03 IGHJ4*01 (Humanized 1) | 24 |
| H2 | VL1A IGKV2-30*02 IGKJ4*01 (Humanized 1) | 18 | VH1B IGHV1-46*03 IGHJ4*01 (Humanized 2) | 25 |
| H3 | VL1A IGKV2-30*02 IGKJ4*01 (Humanized 1) | 18 | VH1C IGHV1-46*03 IGHJ4*01 (Humanized 3) | 26 |
| H4 | VL1A IGKV2-30*02 IGKJ4*01 (Humanized 1) | 18 | VH2A ABF83259 (Humanized 1) | 27 |
| H5 | VL1A IGKV2-30*02 IGKJ4*01 (Humanized 1) | 18 | VH2B ABF83259 (Humanized 2) | 28 |
| H6 | VL1A IGKV2-30*02 IGKJ4*01 (Humanized 1) | 18 | VH2C ABF83259 (Humanized 3) | 29 |
| H7 | VL1B IGKV2-30*02 IGKJ4*01 (Humanized 2) | 19 | VH1A IGHV1-46*03 IGHJ4*01 (Humanized 1) | 24 |
| H8 | VL1B IGKV2-30*02 IGKJ4*01 (Humanized 2) | 19 | VH1B IGHV1-46*03 IGHJ4*01 (Humanized 2) | 25 |
| H9 | VL1B IGKV2-30*02 IGKJ4*01 (Humanized 2) | 19 | VH1C IGHV1-46*03 IGHJ4*01 (Humanized 3) | 26 |
| H10 | VL1B IGKV2-30*02 IGKJ4*01 (Humanized 2) | 19 | VH2A ABF83259 (Humanized 1) | 27 |
| H11 | VL1B IGKV2-30*02 IGKJ4*01 (Humanized 2) | 19 | VH2B ABF83259 (Humanized 2) | 28 |
| H12 | VL1B IGKV2-30*02 IGKJ4*01 (Humanized 2) | 19 | VH2C ABF83259 (Humanized 3) | 29 |
| H13 | VL1C IGKV2-30*02 IGKJ4*01 (Humanized 3) | 20 | VH1A IGHV1-46*03 IGHJ4*01 (Humanized 1) | 24 |
| H14 | VL1C IGKV2-30*02 IGKJ4*01 (Humanized 3) | 20 | VH1B IGHV1-46*03 IGHJ4*01 (Humanized 2) | 25 |
| H15 | VL1C IGKV2-30*02 IGKJ4*01 (Humanized 3) | 20 | VH1C IGHV1-46*03 IGHJ4*01 (Humanized 3) | 26 |
| H16 | VL1C IGKV2-30*02 IGKJ4*01 (Humanized 3) | 20 | VH2A ABF83259 (Humanized 1) | 27 |
| H17 | VL1C IGKV2-30*02 IGKJ4*01 (Humanized 3) | 20 | VH2B ABF83259 (Humanized 2) | 28 |
| H18 | VL1C IGKV2-30*02 IGKJ4*01 (Humanized 3) | 20 | VH2C ABF83259 (Humanized 3) | 29 |
| H19 | VL2A CAA85590 (Humanized 1) | 21 | VH1A IGHV1-46*03 IGHJ4*01 (Humanized 1) | 24 |
| H20 | VL2A CAA85590 (Humanized 1) | 21 | VH1B IGHV1-46*03 IGHJ4*01 (Humanized 2) | 25 |
| H21 | VL2A CAA85590 (Humanized 1) | 21 | VH1C IGHV1-46*03 IGHJ4*01 (Humanized 3) | 26 |
| H22 | VL2A CAA85590 (Humanized 1) | 21 | VH2A ABF83259 (Humanized 1) | 27 |
| H23 | VL2A CAA85590 (Humanized 1) | 21 | VH2B ABF83259 (Humanized 2) | 28 |
| H24 | VL2A CAA85590 (Humanized 1) | 21 | VH2C ABF83259 (Humanized 3) | 29 |
| H25 | VL2B CAA85590 (Humanized 2) | 22 | VH1A IGHV1-46*03 IGHJ4*01 (Humanized 1) | 24 |
| H26 | VL2B CAA85590 (Humanized 2) | 22 | VH1B IGHV1-46*03 IGHJ4*01 (Humanized 2) | 25 |
| H27 | VL2B CAA85590 (Humanized 2) | 22 | VH1C IGHV1-46*03 IGHJ4*01 (Humanized 3) | 26 |
| H28 | VL2B CAA85590 (Humanized 2) | 22 | VH2A ABF83259 (Humanized 1) | 27 |
| H29 | VL2B CAA85590 (Humanized 2) | 22 | VH2B ABF83259 (Humanized 2) | 28 |
| H30 | VL2B CAA85590 (Humanized 2) | 22 | VH2C ABF83259 (Humanized 3) | 29 |
| H31 | VL2C CAA85590 (Humanized 3) | 23 | VH1A IGHV1-46*03 IGHJ4*01 (Humanized 1) | 24 |
| H32 | VL2C CAA85590 (Humanized 3) | 23 | VH1B IGHV1-46*03 IGHJ4*01 (Humanized 2) | 25 |
| H33 | VL2C CAA85590 (Humanized 3) | 23 | VH1C IGHV1-46*03 IGHJ4*01 (Humanized 3) | 26 |
| H34 | VL2C CAA85590 (Humanized 3) | 23 | VH2A ABF83259 (Humanized 1) | 27 |

TABLE 1-continued

Humanized Variants of anti-B7-H4 Antibody 6H3

| Humanized Variant No. | Light Chain | SEQ ID NO. | Heavy Chain | SEQ ID NO. |
|---|---|---|---|---|
| H35 | VL2C CAA85590 (Humanized 3) | 23 | VH2B ABF83259 (Humanized 2) | 28 |
| H36 | VL2C CAA85590 (Humanized 3) | 23 | VH2C ABF83259 (Humanized 3) | 29 |

The antibodies or fragments thereof can include an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the antibody produced by any of the above clones, and which exhibit immunospecific binding to human B7-H4. The antibodies or fragments thereof can include a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the above-listed clones and which exhibit immunospecific binding to B7-H4. The determination of percent identity of two amino acid sequences can be determined by BLAST protein comparison.

The molecule can be an immunoglobulin molecule (e.g., an antibody, diabody, fusion protein, etc.) that includes one, two or three light chain CDRs and one, two or three heavy chain CDRs (most preferably three light chain CDRs and three heavy chain CDRs), wherein the light chain CDRs include:

(1) the light chain CDR1 of murine anti-human B7-H4 antibody 6H3, or a humanized variant thereof;

(2) the light chain CDR2 of murine anti-human B7-H4 antibody 6H3, or a humanized variant thereof;

(3) the light chain CDR3 of murine anti-human B7-H4 antibody 6H3, or a humanized variant thereof;

(4) the light chain CDR1 and the light chain CDR2 of mouse anti-human B7-H4 antibody 6H3, or a humanized variant thereof;

(5) the light chain CDR1 and the light chain CDR3 of mouse anti-human B7-H4 antibody 6H3, or a humanized variant thereof;

(6) the light chain CDR2 and the light chain CDR3 of mouse anti-human B7-H4 antibody 6H3, or a humanized variant thereof;

or (7) the light chain CDR1, the light chain CDR2 and the light chain CDR3 mouse of anti-human B7-H4 antibody 6H3, or humanized variant thereof.

The molecule can be an immunoglobulin molecule includes one, two or three light chain CDRs and one, two or three heavy chain CDRs (most preferably three light chain CDRs and three heavy chain CDRs), wherein the heavy chain CDRs include:

(1) the heavy chain CDR1 of murine anti-human B7-H4 antibody 6H3, or a humanized variant thereof;

(2) the heavy chain CDR2 of murine anti-human B7-H4 antibody 6H3, or a humanized variant thereof;

(3) the heavy chain CDR3 of murine anti-human B7-H4 antibody 6H3, or a humanized variant thereof;

(4) the heavy chain CDR1 and the heavy chain CDR2 of murine anti-human B7-H4 antibody 6H3, or a humanized variant thereof;

(5) the heavy chain CDR1 and the heavy chain CDR3 of murine anti-human B7-H4 antibody 6H3, or a humanized variant thereof;

(6) the heavy chain CDR2 and the heavy chain CDR3 of murine anti-human B7-H4 antibody 6H3, or a humanized variant thereof;

or (7) the heavy chain CDR1, the heavy chain CDR2 and the heavy chain CDR3 murine anti-human B7-H4 antibody 6H3, or a humanized variant thereof.

The molecule can be an immunoglobulin molecule that includes one, two or three light chain CDRs and one, two or three heavy chain CDRs (most preferably three light chain CDRs and three heavy chain CDRs), wherein the light chain CDRs include:

(1) the light chain CDR1 of murine anti-human B7-H4 antibody 6H3, or a humanized variant thereof;

(2) the light chain CDR2 of murine anti-human B7-H4 antibody 6H3, or a humanized variant thereof;

(3) the light chain CDR3 of murine anti-human B7-H4 antibody 6H3, or a humanized variant thereof;

(4) the light chain CDR1 and the light chain CDR2 of murine anti-human B7-H4 antibody 6H3, or a humanized variant thereof;

(5) the light chain CDR1 and the light chain CDR3 of murine anti-human B7-H4 antibody 6H3, or a humanized variant thereof;

(6) the light chain CDR2 and the light chain CDR3 of murine anti-human B7-H4 antibody 6H3, or a humanized variant thereof;

or (7) the light chain CDR1, the light chain CDR2 and the light chain CDR3 of murine anti-human B7-H4 antibody 6H3, or a humanized variant thereof, and wherein the heavy chain CDRs include:

(1) the heavy chain CDR1 of murine anti-human B7-H4 antibody 6H3, or a humanized variant thereof;

(2) the heavy chain CDR2 of murine anti-human B7-H4 antibody 6H3, or a humanized variant thereof;

(3) the heavy chain CDR3 of murine anti-human B7-H4 antibody 6H3, or a humanized variant thereof;

(4) the heavy chain CDR1 and the heavy chain CDR2 of murine anti-human B7-H4 antibody 6H3, or a humanized variant thereof;

(5) the heavy chain CDR1 and the heavy chain CDR3 of murine anti-human B7-H4 antibody 6H3, or a humanized variant thereof;

(6) the heavy chain CDR2 and the heavy chain CDR3 of murine anti-human B7-H4 antibody 6H3, or a humanized variant thereof;

or (7) the heavy chain CDR1, the heavy chain CDR2 and the heavy chain CDR3 of murine anti-human B7-H4 antibody 6H3, or a humanized variant thereof.

For example, the antibody can have the CDRs of murine 6H, or a chimeric antibody thereof, or a humanized variant having CDRs corresponding to the CDRs of anti-human B7-H4 antibody 6H3.

In a specific embodiment, an antibody or an antigen-binding fragment thereof includes one, two, three, four, five, or more preferably, all 6 CDRs of the humanized variants of anti-human B7-H4 antibody 6H3 and will exhibit the same ability to bind to human B7-H4 as antibody 6H3.

C. Therapeutic and Prophylactic Uses

Typically, the disclosed antibodies immunospecifically bind to B7-H4 in a recipient subject. As used herein, a "subject" is preferably a mammal such as a non-primate (e.g., cows, pigs, horses, cats, dogs, rats, etc.) or a primate (e.g., monkey and human), and most preferably a human. In preferred embodiments, the antibodies are humanized antibodies, or antigen-binding fragments thereof, that immunospecifically bind to human B7-H4.

In some embodiments, such molecules are capable of depleting B7-H4-expressing tumor cells or TAMs in a recipient human or in human tissue (in situ or ex vivo) or of modulating the activity of such cells. Depletion of B7-H4 positive tumor cells or TAMs or a beneficial reduction in B7-H4 levels can be monitored by IHC of tumor tissues using the disclosed anti-B7-H4 antibodies or another tumor-specific or TAM-specific marker, or a reduction in B7-H4 mRNA levels by PCR, in-situ hybridization or another other method known to one skilled in the art. Patients likely to benefit from treatment with an anti-B7-H4 antibody will express the target B7-H4 protein, either on tumor or TAMs, and this can be assessed by IHC of tumor samples, FACs, in-situ hybridization or another other method known to one skilled in the art.

As used herein, the terms "treat," "treating," "treatment" and "therapeutic use" refer to the elimination, reduction or amelioration of one or more symptoms of a disease or disorder exacerbated by the interactions of B7-H4 with its receptor(s), or by the expression of B7-H4 or its presence arrayed on the surface of a cell. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount can refer to the amount of therapeutic agent sufficient to delay or minimize the onset of disease, e.g., delay or minimize the spread of cancer. A therapeutically effective amount can also refer to the amount of the therapeutic agent that provides a therapeutic benefit in the treatment or management of a disease. Further, a therapeutically effective amount with respect to a therapeutic agent means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount can also refer to the amount of the prophylactic agent that provides a prophylactic benefit in the prevention of disease. Further, a prophylactically effective amount with respect to a prophylactic agent means that amount of prophylactic agent alone, or in combination with other agents, that provides a prophylactic benefit in the prevention of disease.

1. Uses of Up-Modulators of the Immune System

In a preferred embodiment, the disclosed B7-H4 binding molecules bind to B7-H4 to "substantially" disrupt (i.e., impair, prevent, or attenuate) binding between B7-H4 and its receptor(s) (for example, by binding at one or more sites proximal to and disruptive of the binding site of B7-H4 and its receptor, or at a region whose conformation is disrupted by such binding and thus becomes impaired in its ability to bind to receptor, etc.). As discussed above, interactions between B7-H4 and its receptor inhibit the proliferation of T cells and reduce inflammation, including the production of multiple cytokines (Zang, X. et al. (2003) *B7x: A Widely Expressed B7 Family Member That Inhibits T Cell Activation,*" Proc. Natl. Acad. Sci. (USA) 100:10388-10392; Prasad, D. V. et al. (2003) *B7S1, A Novel B7 Family Member That Negatively Regulates T Cell Activation,*" Immunity 18:863-873). Thus, in a preferred embodiment, the administration of such molecules to a subject up-modulates immune responses of the subject by antagonizing normal B7-H4 binding to its receptor.

Up-modulation of the immune system is particularly desirable in the treatment of cancers and chronic infections, and thus the compositions disclosed herein can be used in the treatment of such disorders. B7-H4 is over-expressed upon HIV infection (Carter, C. A. et al. (2008) *"Cell Biology Of HIV-*1 *Infection Of Macrophages,*" Ann. Rev. Microbiol. 62:425-443; Noursadeghi, M. et al. (2006) *"HIV-*1 *Infection Of Mononuclear Phagocytic Cells: The Case For Bacterial Innate Immune Deficiency In AIDS,*" Lancet Infect. Dis. 6:794-804). Hence, the disclosed anti-B7-H4 antibodies have particular use as therapeutics for HIV infection and AIDS treatment. As used herein, the term "cancer" refers to a neoplasm or tumor resulting from abnormal uncontrolled growth of cells. As used herein, cancer explicitly includes, leukemias and lymphomas. The term refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation. Non-cancer cells do not form colonies in soft agar and form distinct sphere-like structures in three-dimensional basement membrane or extracellular matrix preparations.

It is believed that the expression of B7-H4 represents a mechanism of downregulating antitumor immunity, particularly T-cell response, at the level of the effector cells. Therefore, blocking B7-H4 mediated signal transduction, particularly B7-H4 expressed on the surface of cancers cells or tumor-associated macrophage, particularly in the tumor microenvironment, can used to increase an antitumor immune response and reduce one or more symptoms of the cancer. Methods of treating cancers, including cancers characterized by increased expression of cell-free B7-H4, typically include administering a subject in need thereof an antagonist of transmembrane B7-H4 or its receptor, or a combination thereof, in an effective amount to reduce B7-H4 mediated signal transduction, tumor associated macrophage-dependent B7-H4 mediated signal transduction, or tumor-dependent B7-H4 mediated signal transduction.

Suitable antagonists of B7-H4-mediated signaling, including the antibodies disclosed herein, for use in the treatment of cancer are discussed above. A method of treating cancer can include administering to the subject an antibody that binds to transmembrane B7-H4 and prevents, reduces, blocks, or inhibits transmembrane B7-H4 mediated immunosupression. In a preferred embodiment, the antibody binds to the IgC domain of B7-H4. In some embodiments, the antibody causes B7-H4 internalization, resulting in reduced availability of transmembrane B7-H4 on the cell surface and decreased transmembrane B7-H4 mediated immune suppression. It is believed that internalized B7-H4 is directed into acidic lysosomal compartment, where it is degraded and therefore no longer effective to mediate immune suppressive signal transduction. Such a method can also be used to treat bacterial, viral, and other infections that evade the body's immune response against the infection by B7-H4-mediated immune suppression.

In some embodiments the antibody is conjugated to an active agent. The active agent can be, for example, a cytotoxic agent such as a chemotherapeutic drug, or radioactive isotype. Upon binding to transmembrane B7-H4 the antibody and its cytotoxic payload can be internalized by the target cell. In this way, the antibody-drug conjugate can carry out selective destruction of the target cells. Suitable drug conjugates as well as methods of making and using antibody-drug conjugates in the treatment of immune disorders and cancer are known in the art. See for example, U.S. Published Application No. 2012/0288512, which describes anti-CD70-drug conjugates, is specifically incorporated by reference in its entirety.

Target cells include, but are not limited to, cells expressing B7-H4, for example, transformed cells that typically do not express B7-H4 when they are not transformed, or cells characterized by increased expression compared to control cells. Preferred target cells include cancer cells and tumor associated macrophages. In some embodiments, the composition is administered directly to the tumor or the tumor microenvironment to enhance localization of the composition to the tumor site and reduce toxicity to non-target cells expressing B7-H4.

In some embodiments, an antibody that binds to the IgC domain is co-administered in combination with an antibody that binds the IgV domain.

B7-H4-specific active agents can be administered alone, or in combination with conventional cancer therapies, for example, chemotherapy, radiotherapy, and surgery.

Cancers and related disorders that can be treated or prevented by the disclosed methods and compositions include, but are not limited to, the following: leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete*

*Book of Cancer Diagnosis, Treatment, and Recovery*, Viking Penguin, Penguin Books U.S.A., Inc., United States of America).

Accordingly, the disclosed methods and compositions are also useful in the treatment or prevention of a variety of cancers (particularly, ovarian, breast, prostate, gastric, renal, thyroid, and uterine cancer) or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions disclosed herein. Such cancers can include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the disclosed methods and compositions in the ovary, bladder, breast, colon, lung, skin, pancreas, or uterus. In other specific embodiments, sarcoma, melanoma, or leukemia is treated or prevented by the methods and compositions provided.

Cancer cells acquire a characteristic set of functional capabilities during their development, albeit through various mechanisms. Such capabilities include evading apoptosis, self-sufficiency in growth signals, insensitivity to antigrowth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

Similar to its application to tumors as discussed above, the antibodies and antigen-binding fragments can be used alone, or as an adjuvant, in combination with vaccines or with antimibrobial agents, to stimulate the immune response against toxins or self-antigens or against pathogens (e.g., viruses, such as HIV, HTLV, hepatitis virus, influenza virus, respiratory syncytial virus, vaccinia virus, rabies virus; bacteria, such as those of *Mycobacteria, Staphylococci, Streptococci, Pneumonococci, Meningococci, Gonococci, Klebsiella, Proteus, Serratia, Pseudomonas, Legionella, Corynebacteria, Salmonella, Vibrio, Clostridia, Bacilli, Pasteurella, Leptospirosis, Bordatella*, and particularly such pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus *Mucorales* (*mucor, absidia, rhizophus*), *Sporothrix* (*schenkii*), *Blastomyces* (*dermatitidis*), *Paracoccidioides* (*brasiliensis*), *Coccidioides* (*immitis*) and *Histoplasma* (*capsulatum*), *Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi*, etc.), *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia*, or *Trypanosoma*, etc. Thus, the antibodies and antigen-binding fragments can be used in the treatment of infectious disease.

As indicated above, a particularly preferred use of the disclosed antibodies and antigen-binding fragments is to bind to and preferably substantially block tumor cells or TAMs so as to modulate their immune suppressive activity. Furthermore, such antibodies can be used to deplete B7-H4 expressing tumor cells or TAMs within the tumor microenvironment, or deplete their concentration of TAMs in peripheral blood. In one embodiment such modulation or depletion is accomplished using anti-B7-H4 antibodies that bind to a site so as to impair or disrupt normal B7-H4 function. As a consequence of such disruption, TAMs activity is decreased (modulated), and/or the actual or effective (functional) concentration of macrophages in the tumor is depleted. Alternatively, such modulation or depletion is accomplished using anti-B7-H4 antibodies that are conjugated to a toxin, such that their binding to a tumor cell or TAM leads to the death of the tumor cell or macrophage. Preferably, in either embodiment, the sequence of the Fc region of the antibody will have been deleted (for example, an Fab or F(ab)$_2$, etc.) or modified so that the molecule will exhibit diminished or no Fc receptor (FcR) binding activity, or will exhibit enhanced antibody-dependent cell-mediated cytotoxicity (ADCC) or complement dependent cytotoxicity (CDC) activities. Antibodies, whose Fc regions exhibit diminished or no Fc receptor binding activity, will preferentially work as a blocker that prevents B7-H4 on the tumor or TAMs from interacting with inhibitory receptor(s) on T cells in the tumor microenvironment. On the other hand, the use of antibodies having Fc regions that exhibit enhanced induction of ADCC or CDC will preferentially be used to cause depletion of the tumor cells or TAMs expressing B7-H4.

2. Uses of Down-Modulators of the Immune System

The anti-B7-H4 antibodies can be employed to produce anti-idiotypic peptides or antibodies (Wallmann, J. et al. (2010) *"Anti-Ids in Allergy: Timeliness of a Classic Concept,"* World Allergy Organiz. J. 3(6):195-201; Nardi, M. et al. (2000) *"Antiidiotype Antibody Against Platelet Anti-GpIIIa Contributes To The Regulation Of Thrombocytopenia In HIV-1-ITP Patients,"* J. Exp. Med. 191(12):2093-2100) or mimetics (Zang, Y. C. et al. (2003) *"Human Anti-Idiotypic T Cells Induced By TCR Peptides Corresponding To A Common CDR3 Sequence Motif In Myelin Basic Protein-Reactive T Cells,"* Int. Immunol. 15(9):1073-1080; Loiarro, M. et al. (Epub 2010 Apr. 8) *"Targeting TLR/IL-1R Signalling In Human Diseases,"* Mediators Inflamm. 2010:674363) of B7-H4. Such molecules serve as surrogates for B7-H4 and agonize or enhance B7-H4 receptor activity, and thus their administration to a subject down-modulates the immune system of such subject by mimicking or facilitating B7-H4 binding. Such molecules thus can be used in the treatment of inflammation and autoimmune disease.

Down-modulation of the immune system is desirable in the treatment of inflammatory and auto-immune diseases, a response to transplantation rejection, graft vs. host disease or host vs. graft disease. Examples of autoimmune disorders that can be treated by administering the disclosed antibodies include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Examples of inflammatory disorders which can be prevented, treated or managed in accordance with the disclosed methods include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Thus, the disclosed antibodies and antigen-binding fragments can be used in the treatment of inflammatory and auto-immune diseases, a response to transplantation rejection, graft vs host and host vs graft diseases.

D. Methods of Administration

Various delivery systems are known and can be used to administer the disclosed therapeutic or prophylactic compositions, e.g., encapsulation in liposomes, microparticles, microcapsules, recombinant cells capable of expressing the antibody or fusion protein, receptor-mediated endocytosis (see, e.g., Wu et al., 1987, *J. Biol. Chem.* 262:4429-4432), construction of a nucleic acid as part of a retroviral or other vector, etc.

Methods of administering immunoglobulin molecules (e.g., an antibody, diabody, fusion protein, etc.) include, but are not limited to, parenteral administration (e.g., intradermal, intramuscular, intraperitoneal, intravenous and subcutaneous), epidural, and mucosal (e.g., intranasal and oral routes). In a specific embodiment, the antibodies are administered intramuscularly, intravenously, or subcutaneously. The compositions can be administered, for example, by infusion or bolus injection, by absorption through epithelial or mucocutaneous linings (e.g., oral mucosa, rectal and intestinal mucosa, etc.) and can be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this can be achieved by, for example, and not by way of limitation, local infusion, by injection, or by means of an implant, said implant being of a porous, non-porous, or gelatinous material, including membranes, such as sialastic membranes, or fibers. Preferably, when administering an antibody, care should be taken to use materials to which the antibody or the fusion protein does not absorb.

In some embodiments, the humanized or chimeric antibodies are formulated in liposomes for targeted delivery of the antibodies. Liposomes are vesicles composed of concentrically ordered phopsholipid bilayers which encapsulate an aqueous phase. Liposomes typically include various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545.

Methods of preparing liposomes with a prolonged serum half-life, i.e., enhanced circulation time, such as those disclosed in U.S. Pat. No. 5,013,556 are also provided. Preferred liposomes used in the disclosed methods are not rapidly cleared from circulation, i.e., are not taken up into the mononuclear phagocyte system (MPS).

The disclosed molecules can also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art, see, e.g., U.S. Pat. No. 6,787,153; Allen et al., 1995, Stealth Liposomes, Boca Rotan: CRC Press, 233-44; Hansen et al., 1995, *Biochim. Biophys. Acta,* 1239: 133-144.

The disclosed molecules can be packaged in a hermetically sealed container, such as an ampoule or sachette, indicating the quantity of antibody. In one embodiment, the antibodies are supplied as a dry sterilized lyophilized powder or water free concentrate in a hermetically sealed container and can be reconstituted, e.g., with water or saline to the appropriate concentration for administration to a subject. Preferably, the antibodies are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies should be stored at between 2 and 8° C. in their original container and the antibodies should be administered within 12 hours, preferably within 6 hours, within 5 hours, within 3 hours, or within 1 hour after being reconstituted. In an alternative embodiment, antibodies are supplied in liquid form in a hermetically sealed container indicating the quantity and concentration of the antibody. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies.

The precise dose to be employed in the formulation will also depend on the route of administration, and the seriousness of the condition, and should be decided according to the judgment of the practitioner and each patient's circumstances. Effective doses can be extrapolated from dose-response curves derived from in vitro or animal model test systems. For antibodies, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof can be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations including one or more antibodies. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760. In one embodiment, a pump can be used in a controlled release system (See Langer, supra; Sefton, 1987, *CRC Crit. Ref Biomed. Eng.* 14:20; Buchwald et al., 1980, Surgery 88:507; and Saudek et al., 1989, *N Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., *Macromol. Sci. Rev. Macromol. Chem.* 23:61; See also Levy et al., 1985, Science 228:190; During et al., 1989, Ann. Neurol. 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533). Controlled release systems are discussed in the review by Langer (1990, Science 249:1527-1533). Any technique known to one of skill in the art can be used to produce sustained release formulations including one or more therapeutic agents. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760.

In a specific embodiment wherein the therapeutic or prophylactic composition includes a nucleic acid encoding an antibody or an antigen-binding fragment thereof, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

Treatment of a subject with a therapeutically or prophylactically effective amount of antibodies can include a single treatment or, preferably, can include a series of treatments.

E. Combination Therapies

The molecules disclosed herein can also be administered in combination with one or more other therapies known to those skilled in the art for the treatment or prevention of cancer, autoimmune disease, infectious disease or intoxication, including but not limited to, current standard and experimental chemotherapies, hormonal therapies, biological therapies, immunotherapies, radiation therapies, or surgery. In some embodiments, the molecules are administered in combination with a therapeutically or prophylactically effective amount of one or more agents, therapeutic antibodies or other agents known to those skilled in the art for the treatment and/or prevention of cancer, autoimmune disease, infectious disease or intoxication. Such agents include for example, any of the disclosed biological response modifiers, cytotoxins, antimetabolites, alkylating agents, antibiotics, or anti-mitotic agents, as well as immunotherapeutics (such as ERBITUX™ (also known as IMC-C225) (ImClone Systems Inc.), a chimerized monoclonal antibody against EGFR; HERCEPTIN®(Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); C14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DR antibody (Techniclone); anti-CD11a is a humanized IgG1 antibody (Genetech/Xoma); ICM3™ is a humanized anti-ICAM3 antibody (ICOS Pharm); IDEC-114™ is a primatized anti-CD80 antibody (IDEC Pharm/Mitsubishi); ZEVALIN™ is a radiolabelled murine anti-CD20 antibody (IDEC/Schering AG); IDEC-131™ is a humanized anti-CD40L antibody (IDEC/Eisai); IDEC-151™ is a primatized anti-CD4 antibody (IDEC); IDEC-152™ is a primatized anti-CD23 antibody (IDEC/Seikagaku); SMART anti-CD3 is a humanized anti-CD3 IgG (Protein Design Lab); 5G1.1™ is a humanized anti-complement factor 5 (C5) antibody (Alexion Pharm); IDEC-151™ is a primatized anti-CD4 IgG1 antibody (IDEC Pharm/SmithKline Beecham); MDX-CD4™ is a human anti-CD4 IgG antibody (Medarex/Eisai/Genmab); CDP571™ is a humanized anti-TNF-α IgG4 antibody (Celltech); LDP-02™ is a humanized anti-α4β7 antibody (LeukoSite/Genentech); OrthoClone OKT4A™ is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33™ is a human anti-CD64 (FcγR) antibody (Medarex/Centeon); rhuMab-E25™ is a humanized anti-IgE IgG1 antibody (Genentech/Norvartis/Tanox Biosystems); IDEC-152™ is a primatized anti-CD23 antibody (IDEC Pharm); ABX-CBL™ is a murine anti CD-147 IgM antibody (Abgenix); BTI-322™ is a rat anti-CD2 IgG antibody (Medimmune/Bio Transplant); Orthoclone/OKT3™ is a murine anti-CD3 IgG2a antibody (ortho Biotech); SIMULECT™ is a chimeric anti-CD25 IgG1 antibody (Novartis Pharm); LDP-01™ is a humanized anti-β$_2$-integrin IgG antibody (LeukoSite); Anti-LFA-1™ is a murine anti CD18 F(ab')$_2$ (Pasteur-Merieux/Immunotech); CAT-152™ is a human anti-TGF-β$_2$ antibody (Cambridge Ab Tech); and Corsevin M™ is a chimeric anti-Factor VII antibody (Centocor), etc.). In another embodiment the disclosed molecules are administered in combination with molecules that disrupt or enhance alternative immunomodulatory pathways (such as CTLA4, TIM3, TIM4, OX40, CD40, GITR, 4-1-BB, B7-H1, PD-1, LIGHT or LAG3) or modulate the activity of effecter molecules such as cytokines (e.g., IL-4, IL-7, IL-10, IL-12, IL-15, IL-17, GF-beta, IFNg, Flt3, BLys) and chemokines (e.g., CCL21) in order to enhance the immunomodulatory effects. In yet another embodiment, the disclosed molecules are administered in combination with molecules that activate different stages or aspects of the immune response in order to achieve a broader immune response. For example, blocking tumor-mediated or TAM-mediated immune suppression with an anti-B7-H4 molecule can be combined with a molecule that enhances T cell activation or priming in order to achieve a more robust immune response.

In certain embodiments, one or more of the disclosed molecules are administered to a mammal, preferably a human, concurrently with one or more other therapeutic agents useful for the treatment of cancer. The term "concurrently" is not limited to the administration of prophylactic or therapeutic agents at exactly the same time, but rather it is meant that two agents are administered to a mammal in a sequence and within a time interval such that the two agents can act together to provide an increased benefit than if they were administered otherwise. For example, each prophylactic or therapeutic agent (e.g., chemotherapy, radiation therapy, hormonal therapy or biological therapy) can be administered at the same time or sequentially in any order at different points in time; however, if not administered at the same time, they should be administered sufficiently close in time so as to provide the desired therapeutic or prophylactic effect, or in a regimen that has been shown to provide therapeutic benefit. Each therapeutic agent can be administered separately, in any appropriate form and by any suitable route. In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

In other embodiments, the disclosed prophylactic or therapeutic agents are administered at about 2 to 4 days apart, at about 4 to 6 days apart, at about 1 week part, at about 1 to 2 weeks apart, or more than 2 weeks apart. In preferred embodiments, the prophylactic or therapeutic agents are administered in a time frame where both agents are still active, or the pharmacodynamics effects are present.

One skilled in the art would be able to determine such a time frame by determining the half-life of the administered agents.

In certain embodiments, the disclosed prophylactic or therapeutic agents are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, the disclosed prophylactic or therapeutic agents are administered in a cycle of less than about 3 weeks, about once every two weeks, about once every 10 days or about once every week. One cycle can include administration of a therapeutic or prophylactic agent by infusion over about 90 minutes every cycle, about 1 hour every cycle, about 45 minutes every cycle. Each cycle can include at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the therapeutic and prophylactic agents are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the therapeutic and prophylactic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled physician.

In other embodiments, courses of treatment are administered concurrently to a mammal, i.e., individual doses of the therapeutics are administered separately yet within a time interval such that the disclosed molecules can work together with the other agent or agents. For example, one component can be administered one time per week in combination with the other components that can be administered one time every two weeks or one time every three weeks. In other words, the dosing regimens for the therapeutics are carried out concurrently even if the therapeutics are not administered simultaneously or within the same patient visit.

When used in combination with other prophylactic and/or therapeutic agents, the disclosed molecules and the prophylactic and/or the additional therapeutic agent can act additively or, more preferably, synergistically. For example, in some embodiments, an antibody or antigen-binding fragment thereof is administered concurrently with one or more additional therapeutic agents in the same pharmaceutical composition. In another embodiments, an antibody or an antigen-binding fragments thereof is administered concurrently with one or more other therapeutic agents in separate pharmaceutical compositions. In still another embodiment, one or more of the disclosed molecules is administered prior to or subsequent to administration of another prophylactic or therapeutic agent. The two or more agents of a combination or concurrent therapy can be administered by the same or different routes of administration, e.g., oral and parenteral. In certain embodiments, when a disclosed molecule is administered concurrently with a second prophylactic or therapeutic agent that potentially produces adverse side effects including, but not limited to, toxicity, the second prophylactic or therapeutic agent can advantageously be administered at a dose that falls below the threshold that the adverse side effect is elicited.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ ed., 2002).

F. Pharmaceutical Compositions

Compositions including one or more of the disclosed molecules are provided. The compositions can include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions typically include a prophylactically or therapeutically effective amount of a prophylactic and/or therapeutic agent disclosed herein or a combination of those agents and a pharmaceutically acceptable carrier. Preferably, the compositions include a prophylactically or therapeutically effective amount of one or more of the disclosed humanized antibodies or antigen-binding fragments there and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

G. Kits

Pharmaceutical packs and kits including one or more containers filled with the disclosed humanized antibodies or antigen-binding fragments thereof are also provided. Additionally, one or more other prophylactic or therapeutic agents useful for the treatment of a disease can also be included in the pharmaceutical pack or kit. A pharmaceutical pack or kit can include one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

Kits including one or more of the disclosed humanized antibodies or antigen-binding fragments thereof can be for use with one or more of the disclosed methods. For example, a kit for use in the treatment of cancer can include one or more other prophylactic or therapeutic agents useful for the treatment of cancer, in one or more containers. In another embodiment, a kit includes one or more additional antibodies, for example, cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

H. Diagnostic Methods

The disclosed anti-B7-H4 binding molecules can be used for diagnostic purposes, such as to detect, diagnose, or monitor diseases, disorders or infections associated with B7-H4 expression, or to determine or assist in the determination or identification of suitable patient populations or profiles. The detection or diagnosis of a disease, disorder or infection, particularly an autoimmune disease can include: (a) assaying the expression of B7-H4 or derivatives thereof in cells, serum, plasma, blood or in a tissue sample of a subject using one or more antibodies (or fragments thereof) that immunospecifically bind to such antigens; and (b) comparing the level of the antigen with a control level, e.g., levels in normal tissue samples, whereby an increase or decrease in the assayed level of antigen compared to the control level of the antigen is indicative of the disease, disorder or infection. Such antibodies and fragments are preferably employed in immunoassays, such as the enzyme linked immunosorbent assay (ELISA), the radioimmunoassay (RIA) and fluorescence-activated cell sorting (FACS).

In some embodiments, the antibodies or fragments are used for IHC analysis in cells of an in vitro or in situ tissue sample or in vivo. For example, since B7-H4 is particularly expressed by cancer cells but not by normal tissue (Sica, G. L. et al. (2003) "*B7-H4, A Molecule Of The B7 Family, Negatively Regulates T Cell Immunity*," Immunity 18:849-861; Choi, I. H. et al. (2003) "*Genomic Organization And Expression Analysis Of B7-H4, An Immune Inhibitory Molecule Of The B7 Family*," J. Immunol. 171:4650-4654), detection of its presence on a cell by such cell's binding to such antibodies or fragments is indicative and diagnostic of a cancer cell. Thus, a cytologic assay for diagnosing the presence of cancer in a subject is provided.

Since B7-H4 is over-expressed upon HIV infection (Carter, C. A. et al. (2008) "*Cell Biology Of HIV-1 Infection Of Macrophages*," Ann. Rev. Microbiol. 62:425-443; Noursadeghi, M. et al. (2006) "*HIV-1 Infection Of Mononuclear Phagocytic Cells: The Case For Bacterial Innate Immune Deficiency In AIDS*," Lancet Infect. Dis. 6:794-804), the expression of B7-H4 on such cells (as detected by the disclosed antibodies and antigen-binding fragments) can be used to diagnose HIV in humans.

Thus, the antibodies and fragments can be used in the detection and diagnosis of a disease, disorder, or infection in a human. In one embodiment, such diagnosis includes: a) administering to a subject (for example, parenterally, subcutaneously, or intraperitoneally) an effective amount of such labeled antibody or antigen-binding fragment; b) waiting for a time interval following the administration for permitting the labeled molecule to preferentially concentrate at sites in the subject where B7-H4 is expressed (and for unbound labeled molecule to be cleared to background level); c) determining background level; and d) detecting the labeled antibody in the subject, such that localized detection of labeled antibody above the background level indicates that the subject has the disease, disorder, or infection. In accordance with this embodiment, the antibody can be labeled with an imaging moiety which is detectable in vivo using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In vivo tumor imaging is described in S. W. Burchiel et al., "*Immunopharmacokinetics of Radiolabeled Antibodies and Their Fragments*," (Chapter 13 in TUMOR IMAGING: THE RADIOCHEMICAL DETECTION OF CANCER, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that can be used in the diagnostic methods include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Those skilled in the art will recognize, or be able to ascertain using no more than routine experimentation, many equivalents to the specific embodiments of the invention described herein. Such equivalents are intended to be encompassed by the following claims.

Example 1

Characterization of Anti-Human B7-H4 Antibody 6H3

Materials and Methods

Figure 2A:
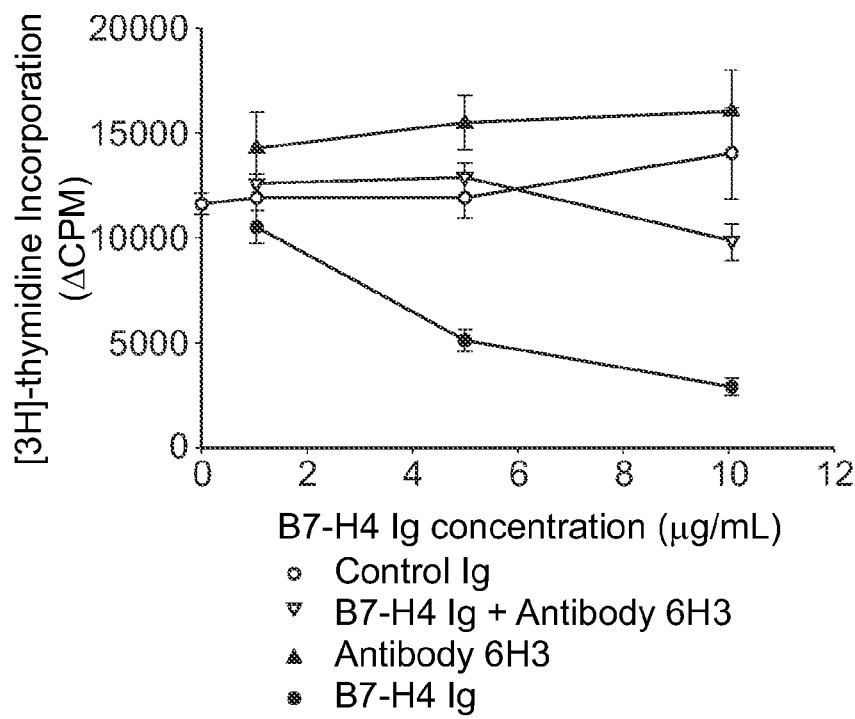
FIGS. 2A-2B are line graphs showing the ability of antibody 6H3 to block B7-H4 Ig-mediated suppression of T cell activation as measured by thymidine incorporation (FIG. 2A) and IL-17 expression (FIG. 2B) as a function of antibody concentration (μg/ml).
Figure 2B:
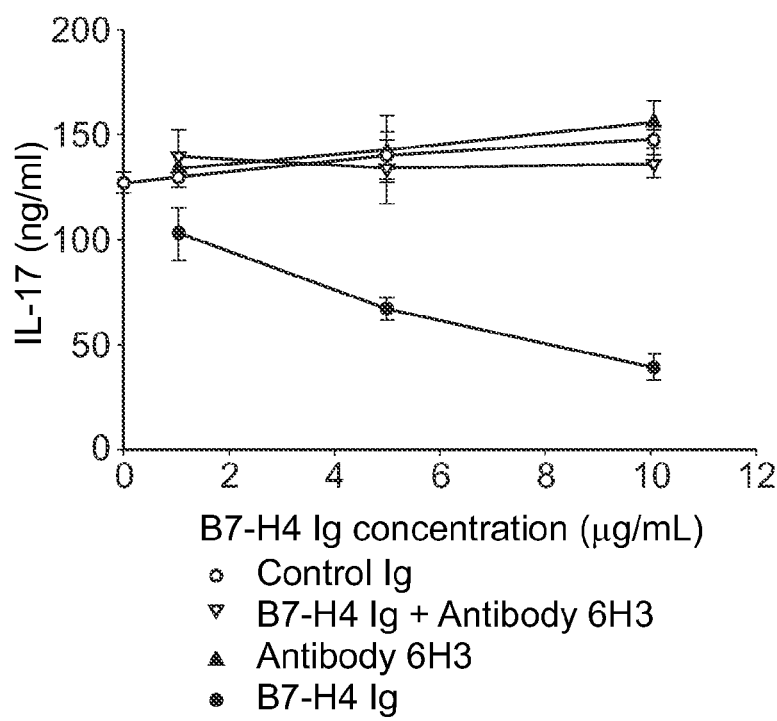
Figure 3A:
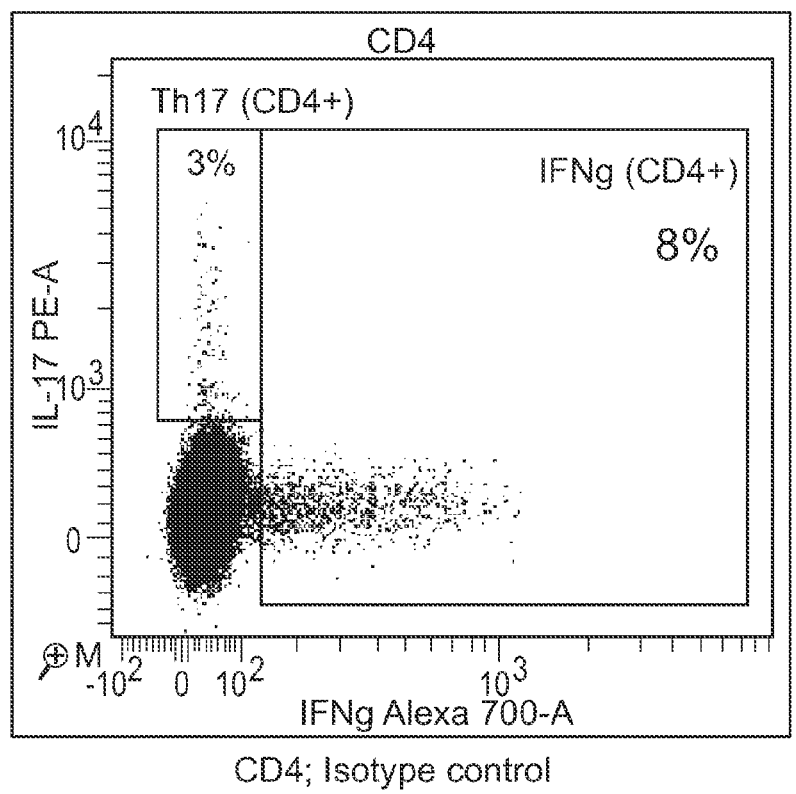
FIGS. 3A-3D are scatterplots showing that antibody 6H3 was capable of enhancing ovarian cancer patients' T cell response (functional CD4 and CD8 cells producing IL-17 or INFγ) in the presence of TAMs from ovarian cancer patients (FIG. 3A: CD4, isotype control.
Figure 3B:
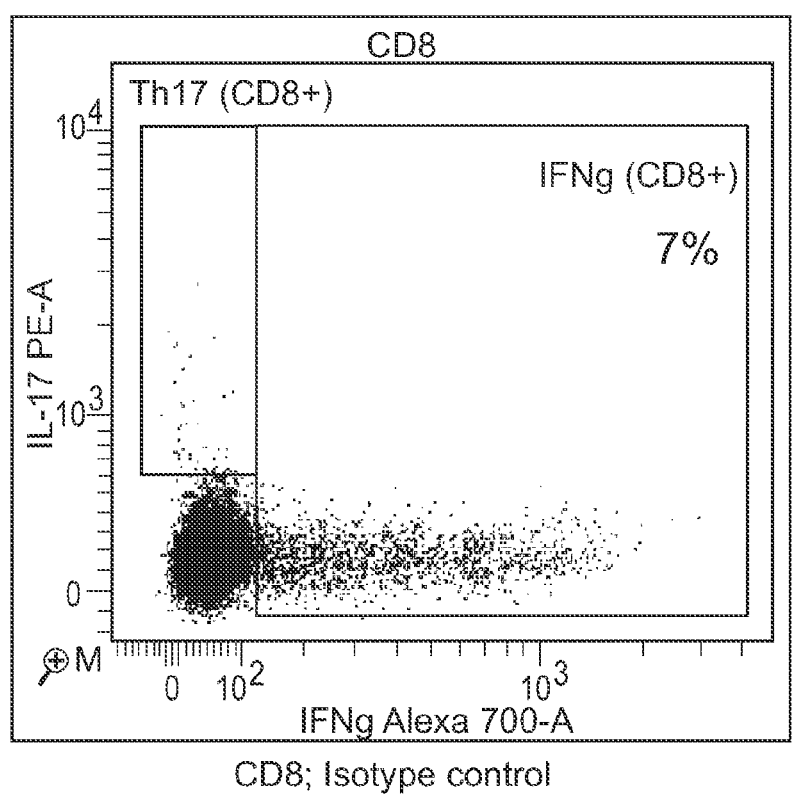
Figure 3C:
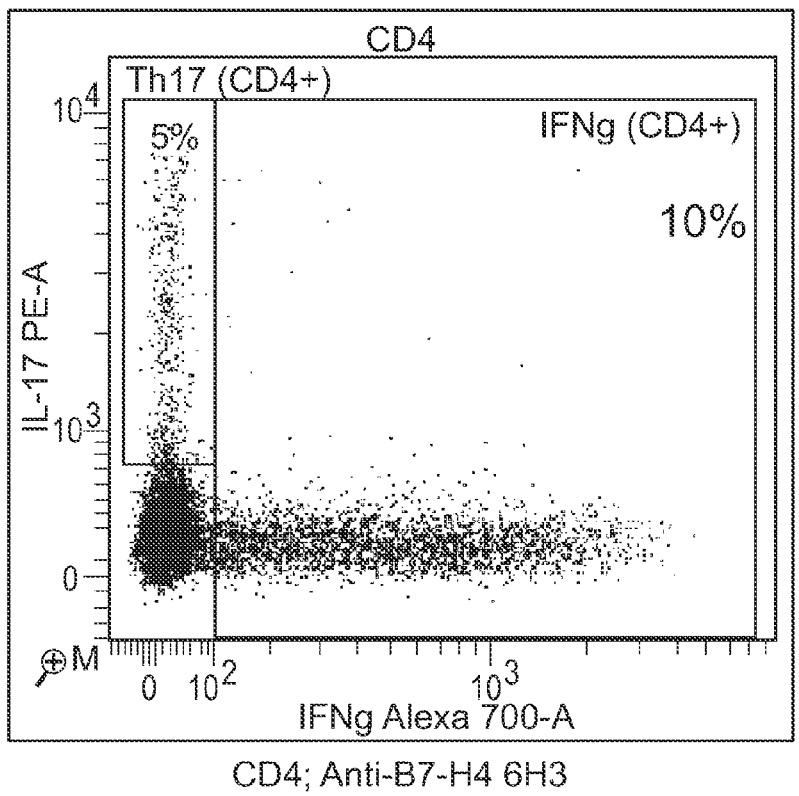
Figure 3D:
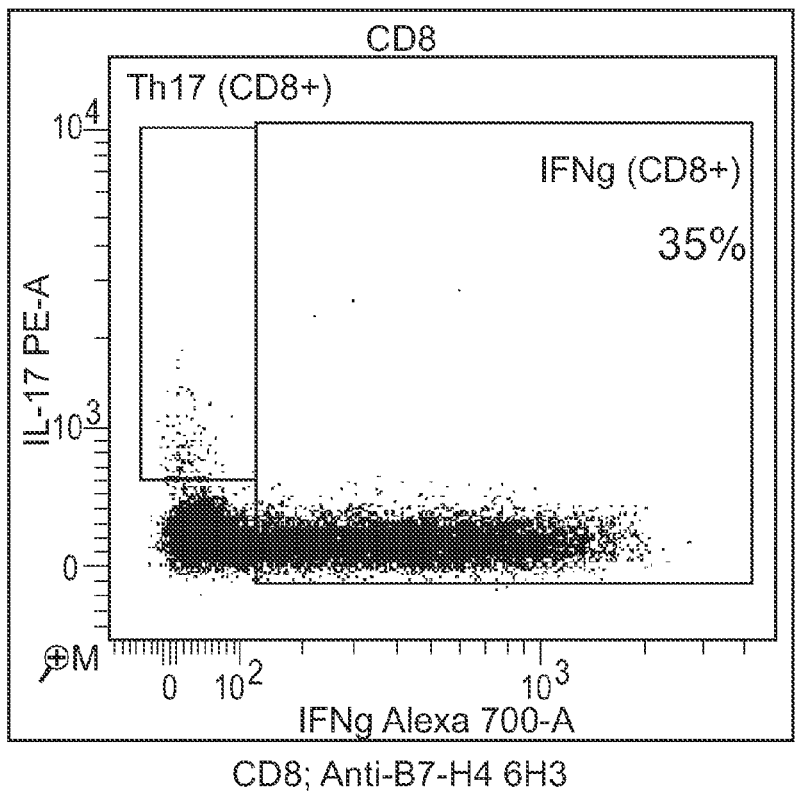
Figures 4A, 4B:
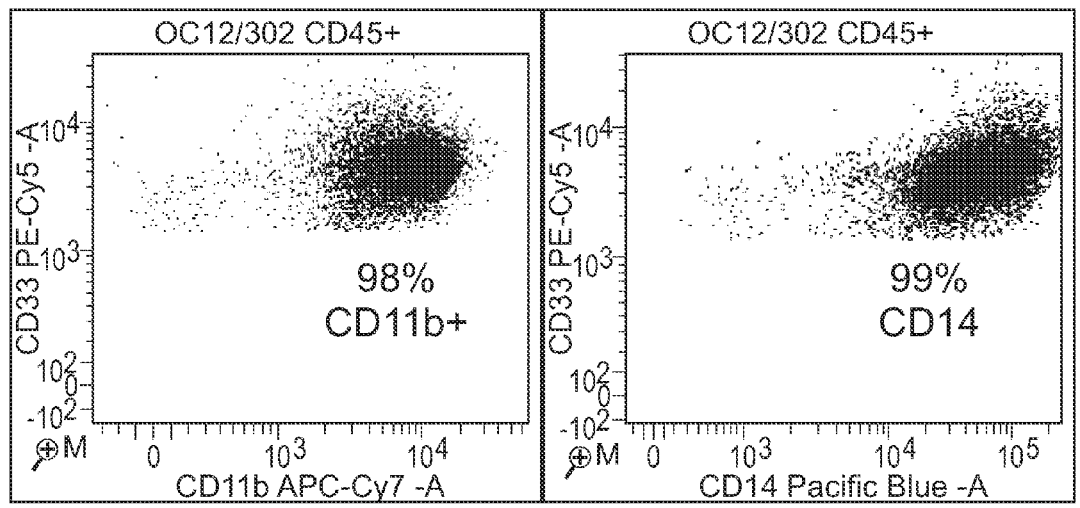
FIGS. 4A-4I are scatterplots showing the expression of B7-H4 (FIG. 4H) and other antigens (CD11b (FIG. 4A), CD14 (FIG. 4B), CD123 (FIG. 4C), CD86 (FIG. 4D), CD80 (FIG. 4E), HLA-DR (FIG. 4F), B7-H1 (FIG. 4G), and B7-DC (FIG. 4I)) by ovarian cancer patient tumor-associated macrophages (TAMs), and the ability of antibody 6H3 to detect B7-H4 expression by such cells.
Figures 4C, 4D:
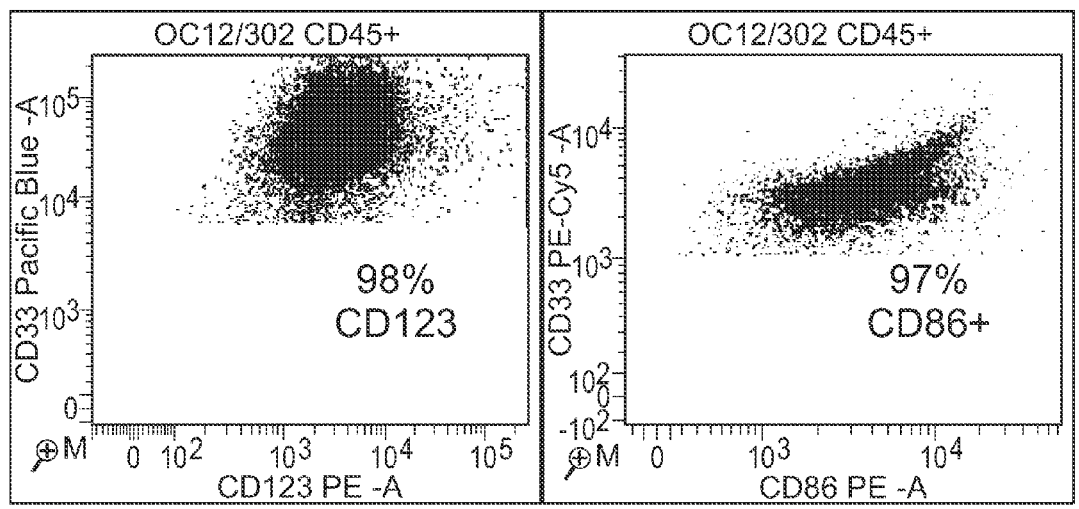
Figure 4E:
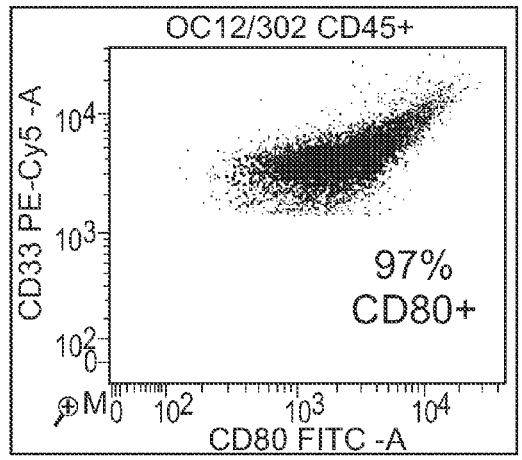
Figure 4F:
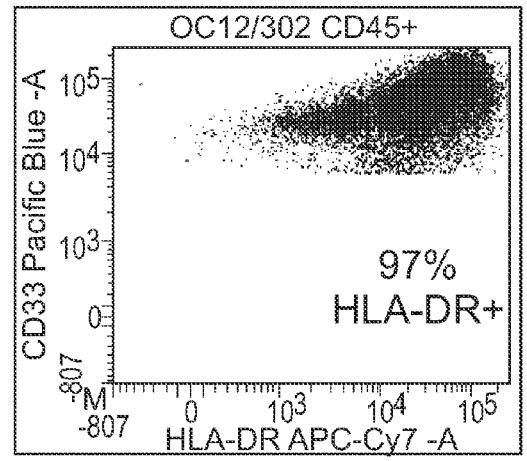
Figure 4G:
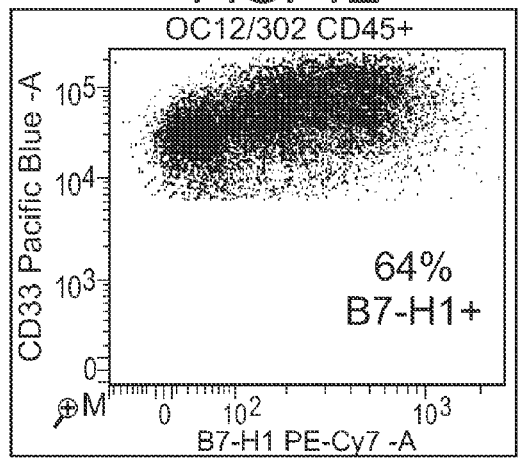
Figure 4H:
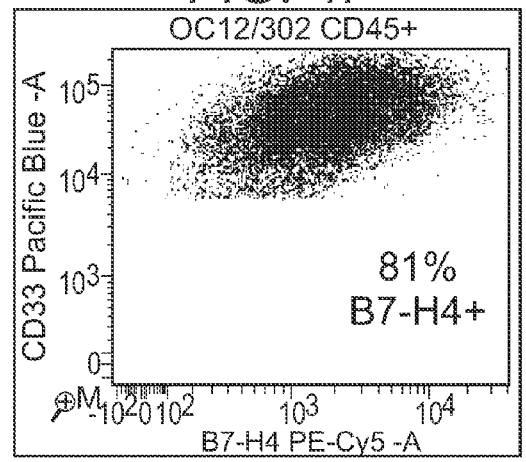
Figure 4I:
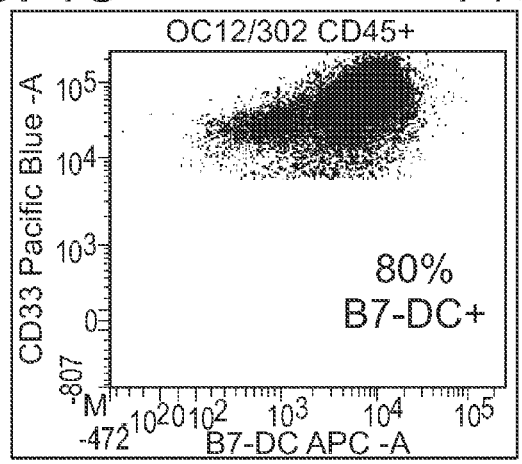

Naïve T (CD4$^+$CD62L$^+$) cells were first isolated from DO11.10 mice and polarized to Th17 cells in the presence of recombinant TGF-β (10 ng/mL), IL-6 (50 ng/mL), IL-23 (4 ng/mL), anti-IL-4 (1 μg/mL), anti-IFN-γ (1 μg/mL) and anti-IL-2 (1 μg/mL) plus OVA$_{323-339}$ pulsed APC (APC/OVA) for OVA specific stimulation. Murine B7-H4 Ig or control IgG at various doses was added directly to the culture in the presence of 5 μg/mL of 6H3 and cultured for 3 days. For proliferation assessment, 1 μci of [$^3$H]-thymidine was added 24 hours before harvest. T cell proliferation was assessed by thymidine incorporation (FIG. 2A). Conditioned culture supernatant was analyzed for IL-17 production (FIG. 2B).

Results

Multiple independent approaches were used to establish that antibody 6H3 was capable of immunospecifically binding to human B7-H4. In one such approach, the ability of the antibody to block B7-H4 Ig mediated inhibition of Th17 (and Th1) differentiation was assessed. Accordingly, splenocytes from 8-9 week-old NOD mice were cultured with anti-CD3/CD28 under Th17 polarization conditions in the presence of control Ig or murine B7-H4.Ig for 3 days. The ability of antibody 6H3 (10 mg/ml) to neutralize the effect of B7-H4.Ig in the culture was assessed. The results of this experiment show that administration of B7-H4 Ig inhibited proliferation as shown by the decreased incorporation of thymidine (FIG. 2A) as well as by the decreased expression of IL-17 (FIG. 2B). This inhibition is reversed by the administration (or co-administration) of antibody 6H3. The production of IL-17 was assessed using flow cytometry.

In a second approach, the ability of the antibody to enhance a CTL response by cells post ovarian cancer TAM coincubation was assessed in an allo T cell assay. FIGS. 3A-3D show that antibody 6H3 was capable of mediating such an enhanced CTL response (Table 2).

TABLE 2

| | Isotype | Anti-B7-H4 Antibody 6H3 |
|---|---|---|
| Th17 | 3% | 5% |
| Th1 | 8% | 10% |
| CD8+/IFN-γ | 7% | 35% |

In a third approach, antibody 6H3 was tested for its ability to detect the expression of B7-H4 by ovarian cancer patient tumor-associated macrophages (TAMs). As shown in FIGS. 4A-4I, antibody 6H3 detected B7-H4 on such cells.

In order to determine the kinetics of binding of antibody 6H3 binding to B7-H4, with HEK293 cells that expressed full length human B7-H4 were incubated (for 20 minutes at 4° C. with 1×10$^5$ in 200 μl wells) in the presence of varying concentrations of antibody (0, 0.01 ng, 0.03 ng, 0.1 ng, 0.3 ng, 1 ng, 10 ng, 30 ng, 100 ng, 300 ng, 1000 ng, 3000 ng, 10000 ng, or 30000 ng) in RPMI complete media (10% FBS). Binding was analyzed (FACS Canto II) using a FACS staining plate after incubation with a secondary antibody (anti-human Ig PE, anti-mouse Ig APC, anti-hamster Ig PE or anti-rat Ig PE). The results of the analysis are shown in Table 3.

TABLE 3

| Antibody Solution and Volume Employed | | | | | 10% | | Mean Florescence |
|---|---|---|---|---|---|---|---|
| 0.01 ng/μl | 1 ng/μl | 100 ng/μl | 1000 ng/μl | Amount (ng) | RPMI Added | Total Volume | Intensity (MFI) |
| | | | | 0 | 200 | 200 | 191 |
| 3 | | | | 0.03 | 197 | 200 | 197 |
| 10 | | | | 0.1 | 190 | 200 | 197 |
| 30 | | | | 0.3 | 170 | 200 | 220 |
| 100 | | | | 1 | 100 | 200 | 197 |
| | 3 | | | 3 | 197 | 200 | 273 |
| | 10 | | | 10 | 190 | 200 | 394 |
| | 30 | | | 30 | 170 | 200 | 505 |
| | 100 | | | 100 | 100 | 200 | 1072 |
| | | 3 | | 300 | 197 | 200 | 1980 |
| | | 10 | | 1000 | 190 | 200 | 2719 |
| | | 30 | | 3000 | 170 | 200 | 2843 |

Figure 5:
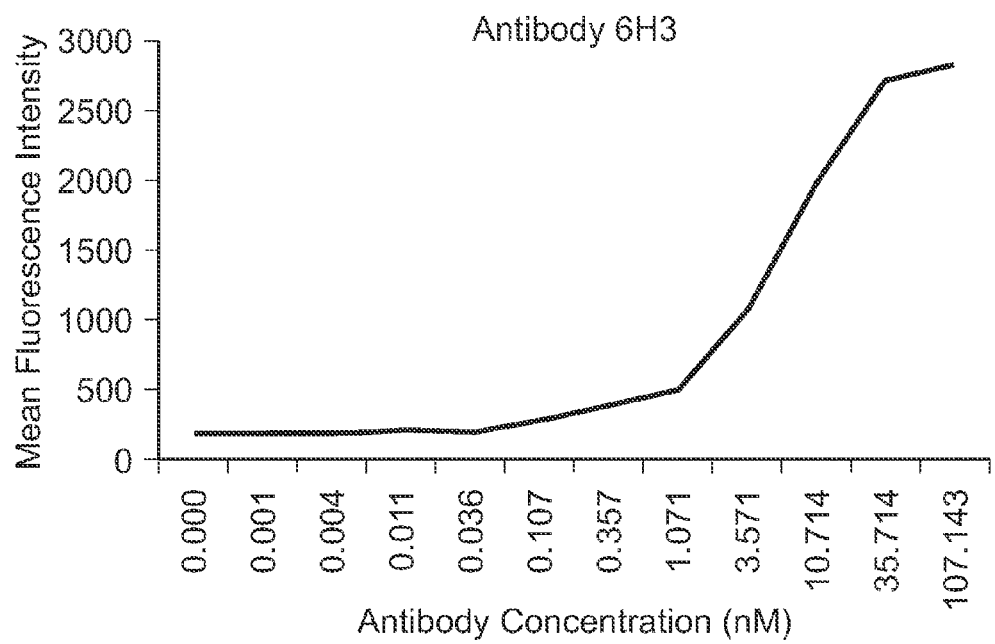
FIG. 5 is a binding curve showing the kinetics of binding of antibody 6H3 binding to B7-H4 as a function of antibody concentration (nM).

The results are shown graphically in FIG. 5.

Figure 6:
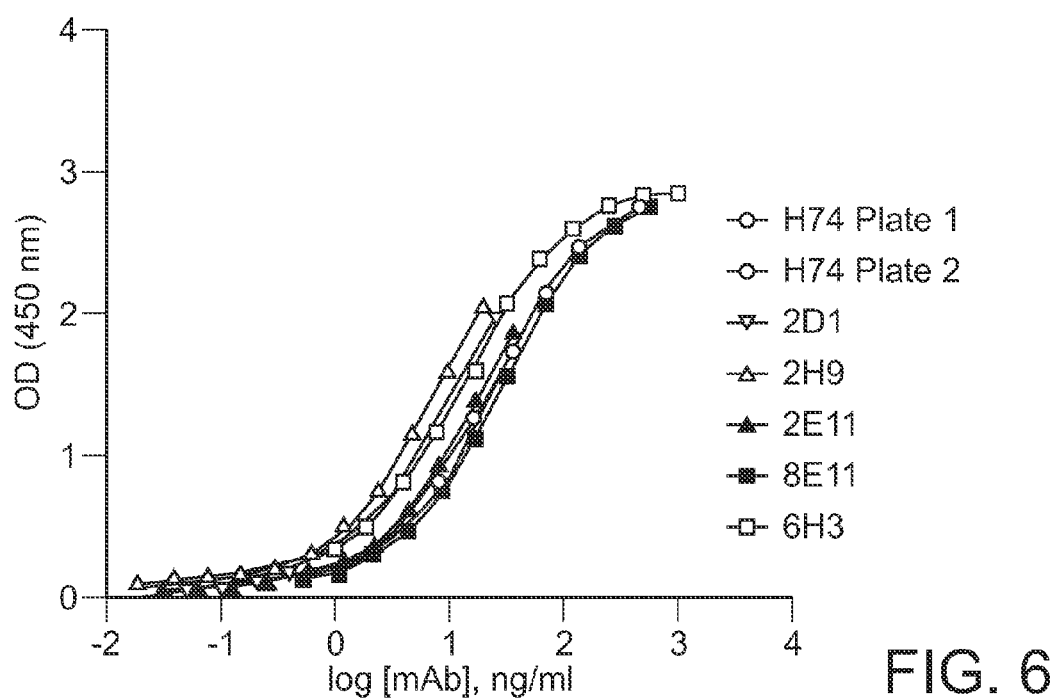
FIG. 6 is a binding curve showing the kinetics of human H7-H4 binding of antibody 6H3 relative to other anti-B7-H4 antibodies (i.e., antibodies H74, 2D1, 2H9, 2E11 and 8E11) as a function of antibody concentration (log [mAb], ng/ml).

FIG. 6 shows the kinetics of human H7-H4 binding of antibody 6H3 relative to other anti-B7-H4 antibodies (i.e., antibodies H74, 2D1, 2H9, 2E11 and 8E11). B7-H4 Ig was coated onto microtiter plates, washed, blocked, and washed again. Varying concentrations of anti-B7-H4 antibodies were allowed to bind. Purified proteins were used for clones H74, 6H3, and 8E11. Conditioned media from hybridomas 2D1, 2H9, and 2E11 were used. Following incubation, the plates were washed. Bound anti-B7-H4 was detected using HRP-conjugated goat anti-mouse (Jackson ImmunoResearch).

Example 2

Anti-B7-H4 Antibody 6H3 Recognizes The B7-H4 IgC Region

Materials and Methods

100 μl 1 μg/ml human IgG1 Fc fusion proteins diluted in PBS consisting of different segments of B7-H4 Extracellular domains were immobilized on flat bottom 96 well plates (Costar 9017) overnight at 4° C. B7-H4 fusion proteins include Variant 1: IgV residues 29-149 of SEQ ID NO:1; Variant 2: IgV residues 29-154 of SEQ ID NO:1; Variant 3: IgV residues 29-158 of SEQ ID NO:1; Variant 4: ECD-hIgG4; Variant 5: IgC residues 154-259 of SEQ ID NO:1; Variant 6: ECD-hIgG1-SEQ ID NO:7). Plates were washed twice with PBS+0.1% PS-20 and blocked with 200 μl/well PBS 10% FBS at RT for 1 hr. A titration of mouse anti-human B7-H4 antibodies 2H9, 2D1, 2E11, 6H3, 8E11 or H74 diluted in PBS 10% FBS were added to the plates and incubated at RT for 1 hr. Plates were washed three times and 100 µl 1 µg/ml anti-mouse Ig HRP (Sigma) was added to each well and incubated at RT for 1 hr. Plates were washed six times and 100 µl TMB substrate (SurModics) was added to each well for 5-15 mins. 100 µl stop solution (0.1M Sulfuric acid) was added to each well. Plates were read at Absorbance 450 nm by PerkinElmer EnVision 2104 Multi-label Reader.

Results

The extracellular domain of B7-H4 contains an IgV-like domain (residues Ile 48-Phe 150 of SEQ ID NO:1) and an IgC-like domain (residues Val 157-Gly 236 of SEQ ID NO:1) (Sica, G. L. et al. (2003) *"B7-H4, A Molecule Of The B7 Family, Negatively Regulates T Cell Immunity,"* Immunity 18:849-861). The IgV-like domain contains the complete binding site for CD28; the IgC-like domain is believed to participate in an increase in the affinity for CTLA4 (see, Inobe, M. et al. (1994) *"Identification Of An Alternatively Spliced Form Of The Murine Homologue Of B7,"* Biochem. Biophys. Res. Commun 200(1):443-449).

Figure 7:
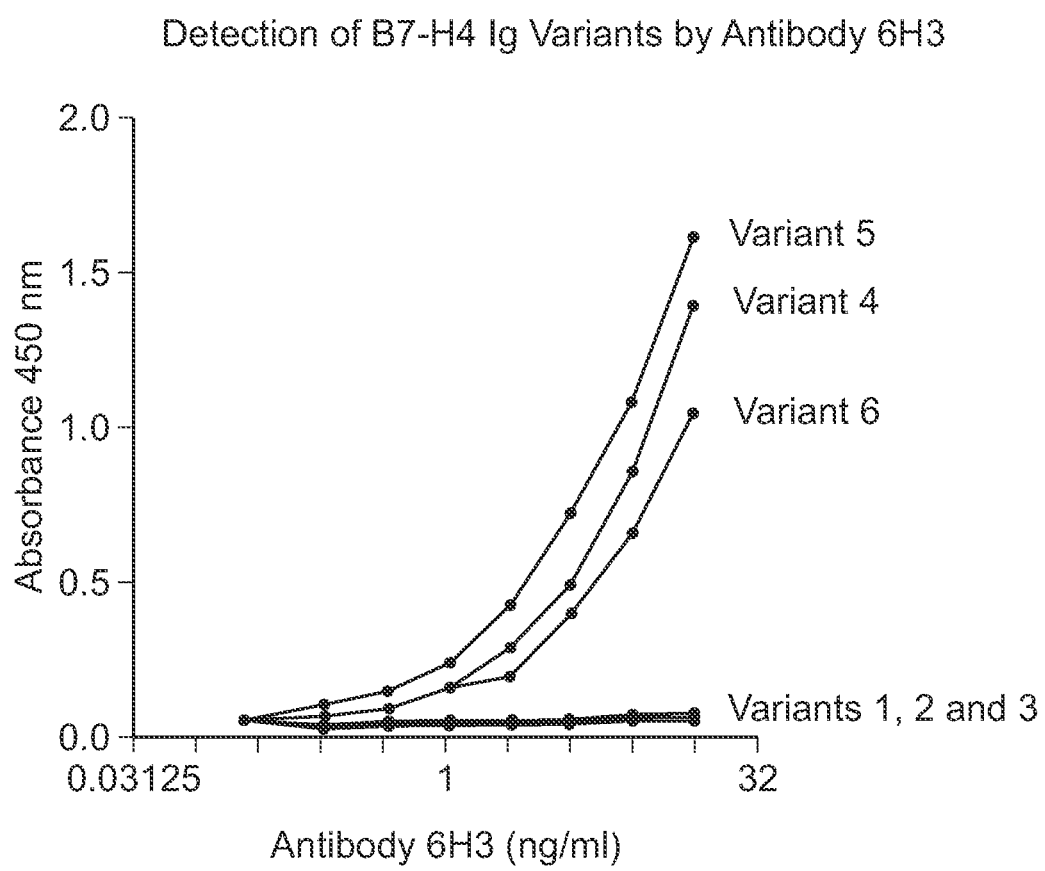
FIG. 7 is a binding curve showing the ability of antibody 6H3 to bind to the IgC region of B7-H4 (Variant 1: IgV residues 29-149 of SEQ ID NO:1; Variant 2: IgV residues 29-154 of SEQ ID NO:1; Variant 3: IgV residues 29-158 of SEQ ID NO:1; Variant 4: ECD-hIgG4; Variant 5: IgC residues 154-259 of SEQ ID NO:1; Variant 6: ECD-hIgG1-SEQ ID NO:7) as a function of antibody concentration (nM).

In order to determine the B7-H4 domain recognized by antibody 6H3, the antibody was incubated in the presence of B7-H4 variants having defined deletions, and the extent of binding was measured. The results of this study indicated that antibody 6H3 did not bind to B7-H4 variants containing residues 29-149 of SEQ ID NO:1 (Variant 1) or to B7-H4 variants containing residues 29-154 of SEQ ID NO:1 (Variant 2), or to B7-H4 variants containing residues 29-158 of SEQ ID NO:1 (Variant 3), but did bind to B7-H4 variants containing the B7-H4 extracellular domain (ECD)-hIgG4 (Variant 4), and to B7-H4 variants containing residues 154-259 of SEQ ID NO:1 (Variant 5), and to B7-H4 variants containing the B7-H4 ECD-hIgG1-KRRSKQQS (Variant 6; KRRSKQQS is SEQ ID NO:7) (FIG. 7). Accordingly, anti-B7-H4 antibody 6H3 recognizes the B7-H4 IgC region.

The analysis was also performed using anti-human B7-H4 antibodies 2H9, 2D1 and H74. The amino acid sequences of the light and heavy chain variable regions of anti-B7-H4 mAbs 2H9 and 2D1 are as follows (CDRs are underlined); antibody H74 is a commercially-available anti-human B7-H4 antibody (eBioscience, San Diego, Calif.)):

```
Anti-Human B7-H4 Clone 2H9
Light Chain Variable Region:
                                       (SEQ ID NO: 8)
DIVLTQSPAS LAVSLGQRAT ISCRASESID NYGISFMHWY
QQKPGQPPKL

LIYRASNLES GIPARFSGSG SRTDFTLTIN PVETDDVATY
FCQQSDEGRT

FGGGTKLEIK

Heavy Chain Variable Region:
                                       (SEQ ID NO: 9)
EVQLVESGGN LVKPGGSLKL SCAASGFTFS NSAMSWVRQT
PEKRLEWVAT

ISDGGRYTYY PDNVKGRFTI SRDNAKNNLY LQMSHLKSED
TALYYCARDR

PHWYFDVWGT GATVTVSS

Anti-Human B7-H4 Clone 2D1
Light Chain Variable Region:
                                       (SEQ ID NO: 10)
DVVMTQTPLS LPVSLGDQAS ISCRSSHSLV HSNGNTYLHW
YLQKPGQSPN

LLIYIVSNRF SGVPDRFSGS GSGTDFTLKI SRVEAEDLGV
YFCSQSTHVP

PTFGAGTKLE LK

Heavy Chain Variable Region:
                                       (SEQ ID NO: 11)
EVQLVESGGG LVKPGGSLKL SCAASGFTFN SHGMSWVRQT
PEKRLDWVAT

ISDGGTYTYY PVNVKGRFTI SRDNAKNNLY LQMSHLKSED
TAMYYCARDG

GGGAYWGQGT LVTVSA
```

Figure 8A:
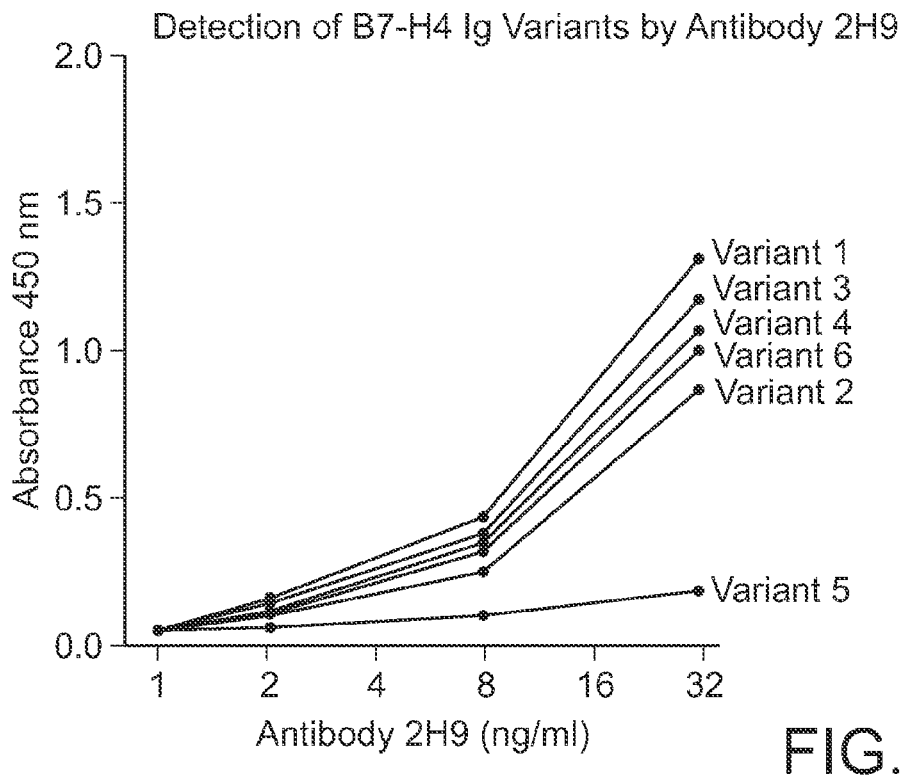
FIGS. 8A-8C are binding curves showing the regions of B7-H4 that are recognized by anti-human B7-H4 antibodies 2H9 (FIG. 8A), 2D1 (FIG. 8B) and H74 (FIG. 8C) (Variant 1: IgV residues 29-149 of SEQ ID NO:1; Variant 2: IgV residues 29-154 of SEQ ID NO:1; Variant 3: IgV residues 29-158 of SEQ ID NO:1; Variant 4: ECD-hIgG4; Variant 5: IgC residues 154-259 of SEQ ID NO:1; Variant 6: ECD-hIgG1-SEQ ID NO:7) as a function of antibody concentration (nM).
Figure 8B:
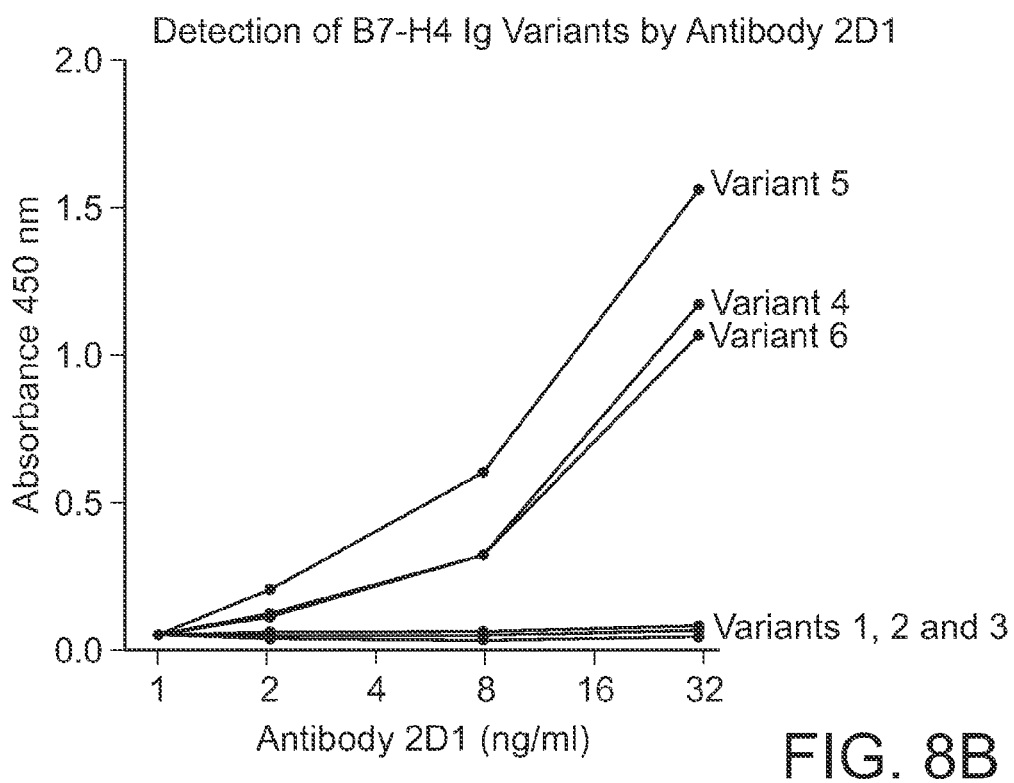
Figure 8C:
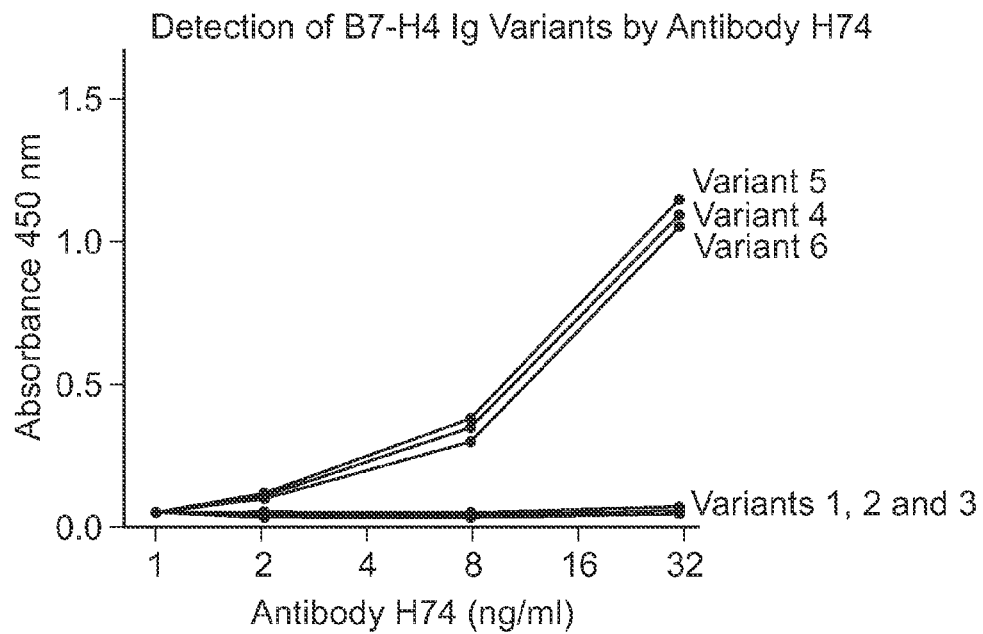

The results of this analysis are shown in FIGS. 8A-8C, and are summarized in Table 4.

TABLE 4

|  | B7-H4 Domain Recognized | | | |
|---|---|---|---|---|
| Antibody | ECD | IgV only | | IgC only |
| 2H9 | + | + | + | + | − |
| 2D1 | + | − | − | − | + |
| 6H3 | + | − | − | − | + |
| H74 | + | − | − | − | + |

The results were confirmed using western analysis.

Example 3

Anti-Human B7-H4 Antibody 6H3 Possesses Unexpected Characteristics Relative to Other Anti-Human B7-H4 Antibodies Materials and Methods Naïve CD4+ T cells (CD4+ CD62L+) were isolated from DO11.10 mice and cultured with irradiated antigen presenting cells (APC) harvested from Balb/C mice pulsed with $OVA_{323-339}$ peptide for 3 days in the presence of increase concentration of human B7-H4 Ig plus 10 µg/mL of anti-B7-H4 Abs. [$^3$H]-thymidine was added in the culture in the last 24 hours prior to thymidine incorporation analysis.

Results

Anti-B7-H4 antibodies block B7-H4 Ig mediated suppression of T cell activation. In order to demonstrate the distinctiveness of antibody 6H3, naïve CD4+ T cells (isolated from DO11.10 mice) were cultured with irradiated OVA-specific antigen presenting cells (APC) in the presence of increasing concentrations of human B7-H4 Ig plus 10 µg/mL of the anti-B7-H4 mAbs 2E11 and 2H9. The amino acid sequences of the light and heavy chain variable regions of anti-B7-H4 antibody 2H9 is SEQ ID NOS:8-9. The amino acid sequences of the light and heavy chain variable regions of anti-B7-H4 antibody 2E11 are as follows (CDRs are underlined):

```
Anti-Human B7-H4 Clone 2E11
Light Chain Variable Region:
                                       (SEQ ID NO: 12)
DIVMSQSPSS LAVSVGEKVT VSCKSSQSLL YSTNQRTYLA
WFQQKPGQSP

KLLIYWASTR ESGVPDRFTG SGSGTDFTLT ISSVKAEDLA
VYYCQQYYNY

PLTFGTGTKL ELK
```

-continued

```
Heavy Chain Variable Region:
                                       (SED ID NO: 13)
EVKLVESEGG LVQPGSSMKL SCTASGFKFT DYYMAWVRQV
PEKGLEWVAN

INYDGSSTYY LDSLKSRFII SRDNAKNILY LQMNSLKSED
TATYYCARKG

YFDYWGQGTT LTVSS
```

Figure 9:
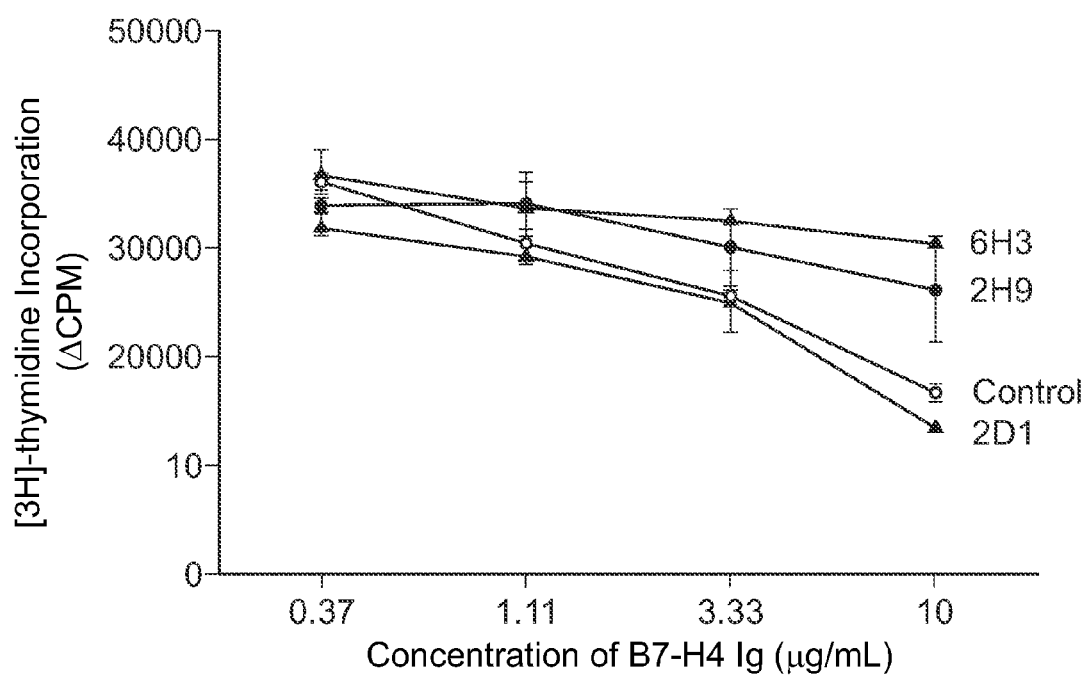
FIG. 9 is a line graph comparing the ability of anti-human B7-H4 antibodies 6H3, 2H9 and 2D1 to block B7-H4 Ig mediated suppression of T cell activation (proliferation measured by 3H-thymidine incorporation (ΔCPM)) as a function of antibody concentration (ng/ml).
Figure 10A:
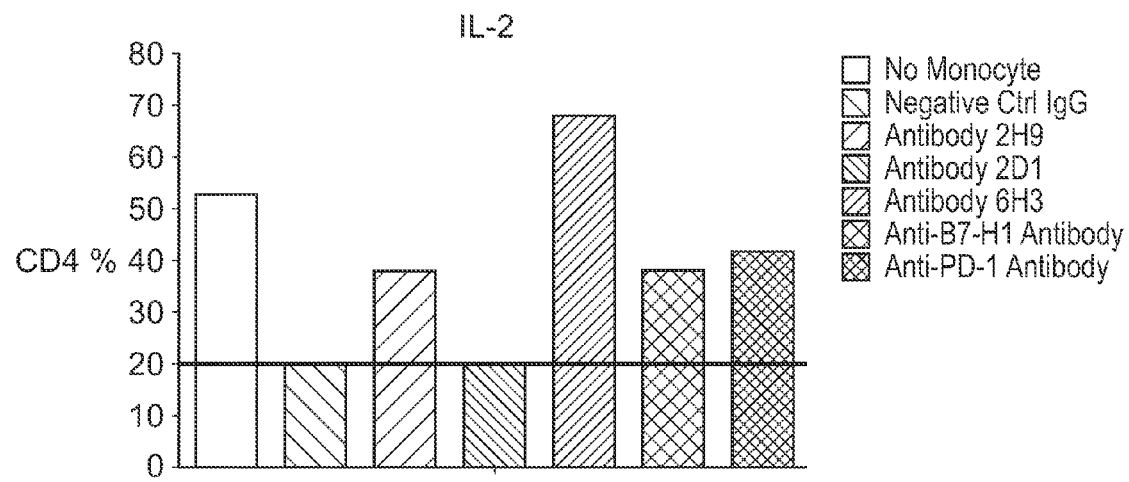
FIGS. 10A-10F are bar graphs showing the ability of antibodies (no monocytes control, Palivizumab, 2H9, 2D1, 6H3, anti-B7-H1, anti-PD1) to reverse IFNγ primed monocyte-mediated suppression. T cells were stained for IL-2 (CD4+ T cells, FIG. 10A; CD8+ T cells, FIG. 10B), TNF-α (CD4+ T cells, FIG. 10C; CD8+ T cells, FIG. 10D) or IL-8 (CD4+ T cells, FIG. 10E; CD8+ T cells, FIG. 10F).
Figure 10B:
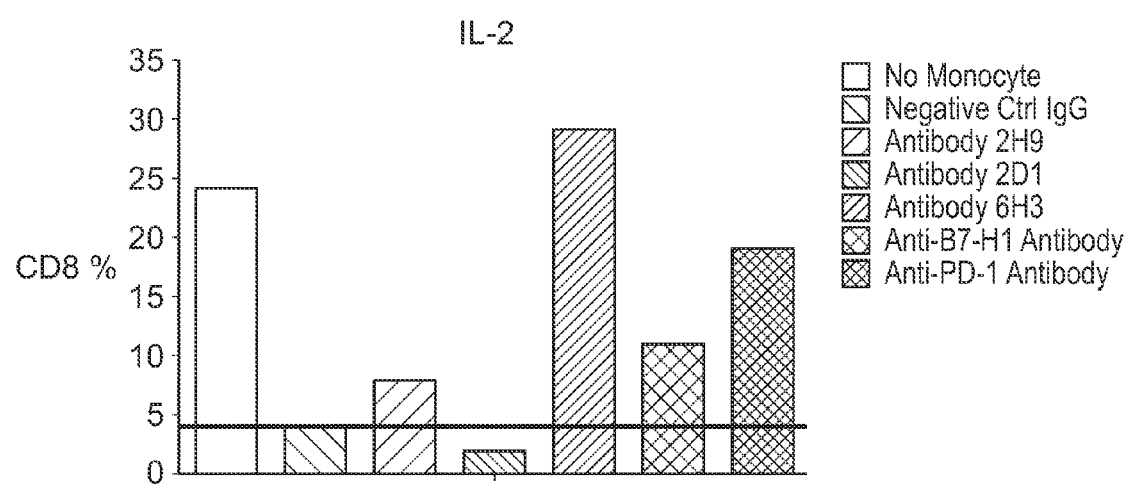
Figure 10C:
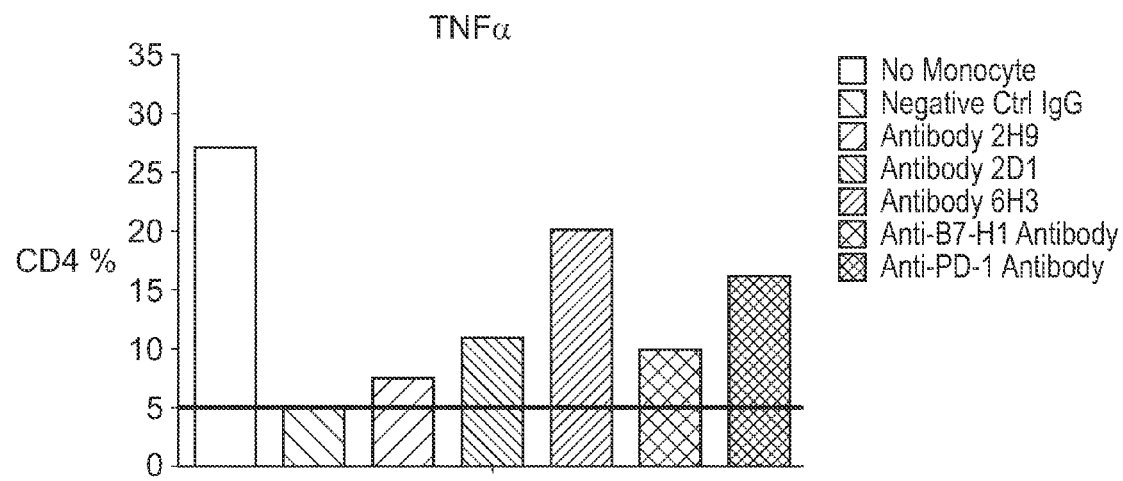
Figure 10D:
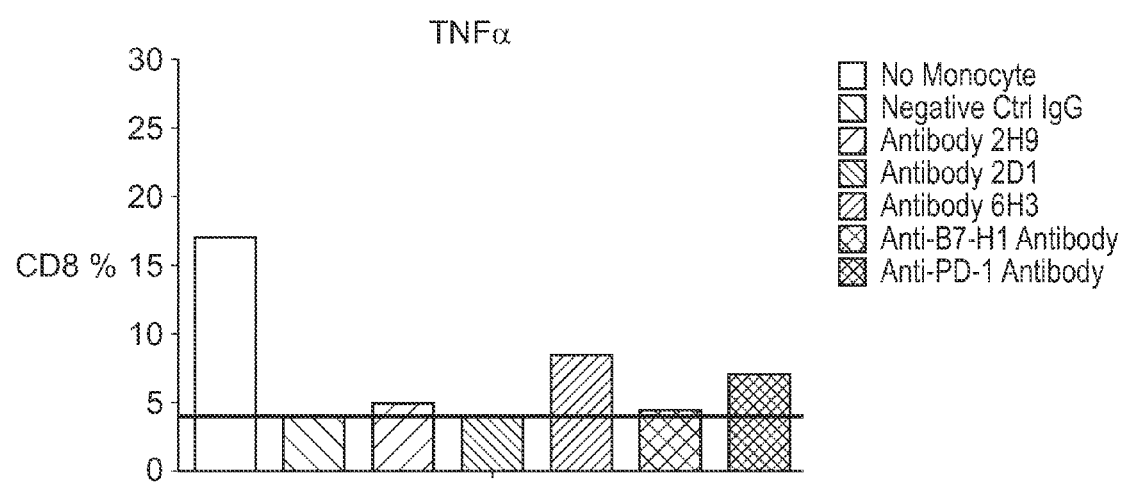
Figure 10E:
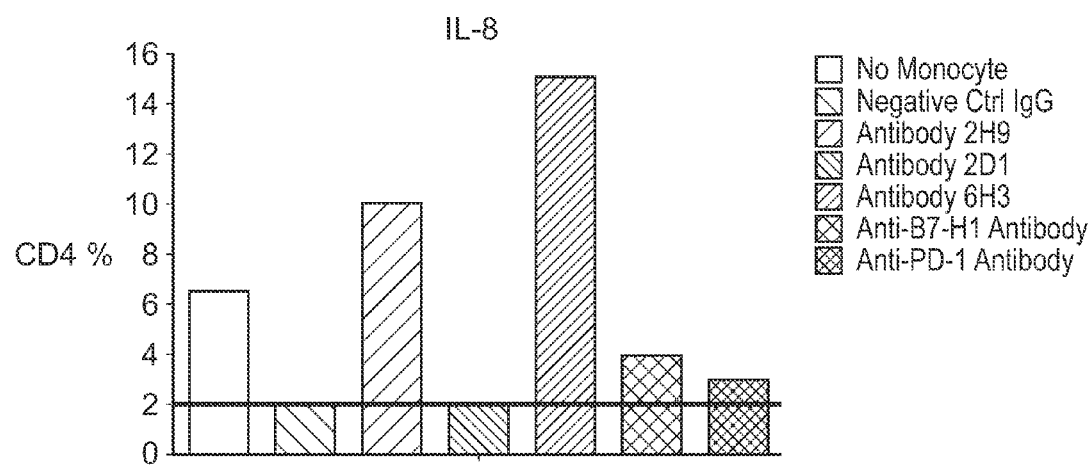
Figure 10F:
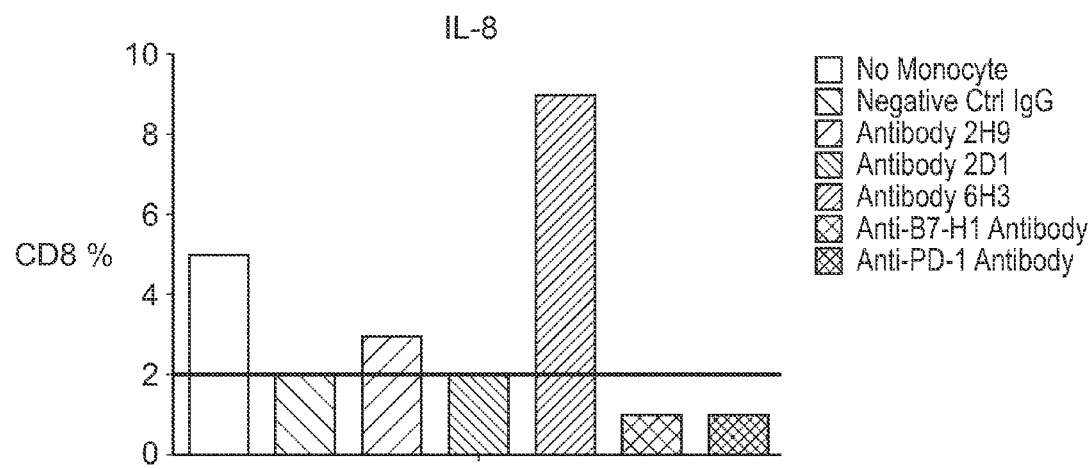
Figure 11A:
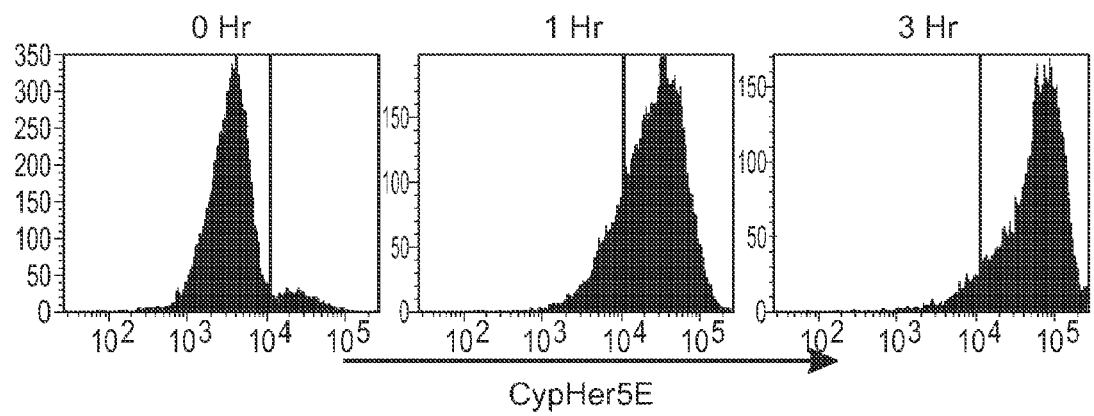
FIGS. 11A-11B reveal that antibody 6H3 induced robust internalization of B7-H4 expressed on the surface of both the B7-H4 transfected cell line and the B7-H4 positive breast cancer cell line SK-BR-3.
Figure 11B:
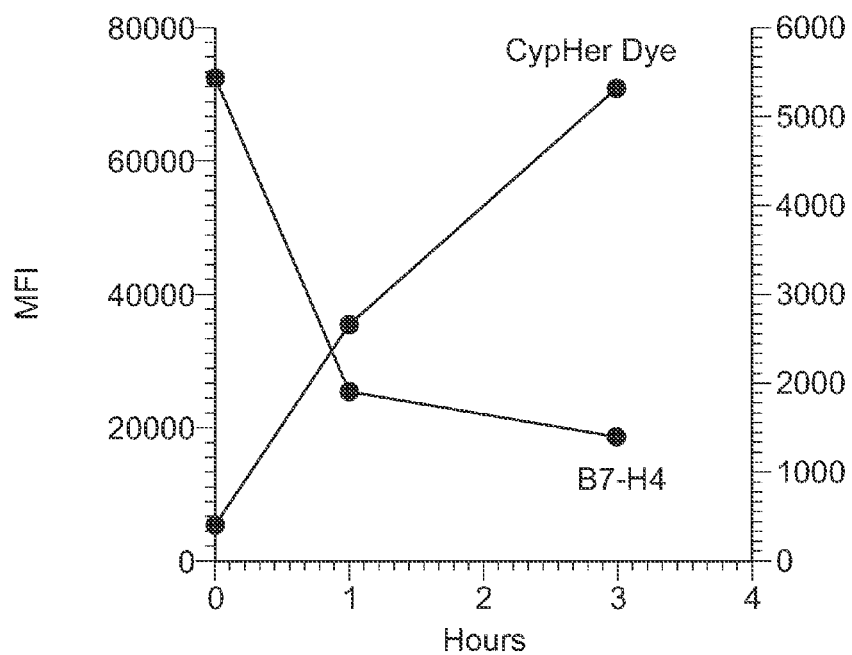

As shown in FIG. 9, antibody 6H3 was found to provide the greatest blockage of B7-H4 Ig mediated suppression of T cell activation.

The abilities of the anti-human B7-H4 antibodies to reverse monocyte-mediated suppression was compared, and the cytokines produced by T cells was measured. IFN-γ primed monocytes from healthy donors were incubated with anti-B7-H4 antibody, anti-B7-H1 antibody, anti-PD-1 antibody, or a negative control antibody. Autologous T cells were activated with anti-CD3 antibody and co-incubated with the pre-treated monocytes at a ratio of 10 T cells per 1 macrophage, in the presence of antibody. The T cells were harvested and stained for CD4 and CD8, and were intracellularly stained for IL-2, TNF-α and IL-8. FIGS. 10A-10F show the results of this experiment. Antibody 6H3 was found to elicit the highest expression of IL-2, TNF-α and IL-8. Incubation of the primed monocytes in the presence of the negative control antibody resulted in significant monocyte suppression. In the absence of monocytes there is no suppression of T cell activity.

Example 4

Anti-Human B7-H4 Antibody 6H3 Induces Cell Surface Internalization of B7-H4

Materials and Methods

In order to demonstrate the ability of anti-human B7-H4 antibody 6H3 to induce the internalization of B7-H4 expressed on the surface of cells (i.e., membrane-bound B7-H4), antibody 6H3 and a control antibody were labeled with CypHer5E NHS Ester (a pH-sensitive cyanine dye that emits maximal fluorescence at acidic lysosomal compartment upon internalization). The CypHer5E-labeled 6H3 antibody was incubated with a stable HEK 293T cell line expressing human B7-H4 (293T.hB7-H4) or with cells of the B7-H4 positive breast cancer tumor cell line, SK-BR-3 (ATCC), for various times. Antibody internalization was measured as an increase in CypHer5E fluorescence determined by flow cytometry, using a BD FACS Canto II instrument.

Results

Figure 12A:
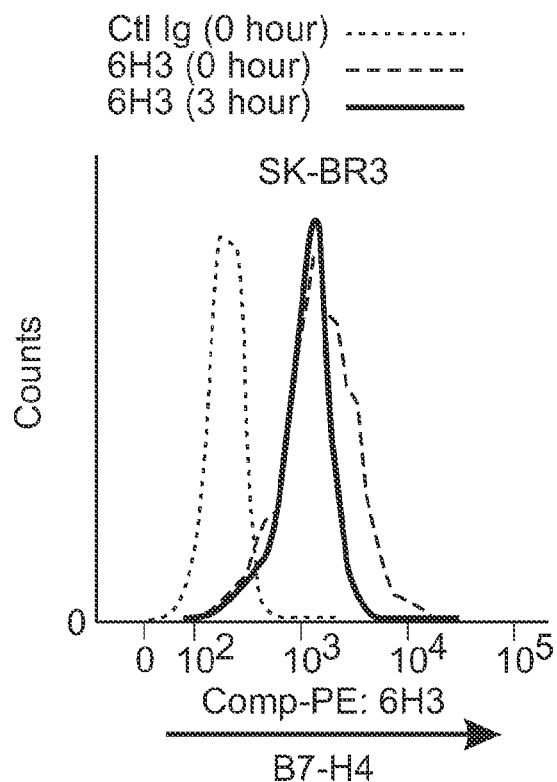
FIGS. 12A-12B are histograms showing B7-H4 surface staining and CypHer fluorescence relative to control on the B7-H4 positive human breast cancer cell line SK-BR3 cells over time during an incubation with CypHer labeled 6H3.
Figure 12B:
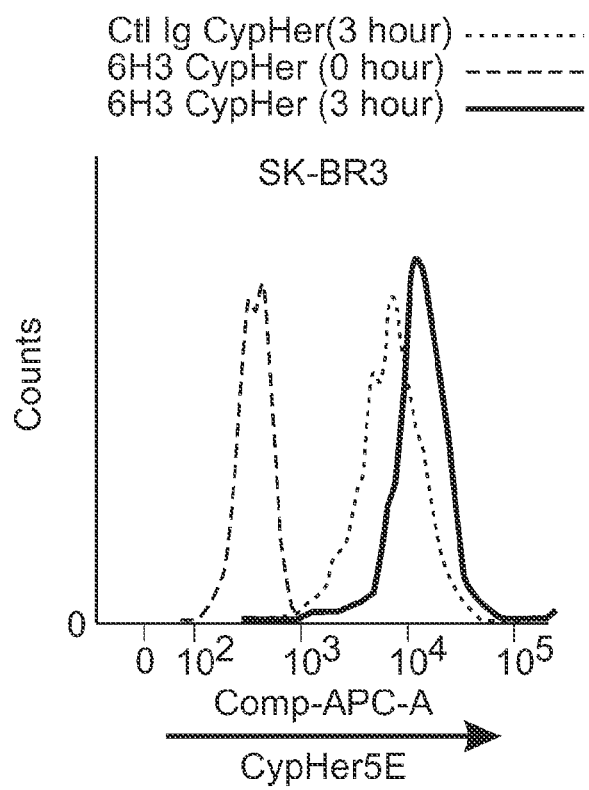

The results of this investigation are shown in FIGS. 11A-11B and FIGS. 12A-12B, and reveal that antibody 6H3 induced robust internalization of B7-H4 expressed on the surface of both the B7-H4 transfected cell line and the B7-H4 positive breast cancer cell line SK-BR-3. Such internalization decreased surface B7-H4 levels of both cell lines. The results confirm that antibody 6H3 can be used to target B7-H4 positive tumors, tumor cells or tumor-associated macrophages (TAMs) to reduce their respective B7-H4 surface levels and to inhibit tumor or TAM B7-H4 mediated immune suppression. The results additionally confirm that conjugates (e.g., drug toxin conjugates, etc.) of antibody 6H3 can be employed to selectively target and kill B7-H4 positive tumors, tumor cells and tumor-associated macrophages (TAMs). FIGS. 12A-12B are histograms showing B7-H4 surface staining and CypHer fluorescence relative to control on the B7-H4 positive human breast cancer cell line SK-BR3 cells over time during an incubation with CypHer labeled 6H3.

Example 5

Anti-Human B7-H4 Antibody 6H3 Is Capable of Staining B7-H4 Positive Cells by IHC Materials and Methods B7-H4 expression in human tissue specimens was evaluated by IHC using clone 6H3 and detected using alkaline peroxidase and DAB; slides were read by a pathologist. Slides from the same specimens were also stained using hematoxylin and eosin stain (H+E), the most widely used stain in medical diagnosis.

Results

Figure 13A:
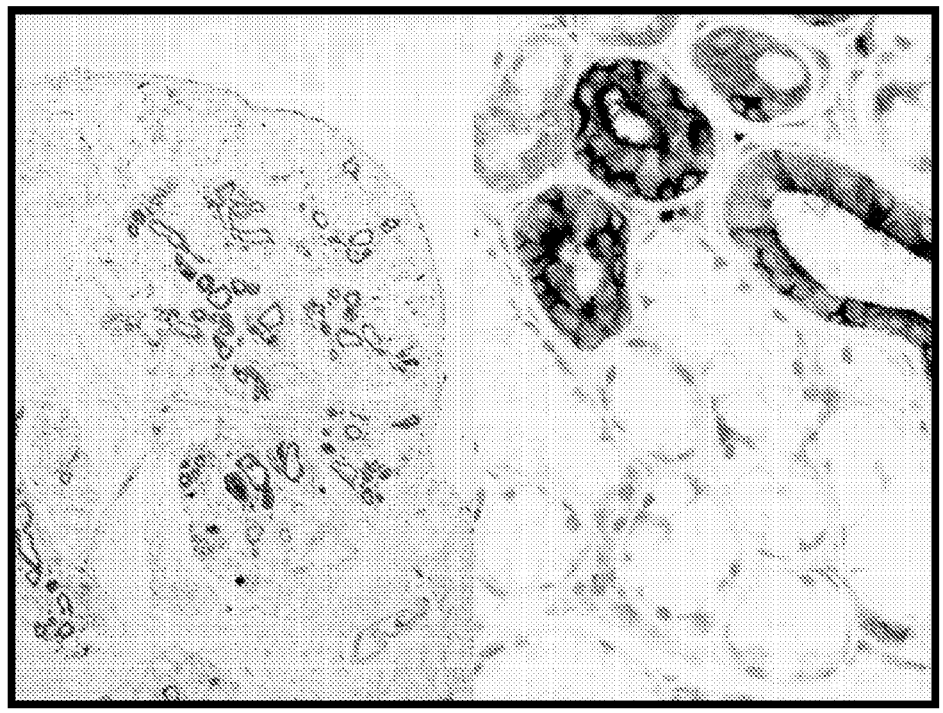
FIGS. 13A-13C are photomicrographs showing the ability of antibody 6H3 to detect B7-H4 positive tumor cells of histological specimens.
Figure 13B:
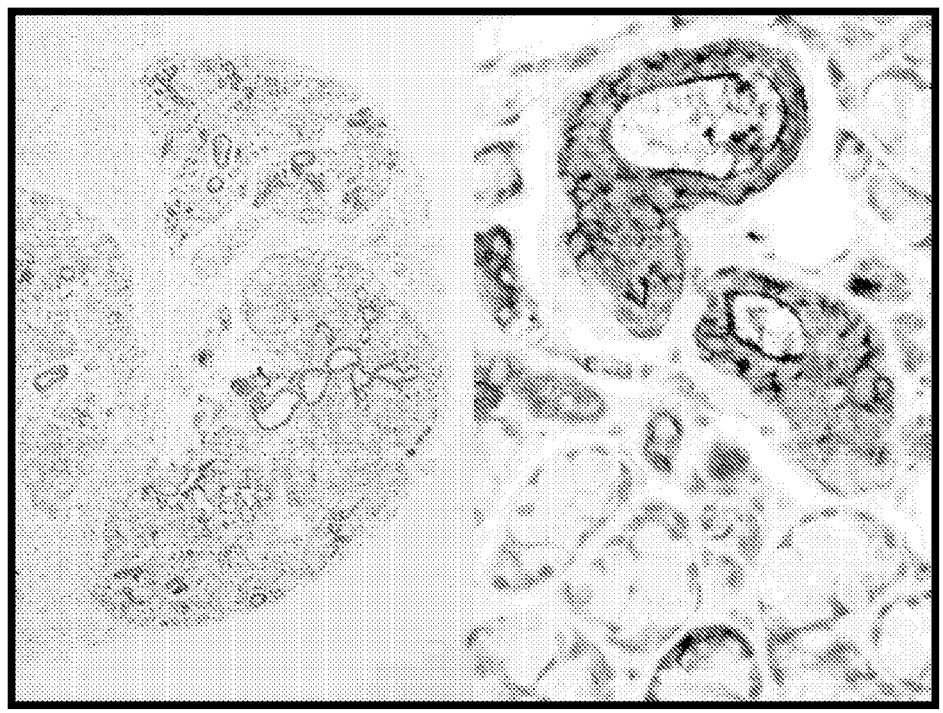
Figure 13C:
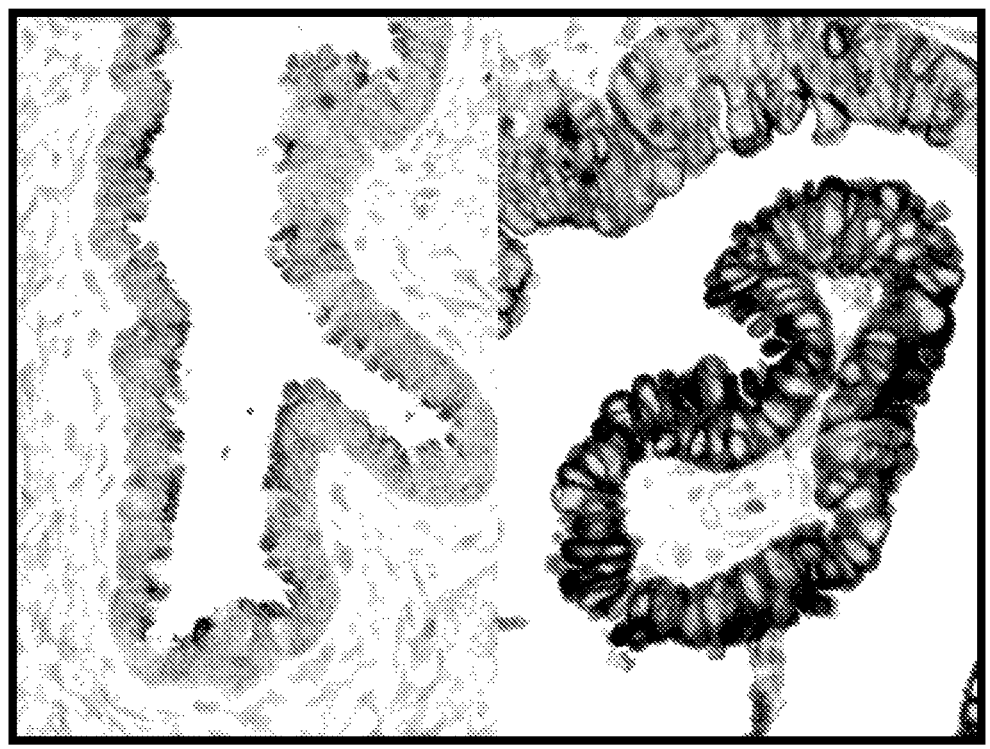

In order to demonstrate the ability of anti-human B7-H4 antibody 6H3 to detect B7-H4 positive cells, the antibody was labeled and incubated in the presence of tissue. FIGS. 13A-13C show the ability of the antibody to detect B7-H4 positive tumor cells of specimens that had looked normal when the tissue had been stained with (H+E). FIGS. 13A and 13B are images of 6H3-stained salivary gland tissue that looked normal on H+E staining. B7-H4 seems to be most strongly expressed by ductal epithelial cells (best seen at the top right of both images). There is little expression by acinar cells (on the bottom right). FIG. 13C shows two different but related serous cystic lesions of the ovary. The left panel is benign (a serous cystadenoma), and the right panel is a malignant serous cystadenocarcinoma. In both panels, the epithelium expresses B7-H4, but the malignant counterpart is more intense than in the benign tumor where the expression appears to be accentuated on the luminal surface; such increased intensity is believed to reflect the overexpression of B7-H4.

Example 6

Humanization of Anti-Human B7-H4 Antibody 6H3

Murine anti-B7-H4 antibody 6H3 was humanized using a process that included generating a homology modeled antibody 3D structure and creating a profile of the parental antibody based on structure modeling. A set of humanized heavy and light chain variable region sequences were generated, each of which combined specific regions of the parental antibody sequence with the majority of the human framework sequence. A total of 6 humanized heavy chain sequences and 6 humanized light chain sequences were produced.

Sequence alignments comparing the variable domains of murine antibody 6H3 to the human germline and rearranged framework sequence database were generated using Geneious. Preferred acceptor frameworks were identified based on the overall sequence identity across the framework, matching interface position, similarly classed CDR canonical positions, and presence of N-glycosylation sites that would have to be removed.

A structural model of the murine antibody 6H3 variable light and heavy chains was generated in Discovery Studio. Template structures were identified by searching the PDB database with the 6H3 light chain and heavy chain variable domain sequences with and without their CDRs. The alignment of the 6H3 sequences to the templates and modeling the structures based on homology were carried out using MODELLER (Sali, A. et al. (1993) *"Comparative Protein Modelling By Satisfaction Of Spatial Restraints,"* J. Molec. Biol. 234(3):779-815).

A number of hybrid sequences that combined different regions of the parental antibody sequence with that of the human frameworks were systematically analyzed using the 3D model to identify the hybrid sequences that were predicted to have the least impact on the defined structure of the CDRs (Chothia, C. et al. (1987) *"Canonical Structures For The Hypervariable Regions Of Immunoglobulins,"* J. Mol. Biol. 196:901-917; Martin, A. C. et al. (1996) *"Structural Families In Loops Of Homologous Proteins: Automatic Classification, Modelling And Application To Antibodies,"* J. Molec. Biol. 263(5):800-815). Particular attention was given to hybrid sequences that contained amino acids from the human framework that were within 5 Å of CDR loops, in the Vernier zone, in the VH/VL interchain interface, or in CDR canonical class determining positions, as these hybrid sequences are judged more likely to have a detrimental effect on the function of the resulting humanized antibody.

antigen binding. The goal was to maximize the amount of human sequence in the final humanized antibody while retaining the original antibody specificity.

Sequence alignments comparing murine 6H3 antibody variable domains to the human germline database were generated. Based on the overall sequence identity, matching interface position, and similarly classed CDR canonical positions, the germline family IGKV2-30*02 was identified as a possible acceptor framework for the light chain. The J-segment genes were compared to the parental sequence over FR4 and J-segments, and IGKJ4*01 was selected for the light chain. A rearranged human kappa light chain, CAA85590, was identified as a second possible acceptor framework after aligning the parental variable light chain to the non-redundant database. Alignment of the parental (6H3) variable light chain to these acceptor frameworks is shown in Table 5, with non-identical residues shown underlined.

TABLE 5

| Variable Light Chain | SEQ ID # | Sequence | | | |
|---|---|---|---|---|---|
| | | 10 | 20 | 30 | 40 |
| Murine 6H3 | 3 | DVVMTQTPLS | LPVSLGDQAS | ISCRSSQSLV | HINGNTYLHW |
| IGKV2-30*02 IGKJ4*01 | 14 | DVVMTQSPLS | LPVTLGQPAS | ISCRSSQSLV | HSDGNTYLNW |
| CAA85590 | 15 | DIVMTQTPLS | LPVTLGQPAS | ISCRSSRGLV | HSDGNTYLNW |
| | | 50 | 60 | 70 | 80 |
| Murine 6H3 | 3 | YLQKPGQSPK | VLIYKVSNRF | SGVPDRFSGS | GSGTDFTLKI |
| IGKV2-30*02 IGKJ4*01 | 14 | FQQRPGQSPR | RLIYKVSNRD | SGVPDRFSGS | GSGTDFTLKI |
| CAA85590 | 15 | FQQRPGQSPR | RLIYKVSNRD | SGVPDRFSGS | GSGADFTLKI |
| | | 90 | 100 | 110 | 112 |
| Murine 6H3 | 3 | SRVEAEDLGV | YFCSQSTHVP | LTFGAGTKLE | LK |
| IGKV2-30*02 IGKJ4*01 | 14 | SRVEAEDVGV | YYCMQGTHWP | LTFGGGTKVE | IK |
| CAA85590 | 15 | SRVEAEDVGV | YYCMQSIHWP | WTFGQGTKVE | IK |

A profile of the parental antibody was created based on CDR analysis and structure modeling. Human acceptor frameworks were identified based on sequence and homology comparisons. Humanized antibodies were designed by creating multiple hybrid sequences that fuse parts of the parental antibody sequence with the human framework sequences. Using the 3D model, these humanized sequences were methodically analyzed by eye and by computer modeling to isolate the sequences that would most likely retain The heavy chain of murine antibody 6H3 was found to be most similar to the germline IGHV1-46*03. The J segment genes were compared to the murine 6H3 heavy chain sequence over FR4 and J-segments, and IGHJ4*01 was selected for the heavy chain. A rearranged human kappa light chain, ABF83259, was identified as a second possible acceptor framework after aligning parental VL to the non-redundant database. Alignment of the murine variable heavy chain to these acceptor frameworks is shown in Table 6.

TABLE 6

| Variable Heavy Chain | SEQ ID # | Sequence | | | |
|---|---|---|---|---|---|
| | | 10 | 20 | 30 | 40 |
| Murine 6H3 | 5 | EVQLQQSGPV | LVKPGTSVKM | SCKASGYTFT | DYYMNWVKQS |
| IGHV1-46*03 IGHJ4*01 | 16 | QVQLVQSGAE | VKKPGASVKV | SCKASGYTFT | SYYMHWVRQA |

TABLE 6-continued

| Variable Heavy Chain | SEQ ID # | Sequence |
|---|---|---|
| ABF83259 | 17 | QVQLVQSGAE MKKPGASVKV SCKASGYTFT DYVIHWVRQA |
| | | 50          60          70          80 |
| Murine 6H3 | 5 | HGKSLEWIGV INPYNGDTTY NQKFKGKATL TVDKSSSTAY |
| IGHV1-46*03 IGHJ4*01 | 16 | PGQGLEWMGI INPSGGSTSY AQKFQGRVTM TRDTSTSTVY |
| ABF83259 | 17 | PGQSLEWMGW INPGDGDTKY SQKFQGRVTV ARDTSATTAY |
| | | 90         100         110         115 |
| Murine 6H3 | 5 | MEVNSLTFED SAVYYCARYP ES TYWGQGTL VTVSA |
| IGHV1-46*03 IGHJ4*01 | 16 | MELSSLRSED TAVYYCARYF D___YWGQGTL VTVSS |
| ABF83259 | 17 | MELSSLRSED TAVYYCARAS TGHVYWGQGTL VTVSS |

For the light chain, three humanized chains were created for each of the two acceptor frameworks IGKV2-30*02 IGKJ4*01 and CAA85590, to thereby form six humanized 6H3 light chains. The first humanized chain for each acceptor framework (VL1A, VL2A) contains the most human framework (Humanized Light Chain 1). The second humanized chain for each acceptor framework (VL1B, VL2B) contains some amount of parental sequence fused with the human framework sequence, which should help retain the original CDR conformation (Humanized Light Chain 2). The third humanized chain for each of the acceptor frameworks (VL1C, VL2C) contains even more parental sequence fused with the human framework, which should help maintain the original antibody specificity and CDR structure (Humanized Light Chain 3). The amino acid sequences of these chains are as indicated below.

Amino Acid Sequences of the Light Chain Variable Region of the humanized variants of anti-human B7-H4 antibody 6H3, as derived from the IGKV2-30*02 IGKJ4*01 acceptor framework (CDRs are shown underlined):

1. VL1A IGKV2-30*02 IGKJ4*01 (Humanized 1):
(SEQ ID NO: 18)
DVVMTQSPLS LPVTLGQPAS ISCRSSQSLV HINGNTYLNW
FQQRPGQSPR

RLIYKVSNRD SGVPDRFSGS GSGTDFTLKI SRVEAEDVGV
YYCSQSTHVP

LTFGGGTKVE IK

2. VL1B IGKV2-30*02 IGKJ4*01 (Humanized 2):
(SEQ ID NO: 19)
DVVMTQSPLS LPVTLGQPAS ISCRSSQSLV HINGNTYLHW
YQQRPGQSPR

VLIYKVSNRF SGVPDRFSGS GSGTDFTLKI SRVEAEDVGV
YFCSQSTHVP

LTFGGGTKVE IK

3. VL1C IGKV2-30*02 IGKJ4*01 (Humanized 3):
(SEQ ID NO: 20)
DVVMTQSPLS LPVTLGQPAS ISCRSSQSLV HINGNTYLHW
YLQRPGQSPK

VLIYKVSNRF SGVPDRFSGS GSGTDFTLKI SRVEAEDVGV
YFCSQSTHVP

LTFGGGTKVE IK

Amino Acid Sequences of the Light Chain Variable Region of the humanized variants of anti-human B7-H4 antibody 6H3, as derived from the CAA85590 acceptor framework (CDRs are shown underlined):

1. VL2A CAA85590 (Humanized 1):
(SEQ ID NO: 21)
DIVMTQTPLS LPVTLGQPAS ISCRSSQSLV HINGNTYLNW
FQQRPGQSPR

RLIYKVSNRD SGVPDRFSGS GSGADFTLKI SRVEAEDVGV
YYCSQSTHVP

LTFGQGTKVE IK

2. VL2B CAA85590 (Humanized 2):
(SEQ ID NO: 22)
DIVMTQTPLS LPVTLGQPAS ISCRSSQSLV HINGNTYLHW
YQQRPGQSPR

VLIYKVSNRF SGVPDRFSGS GSGTDFTLKI SRVEAEDVGV
YFCSQSTHVP

LTFGQGTKVE IK

3. VL2C CAA85590 (Humanized 3):
(SEQ ID NO: 23)
DIVMTQTPLS LPVTLGQPAS ISCRSSQSLV HINGNTYLHW
YLQRPGQSPK

VLIYKVSNRF SGVPDRFSGS GSGTDFTLKI SRVEAEDVGV
YFCSQSTHVP

LTFGAGTKVE IK

For the heavy chain, three humanized chains were created for each of the IGHV1-46*03 IGHJ4*01 and ABF83259 acceptor frameworks identified above. In a similar fashion to the light chain, the first humanized chain for each acceptor framework (VH1A, VH2A) contains the most human sequence (Humanized 1). The second humanized chain for each acceptor framework (VH1B, VH2B) should help retain the original CDR conformation (Humanized 2). The third chain for each of the acceptor frameworks (VH1C, VH2C) should help maintain the original antibody specificity and CDR structure (Humanized 3). The amino acid sequences of these chains are as indicated below.

Amino Acid Sequences of the Heavy Chain Variable Region of the humanized variants of anti-human B7-H4 antibody 6H3, as derived from the IGHV1-46*03 IGHJ4*01 acceptor framework (CDRs are shown underlined):

1. VH1A IGHV1-46*03 IGHJ4*01 (Humanized 1):
(SEQ ID NO: 24)
QVQLVQSGAE VKKPGASVKV SCKASGYTFT DYYMHWVRQA
PGQGLEWMGI

INPYNGDTSY AQKFQGRVTM TRDTSTSTVY MELSSLRSED
TAVYYCARYP

ESTYWGQGTL VTVSS

2. VH1B IGHV1-46*03 IGHJ4*01 (Humanized 2):
(SEQ ID NO: 25)
EVQLVQSGAE VKKPGASVKV SCKASGYTFT DYYMNWVRQA
PGQGLEWMGI

INPYNGDTSY NQKFQGRVTL TVDKSTSTVY MELSSLRSED
TAVYYCARYP

ESTYWGQGTL VTVSS

3. VH1C IGHV1-46*03 IGHJ4*01 (Humanized 3):
(SEQ ID NO: 26)
EVQLVQSGAE VKKPGASVKV SCKASGYTFT DYYMNWVRQA
PGQGLEWIGI

INPYNGDTSY NQKFKGRVTL TVDKSTSTAY MELSSLRSED
TAVYYCARYP

ESTYWGQGTL VTVSS

Amino Acid Sequences of the Heavy Chain Variable Region of the humanized variants of anti-human B7-H4 antibody 6H3, as derived from the ABF83259 acceptor framework (CDRs are shown underlined):

1. VH2A ABF83259 (Humanized 1):
(SEQ ID NO: 27)
QVQLVQSGAE MKKPGASVKV SCKASGYTFT DYYIHWVRQA
PGQSLEWMGW

INPYNGDTKY SQKFQGRVTV ARDTSATTAY MELSSLRSED
TAVYYCARYP

ESTYWGQGTL VTVSS

2. VH2B ABF83259 (Humanized 2):
(SEQ ID NO: 28)
EVQLVQSGAE MKKPGASVKV SCKASGYTFT DYYMNWVRQA
PGQSLEWMGV

INPYNGDTTY NQKFQGRVTV AVDKSATTAY MELSSLRSED
TAVYYCARYP

ESTYWGQGTL VTVSS

3. VH2C ABF83259 (Humanized 3):
(SEQ ID NO: 29)
EVQLVQSGAE MKKPGASVKV SCKASGYTFT DYYMNWVRQA
PGQSLEWIGV

INPYNGDTTY NQKFQGRVTV TVDKSATTAY MELSSLRSED
TAVYYCARYP

ESTYWGQGTL VTVSS

The antibodies, and their antigen-binding fragments disclosed herein include any of the 36 combinations of the disclosed humanized variants of anti-human B7-H4 antibody 6H3. Specifically, such antibodies include the combinations shown in Table 1.

Twenty out of thirty-six humanized variants constructed retained binding specificity to human B7-H4. Six additional heavy chain and light chain combo that bind B7-H4 but are not further pursued in functional assays are:

(SEQ ID NO: 24, SEQ ID NO: 20)
H1A L1C, (SEQ ID NO: 24, SEQ ID NO: 23)
H1A L2C, (SEQ ID NO: 25, SEQ ID NO: 19)
H1B L1B, (SEQ ID NO: 25, SEQ ID NO: 20)
H1B L1C, (SEQ ID NO: 25, SEQ ID NO: 22)
H1B L2B
and (SEQ ID NO: 25, SEQ ID NO: 23)
H1B L2C Example 7

Chimeric and Humanized 6H3 Antibodies are Internalized by Cells

Materials and Methods

Chimeric and Humanized Variants of Anti-B7-H4 Antibody 6H3

Chimeric 6H3 (also referred to as human chimeric 6H3, c6H3 and hc6H3) in the Examples below refers to chimeric 6H3 antibody including mouse light and heavy chain variable regions (SEQ ID NOS:3 and 5) and constant regions from the human IgG1 heavy chain and human κ light chain.

Humanized variants of 6H3 having the light chain variable region and heavy chain variable region combinations of Table 7 were prepared and are referred to as variants 1-14 (also referred to as V1-V14) in the Examples below.

TABLE 7

Humanized Variants of Anti-B7-H4 Antibody 6H3

| Variant # | Heavy Chain | | Light Chain | |
|---|---|---|---|---|
| 1 | H1A | SEQ ID NO:24 | L1B | SEQ ID NO:19 |
| 2 | H1C | SEQ ID NO:26 | L1B | SEQ ID NO:19 |
| 3 | H2B | SEQ ID NO:28 | L1B | SEQ ID NO:19 |
| 4 | H2C | SEQ ID NO:29 | L1B | SEQ ID NO:19 |
| 5 | H1C | SEQ ID NO:26 | L1C | SEQ ID NO:20 |
| 6 | H2B | SEQ ID NO:28 | L1C | SEQ ID NO:20 |
| 7 | H2C | SEQ ID NO:29 | L1C | SEQ ID NO:20 |
| 8 | H1A | SEQ ID NO:24 | L2B | SEQ ID NO:22 |
| 9 | H1C | SEQ ID NO:26 | L2B | SEQ ID NO:22 |
| 10 | H2B | SEQ ID NO:28 | L2B | SEQ ID NO:22 |
| 11 | H2C | SEQ ID NO:29 | L2B | SEQ ID NO:22 |
| 12 | H1C | SEQ ID NO:26 | L2C | SEQ ID NO:23 |
| 13 | H2B | SEQ ID NO:28 | L2C | SEQ ID NO:23 |
| 14 | H2C | SEQ ID NO:29 | L2C | SEQ ID NO:23 |

Internalization Assays
EG7 Cells

Chimeric 6H3 and humanized 6H3 variants labeled with the pH-sensitive fluor CypHER-5 were tested for internalization into EG7 (B7-H4 negative cells), EG7.IG7 (B7-H4 low expressing cells), and EG7.IVB3 (B7-H4 high expressing cells)

Cells were treated according to the following conditions: 4° C., 0.1% azide, 30 min (favoring "no" internalization); 4° C., 30 min; or 37° C.; 4 hr (favoring internalizing) and analyzed by flow cytometry.

624Mel/hB7-H4 Stable Lines

Chimeric anti-B7-H4 antibodies (c2E11, c2H9, c2D1, c6H3) and human variant anti-B7-H4 antibody internalization was also examined in 624mel/hB7-H4 stable cell lines. Briefly, cells were pulsed with CypHer5-labeled anti-B7-H4 antibodies (10 µg/ml) for 30 minutes, washed once to remove unbound probe and incubated at 37° C. for 4 hours. Cell surface B7-H4 expression and antibody internalization were measured by flow cytometry.

CT26/hB7-H4 Stable Cell Line—Clone E4F2

Anti-B7-H4 antibody internalization was also examined in the CT26/hB7-H4 stable cell line—clone E4F2. Briefly, 100,000 cells were labeled at 37° C. for four hours with CypHer5-labeled anti-B7-H4 antibodies (2 µg/ml). The cells were pretreated with 0.1% sodium azide for 30 minutes on ice. These cells were then labeled at 4° C. for four hours with CypHer5-labeled anti-B7-H4 antibodies containing 0.1% azide. After the incubation period, all cells were pelleted, resuspended in Fc blocking medium, and stained with PE labeled anti-B7-H4 antibody (H74) in order to measure B7-H4 levels on the cell surface. Cells were then washed and stained with the Live/Dead nearIR viability dye.

Mouse 6H3.m1 (Mouse IgG1) and 6H3.m2a (Mouse IgG2a) mAbs

Anti-B7-H4 antibody internalization, including mouse 6H3.m1 (mouse IgG1) and 6H3.m2a (mouse IgG2a) mAbs internalization, was also examined in the CT26/hB7-H4 and E.G7ova/hB7-H4 stable cell lines. Briefly, 100K cells were labeled at 37° C. for four hours with CypHer5-labeled anti-B7-H4 antibodies (2 µg/ml) in medium. Prior to being labeled, cells were Fc-receptor blocked with 10 µg mouse IgG for 10 minutes. Cells were then pelleted, washed and stained with PE labeled anti-B7-H4 antibody (H74) in order to measure B7-H4 levels on the cell surface. Finally, cells were washed, stained with the Live/Dead™ nIR viability dye and fixed.

Internalization Study Using a Confocal Microscope

B7-H4 mAb chimeric 6H3, chimeric 2E11, chimeric 2H9, chimeric 2D1, 6H3 humanized variants V2, V6, V7, V9, V12, and V14 were labeled with CypHer5E NHS Ester, a pH-sensitive cyanine dye, which emits maximal fluorescence at acidic lysosomal compartment upon internalization. 1 µg/ml CypHer5E-labeled 6H3, 2E11, 2H9, 2D1 or 6H3 humanized variants V2, V6, V7, V9, V12 and V14 was incubated with 293T.hB7-H4 or B7-H4 positive breast cancer tumor cell line SK-BR-3 for various times and monitored for internalization by a confocal fluorescence microscope (Perkin Elmer Operetta) (data not shown).

Results

Chimeric 6H3 was internalized at levels above negative control by both EG7.IG7 (B7-H4 low expressing cells) and EG7.IVB3 (B7-H4 high expressing cells) during in a staining protocol that favored internalization (37° C., 4 hr).

Chimeric 6H3 was internalized by cells even under conditions that should prevent internalization. For example, chimeric 6H3 was internalized at levels above negative control antibody in EG7.IVB3 (B7-H4 high expressing cells) at 4° C., 30 min—conditions that do not favor internalization.

Figure 14:
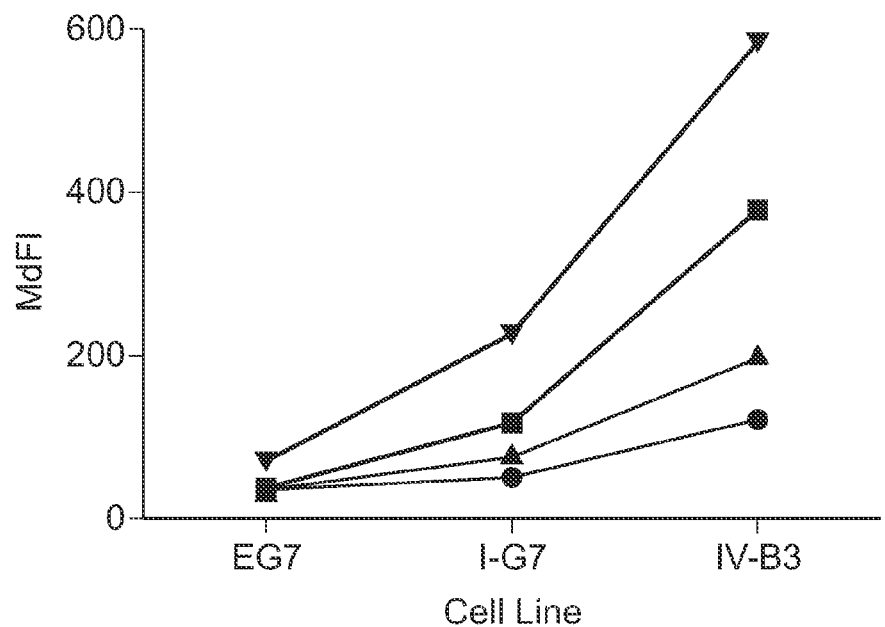
FIG. 14 is a line graph showing internalization of chimeric 2E11 (-●-), chimeric 2H9 (-■-), chimeric 2D1 (-▲-), and chimeric 6H3 (-▼-) in EG7 (B7-H4 negative cells), EG7.IG7 (B7-H4 low expressing cells) and EG7.IVB3 (B7-H4 high expressing cells) after treatment at 4° C. for 30 min.

Other chimeric anti-B7-H4 antibodies (c2E11, c2H9, c2D1), also showed some degree of internalization in EG7.IG7 (B7-H4 low expressing cells) and/or EG7.IVB3 (B7-H4 high expressing cells) after treatment at 4° C. for 30 min, however, chimeric 6H3 internalized to the greatest degree (FIG. 14).

Figure 15:
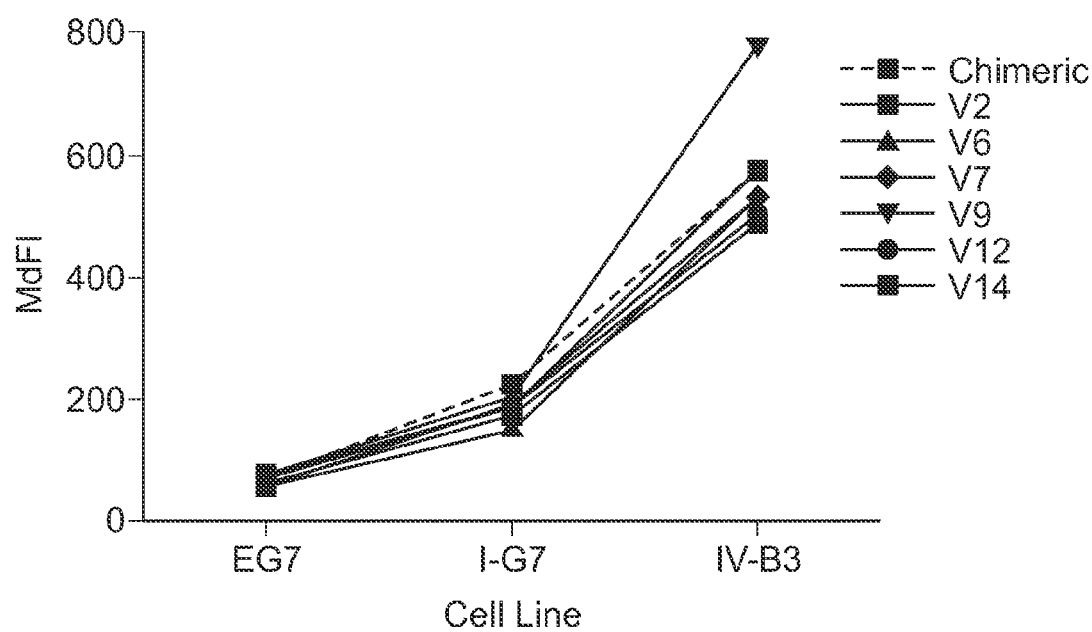
FIG. 15 is a line graph showing internalization of chimeric 6H3 (-●-), humanized Variant 2 (-▲-), humanized Variant 6 (-▲-), humanized Variant 7 (-▲-), humanized Variant 9 (-▲-), humanized Variant 12 (-▲-), and humanized Variant 14(-▲-) in EG7 (B7-H4 negative cells), EG7.IG7 (B7-H4 low expressing cells) and EG7.IVB3 (B7-H4 high expressing cells) after treatment at 4° C. for 30 min.

Six humanized variants were also tested in cell internalization assays. All six variants retained the ability to internalize. Variant 9 showed increased internalization relative to chimeric 6H3 and other variants tested (FIG. 15).

Anti-B7-H4 antibody internalization was also examined in 624mel/hB7-H4 stable cell lines. Cell surface expression levels of B7-H4 were established by flow cytometry. The 624mel cells express no B7-H4, Clone B7 express a low amount and Clone B6 express the highest amount. Internalization of CypHer5-labeled chimeric anti-B7-H4 mAbs (c2H9, c2D1 c6H3) was greater than negative control antibody (anti-PD-1 antibody) into 624Mel.B7H4 cells (clone B6). The degree of internalization correlated with the level of cell surface hB7-H4 expression. Among the chimeric anti-B7-H4 mAbs, c6H3 showed the most internalization. Internalization of CypHer5-labeled human variant anti-B7-H4 mAbs (V2, V6, V7, V9, V12 and V14) into 624Mel.B7H4 cells (clone B6) was similar to c6H3.

Figure 16:
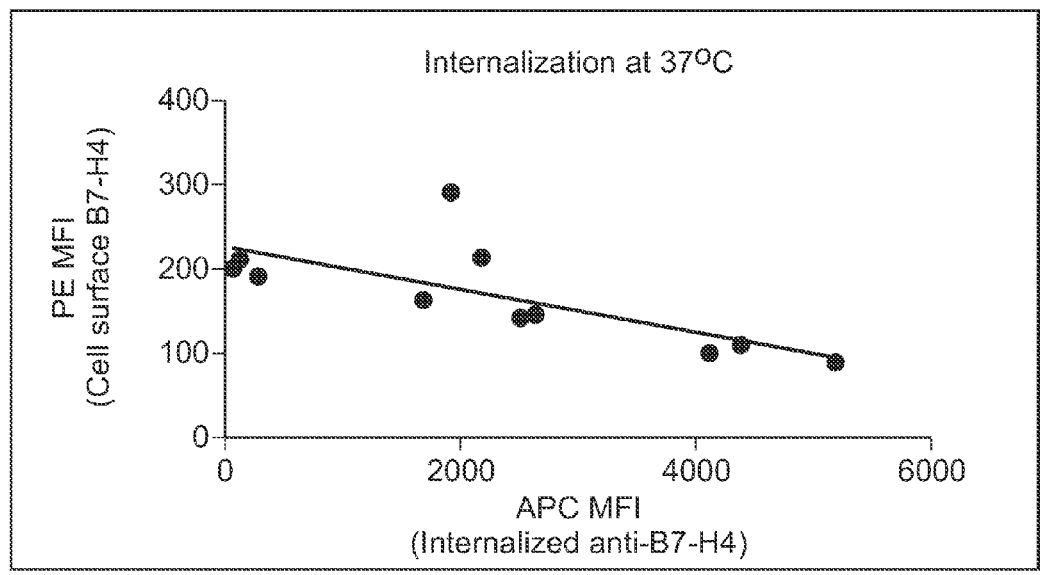
FIG. 16 is a line graph showing internalization of anti-B7-H4 antibody as a function of cell surface expression of B7-H4 under conditions that favor internalization.
Figure 17:
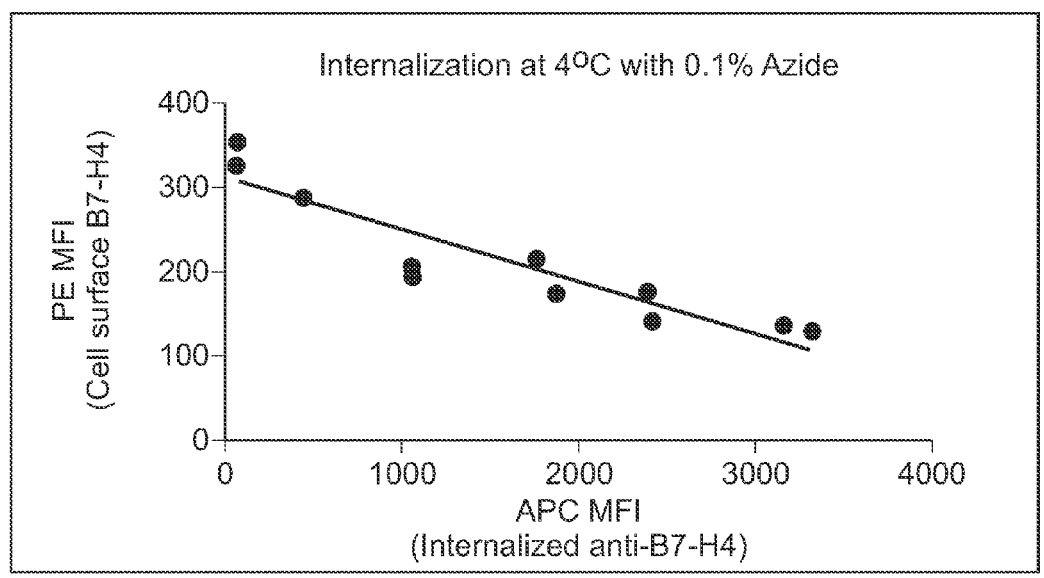
FIG. 17 is a line graph showing internalization of anti-B7-H4 antibody as a function of cell surface expression of B7-H4 under conditions that do not favor internalization.
Figure 21A:
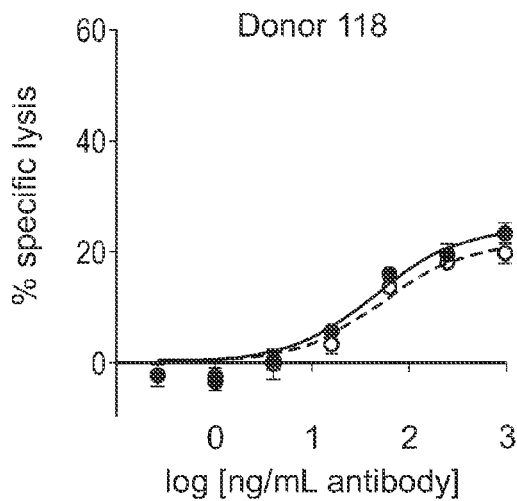
FIGS. 21A-21D are bar graphs showing % specific lysis of target cells with increasing concentrations of variant 11 or variant 14 humanized 6H3 antibodies (log [ng/mL antibody] in combination with peripheral blood mononucleated cell (PBMC) from four different donors as effector cells: donor 118 (FIG. 21A), donor 117 (FIG. 21B), donor 121 (FIG. 21C), or donor 122 (FIG. 21D) in an assay designed to measure antibody-dependent cell-mediated cytotoxicity (ADCC).
Figure 21B:
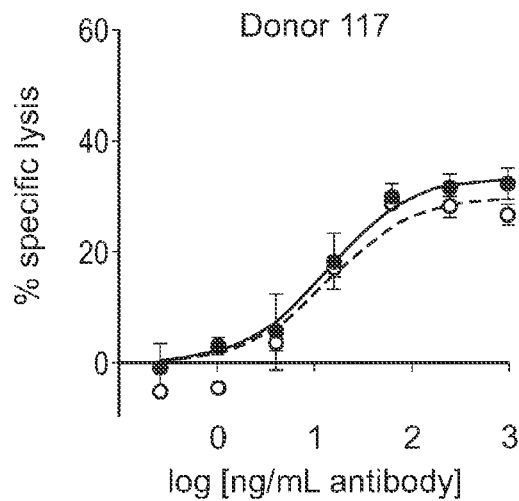
Figure 21C:
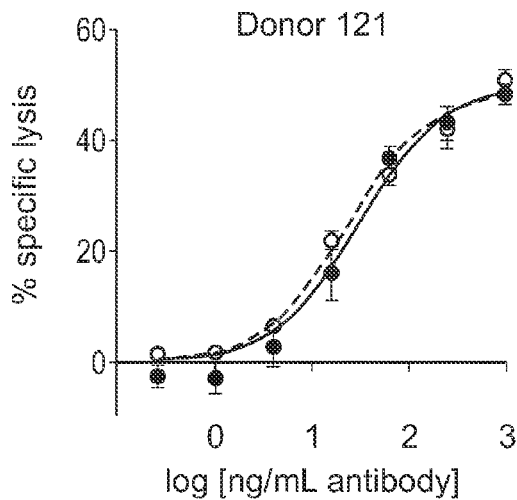
Figure 21D:
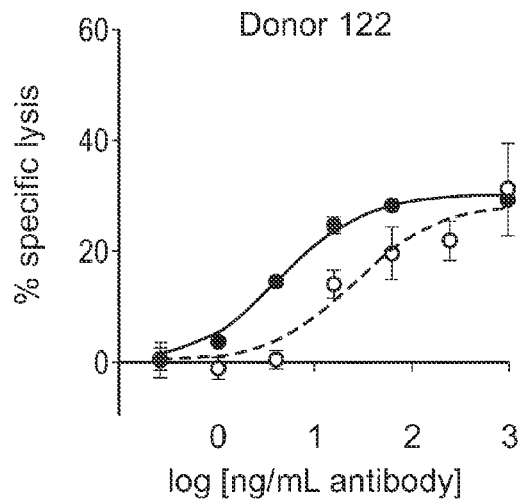

Anti-B7-H4 antibody internalization was also examined in the CT26/hB7-H4 stable cell line-clone E4F2. The chimeric anti-B7-H4 antibodies (c2H9, c2D1, c6H3, and to some degree c2E11) were internalized while negative control antibody (anti-PD-1 antibody) showed no internalization. Likewise, labeled human variant anti-B7-H4 mAbs (V2, V6, V7, V9, V12 and V14) were internalized while negative control antibody showed no internalization. The degree of internalization correlated with the level of cell surface hB7-H4 expression (FIG. 16). The amount of B7-H4 available on the cell surface after the incubation period was inversely proportional to the amount of antibody internalized. The anti-B7-H4 antibodies (c2H9, c2D1, c6H3, and variants V2, V6, V7, V9, V12 and V14) were also internalized under the 4° C.+azide conditions, though to a slightly lesser extent (FIGS. 16 and 17). It is unclear why these conditions failed to inhibit internalization to a greater degree. The CT26 parental cell line showed no internalization of anti-B7-H4 antibodies under these conditions.

Internalization assays were also conducted comparing internalization of mouse 6H3.m1 (mouse IgG1) and 6H3.m2a (mouse IgG2a) mAbs to chimeric 6H3 and humanize variants of 6H3 in CT26/hB7-H4 and E.G7ova/hB7-H4 stable cell lines. The anti-B7-H4 antibodies were internalized in both cell lines while the negative control (anti-PD-1 antibody) showed no internalization (FIGS. 18A and 18B). 6H3.m1 and 6H3.m2a internalize to a similar extent. Humanized variant 7 internalized most strongly, while variants 2, 9, and 12 internalize to a somewhat lesser extent. As observed above, the amount of B7-H4 available on the cell surface after the incubation period was generally inversely proportional to the amount of antibody internalized.

Using a confocal microscope, the internalization of 6H3 was visualized by punctate fluorescence within individual cells. Consistent with the internalization process, fluorescence signals accumulate near the plasma membrane at 5 hours, whereas at 24 hours the accumulation of fluorescent vesicles can clearly be seen in the large cytoplasmic region.

Using a confocal microscope, CypHerSE labeled 6H3 showed the best internalization capability among four chimeric B7-H4 mAbs (2E11, 2H9, 2D1, 6H3) after incubation with HEK293.hB7-H4 cells for five hours.

Using a confocal microscope, CypHerSE labeled 6H3 humanized variants V2, V6 and V7 showed the best internalization capability among six humanized 6H3 variants after incubation with HEK293.hB7-H4 cells for five hours. In contrast, CypHerSE labeled 6H3 humanized variants V6, V7 and V14 showed the best internalization capability among six humanized 6H3 variants after incubation with SK-BR-3 cells for five hours. Humanized 6H3 V6 and V7 are the top two best variants inducing internalization.

Example 8

Chimeric and Humanized Variants of 6H3 Induce Antibody-Dependent Cell-Mediated Cytotoxicity Materials and Methods ADCC Assays Antibody-Dependent Cell-Mediated Cytotoxicity (ADCC) assays were designed to test the ability of chimeric 6H3 and humanized variants of 6H3 to mediate target cell lysis by effector cells.

EG7.hB7-H4 (clone IVB3) cells and SK-BR-3 cells were tested as target cells. Peripheral blood mononuclear cells (PBMC) from four different healthy donors, referred to 117, 119, 121, and 122, were tested as effector cells.

Four different effector-to-target ratios were examined (e.g., E:T ratios of 100:1, 50:1, and 20:1).

A pilot experiment found that EL4-derived cells are highly sensitive to lysis by PBMC, and the assay was optimized to minimize this background. The incubation period for lysis in assays utilizing EG7.hB7-H4 was 4 hrs. The incubation period for lysis in assays utilizing SK-BR-3 cells was 20 hours.

Total lysis was measured by viability stain. Specific lysis=100×([% dead]anti-B7-H4 antibody treatment−[% dead]control IgG treatment)±(100−[% dead]control IgG treatment).

Results

In initial assay utilizing chimeric 6H3 and EG7.B7H4 target cells, specific lysis of target cells was detected for all four donors at all ratios tested. FIGS. 19A-19C illustrates results at 3 different effector cell:target cell ratios. 20:1 was selected for future assays as it best reflects in vivo ADCC activity.

The optimized assay conditions were employed to compare 14 humanization variants of 6H3 at a single concentration (10 ng/mL) (FIG. 20). Three of four effector cell donors (114, 120, 122) demonstrated specific lysis. Variants 4, 5, 8, and 11 displayed the highest ADCC activity. Out of the fourteen variants tested, variant 11 exhibited the highest ADCC activity, while variant 14 exhibited the lowest of ADCC activity. Dose titration experiments with variants 11 and 14 in combination with different donor/effector cells revealed that relative difference in antibody ADCC activity is donor specific (FIGS. 21A-21D).

In additional ADCC assays SK-BR-3 cells are used as target cells. It is believed that SK-BR-3 cells are a better mimic of in vivo target expression (transmembrane B7-H4) than the EG7.B7H4 cells used in the assays described above. Three different effector cell:target cell ratios were tested (20:1, 50:1, and 100:1) and two different effector cell donors (117 and 120) were tested in a dose titration of chimeric 6H3 antibody.

Figures 22A, 22B:
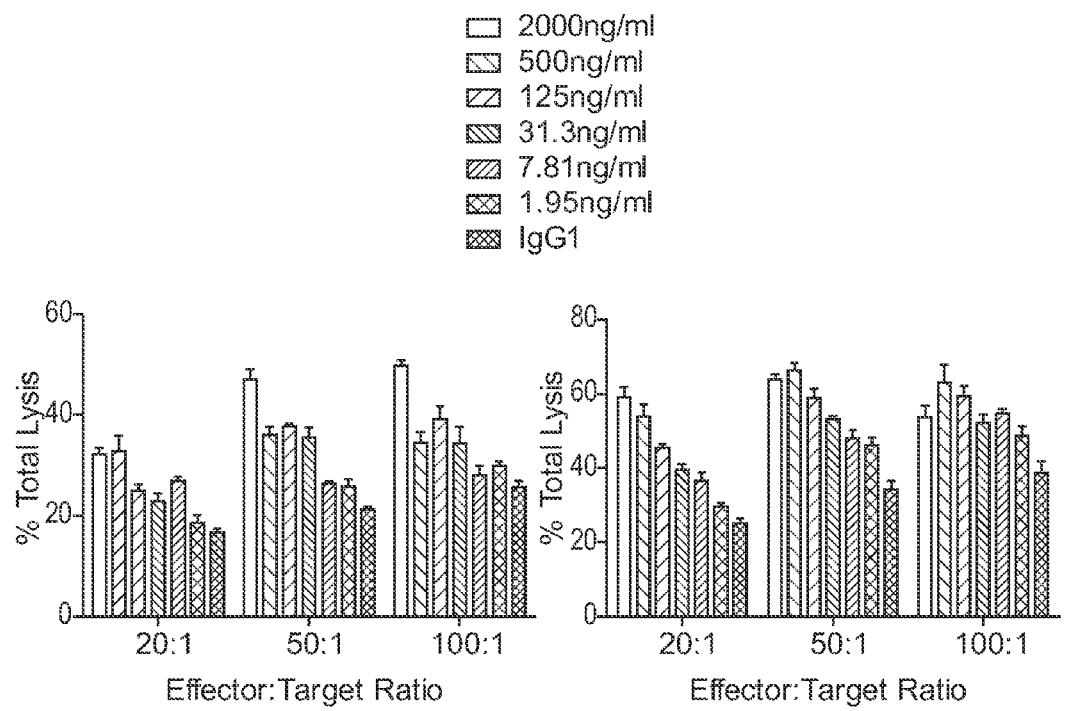
FIGS. 22A-22B are bar graphs showing the % total lysis of SK-BR-3 cells by 117 (FIG. 22A) or 120 (FIG. 22B) donor cells in the presence of control IgG1, or one of six different concentrations of chimeric 6H3 antibody (2000 ng/ml, 500 ng/ml, 125 ng/ml, 31.3 ng/ml, 7.81 ng/ml, 1.95 ng/ml) at three different effector cell:target cell ratios (20:1, 50:1, 100:1) in an assay designed to measure antibody-dependent cell-mediated cytotoxicity (ADCC).
Figures 23A, 23B:
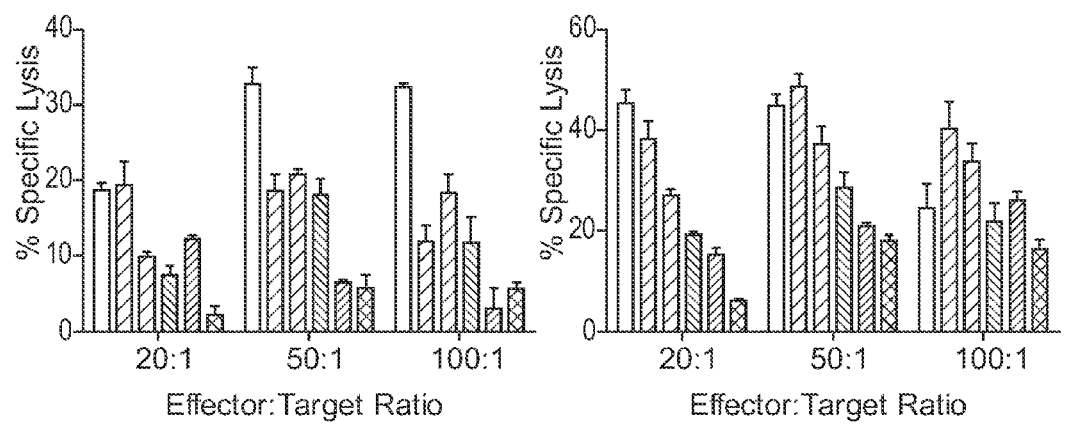
FIGS. 23A-23B are bar graphs showing the % specific lysis of SK-BR-3 cells by 117 (FIG. 23A) or 120 (FIG. 23B) donor cells in the presence of control IgG1, or one of six different concentrations of chimeric 6H3 antibody (2000 ng/ml, 500 ng/ml, 125 ng/ml, 31.3 ng/ml, 7.81 ng/ml, 1.95 ng/ml) at three different effector cell:target cell ratios (20:1, 50:1, 100:1) in an assay designed to measure antibody-dependent cell-mediated cytotoxicity (ADCC).

Total lysis (% of target cells that are Live/Dead dye positive) observed for both PBMC donors (117 and 120) was high (FIGS. 22A-22B). The assay was carried out for 20 hrs, and despite a high background, both donors exhibited specific lysis in an antibody dose-dependent fashion (FIGS. 23A-23B). 50:1 was determined to be the preferred effector:target ratio to observe dose-dependent activity for both donors.

Example 9

6H3 does not Induce Complement-Dependent Cytotoxicity

Materials and Methods

An assay was designed to test the ability of 6H3 antibodies to induce complement-dependent cytotoxicity (CDC). SK-BR-3 cells (ATCC) were utilized as targets. The target cells were mixed with neat or diluted normal human serum complement (Quidel) in the presence of 6H3 or control protein and the metabolic indicator dye AlamarBlue (Life Technologies). HERCEPTIN®(also a human IgG1 antibody) was used as a positive control and human IgG1 isotype control was used as a negative control. The relative fluorescence intensity of AlamarBlue (which is proportional to the number of viable cells) was measured using an EnVision plate reader (PerkinElmer).

Results

Figure 24A:
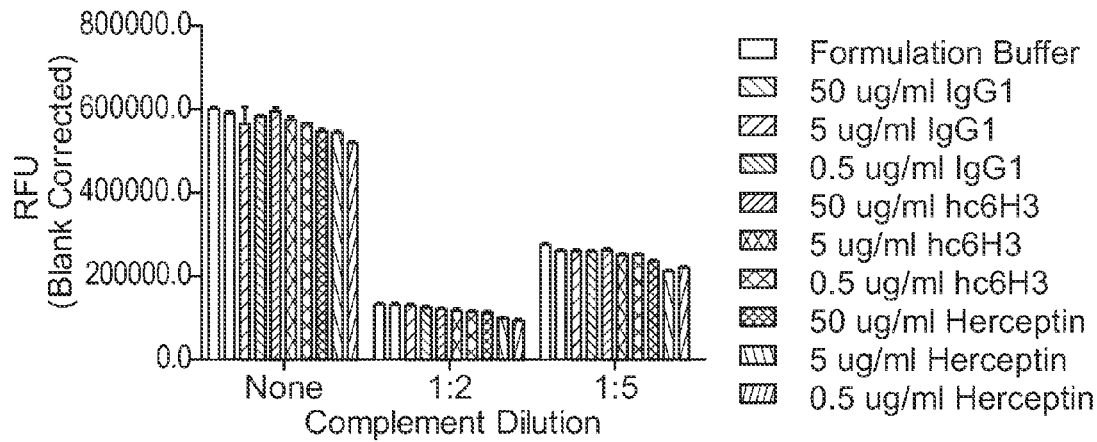
FIGS. 24A-24B are bar graphs showing the results of complement-dependent cytotoxicity assays utilizing control, chimeric 6H3 antibody and HERCEPTIN® antibody.
Figure 24B:
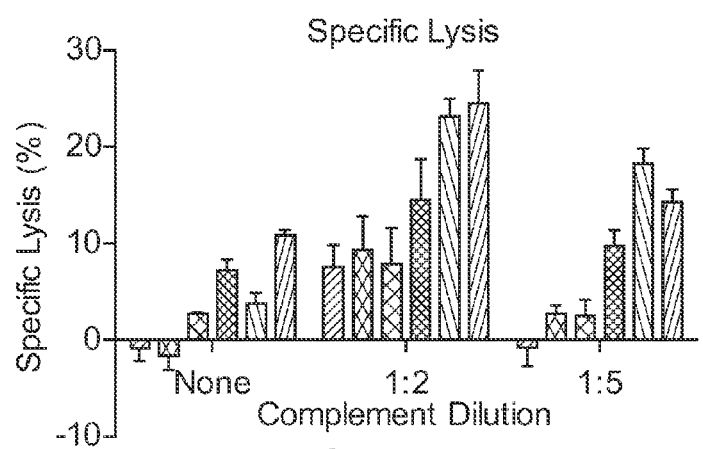

SK-BR-3 cells express complement resistance factors (e.g. CD46, CD55, CD59) therefore extremely high amounts of complement were utilized. HERCEPTIN®-mediated killing was observed using neat, 1:2, and 1:5-diluted complement. No CDC activity was observed for c6H3 under any condition tested (FIG. 24A-24B).

Example 10

6H3 Enhances CTL-mediated Lysis of B7-H4-Expressing Cells

Materials and Methods

CTL-mediated lysis assays utilize OT-1 TCR transgenic CD8 T cells than have been primed in vitro in the presence of APC pulsed with antigenic SIINFEKL (SEQ ID NO:30) peptide and supplemented with IL-2. The CTL are then coincubated at varying effector-to-target (E:T) ratios with fluorescently labeled target cells.

EG7 cell lines do not present OVA-derived peptide, thus EG7 or EG7.hB7-H4 cells were pulsed with peptide and labeled with the succinimydal ester CF SE. EG7 cells that were antigen-negative (Ag−) were labeled with DDAO and were mixed at a 1:1 ratio with antigen-positive (Ag+) targets.

Following 4 hour incubation, cells were stained with a Live/Dead stain and viable target cells quantitated. CTL-mediated lysis is determined by a change in the ratio between CFSE (Ag+) and DDAO (Ag−) targets.

Results

Figure 25:
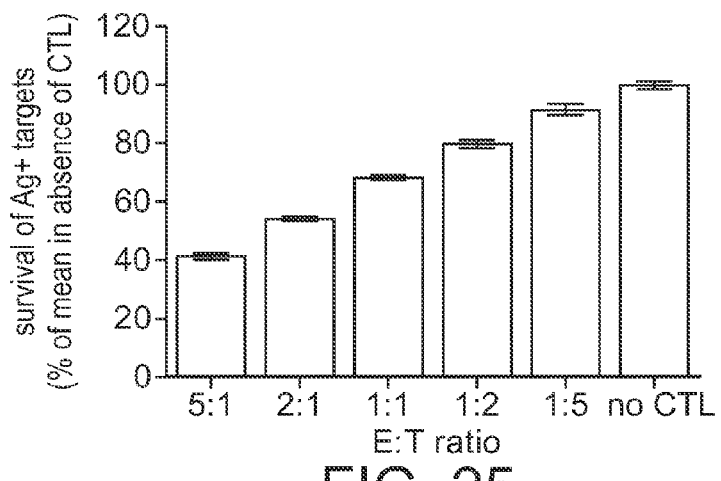
FIG. 25 is a bar graph showing the survival of Ag+ target cells (% of mean in absence of CTL) at different effector cell:target cell ratios in a CTL-mediated lysis assay.

The effect of different concentrations of chimeric 6H3 antibody on CTL-mediated lysis of B7-H4-expressing cells was investigated at different effector:target cell ratios. As shown in FIG. 25, the frequency of Ag+ targets relative to Ag− decreases as the E:T ratio is increased.

The specific lysis was determined by adjusting the survival by the starting ratio of Ag+ to Ag− targets. Human chimeric 6H3 antibody increased the specific lysis of EG7.B7-H4 cells at both concentrations tested (FIG. 26). Furthermore, chimeric 6H3 induced lysis of the B7-H4+ cells compared to control IgG in the absence of CTL (FIG. 26, last four bars).

Example 11

6H3 Reduces Tumor Volume and Increases Survival in a Lewis Lung Carcinoma Syngeneic Tumor Model Materials and Methods Lewis Lung Carcinoma (LLC) cells were inoculated to 27 B16 mice. Tumor bearing mice (150-250 mm$^3$) were selected, and divided into three groups (9 mice/group) on day 8. Mice were treated twice a week (total 5 doses) at 10 mg/kg with mouse 6H3.m1 (mouse IgG1) or 6H3.m2a (mouse IgG2a) mAbs, or with formulation buffer. Tumor size was monitored three times a week.

Results

An experiment was designed to evaluate the efficacy of anti-B7-H4 mAbs in a cancer model with or without potential for effector function. Lewis Lung Carcinoma (LLC) model was selected in part because B7-H4 expression has been observed in tumor and tumor associated macrophage in vivo in this model. Mice with established LLC cell tumors were treated with mouse 6H3.m1 (mouse IgG1) or 6H3.m2a (mouse IgG2a), and tumors were monitored over time.

On day 18, mice treated with formulation buffer were observed to have ulcerated LLC tumors, with the wound being almost as large as the tumor. Mice treated with 6H3.m1 appeared similar to the formulation buffer treated group. Mice treated with 6H3.2ma had smaller wounds that were starting to close. 6H3.m2a was observed to slow tumor growth and increase survival time (p=0.015) (FIGS. 27A and 27B). The results were confirmed in a second assay (FIGS. 28A and 28B).

Example 12

CT26.B7H4 Syngeneic Murine Tumor Model

Materials and Methods

Mice were inoculated with CT26-B7H4 (1E05) via tail vein injection on day 0, and treated with 10 mg/kg or 1 mg/kg of mouse 6H3.m1 (mouse IgG1) or 6H3.m2a (mouse IgG2a) beginning on Day 10 or Day 14. Mice were euthanized on Day 24, and the number and size of tumor nodules in the lung was recorded. Lungs from all experimental groups were removed and stored in fixing solution. The experimental design and schedule are shown below. There were 12-13 mice per group, two doses per week:
  Group 1, formulation buffer (12 mice)
  Group 2, 6H3.mIgG2a, 10 mg/kg on Day 10 (12 mice)
  Group 3, 6H3.mIgG2a, 1 mg/kg on Day 10 (12 mice)
  Group 4, 6H3.mIgG2a, 10 mg/kg on Day 14 (13 mice)
  Group 5, 6H3.mIgG2a, 1 mg/kg on Day 14 (13 mice)

Results

Figure 29A:
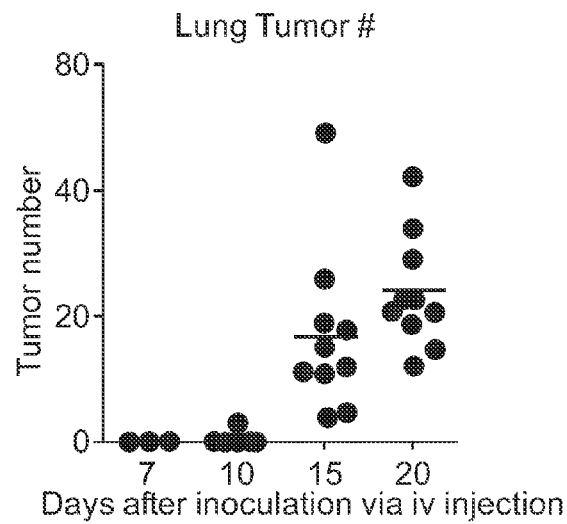
FIG. 29A is a dot plot showing the growth kinetics of tumors (tumor number) in a CT26.B7H4 lung cancer model over time (days) following intravenous inoculation of tumor cells in the absence of treatment.
Figure 29B:
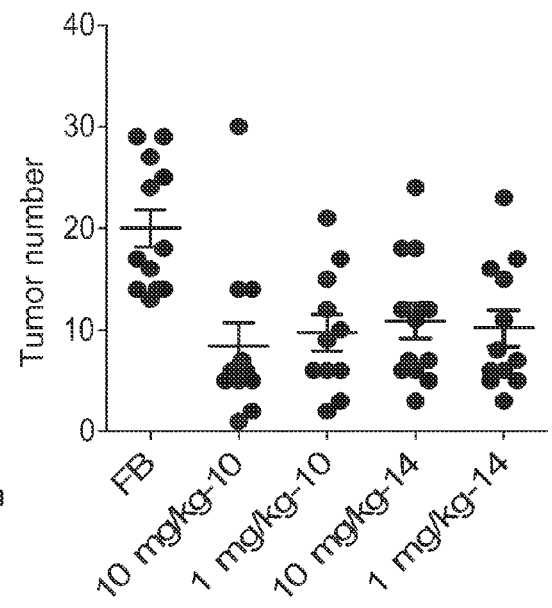
FIG. 29B is a dot plot showing tumor number in a CT26.B7H4 lung cancer model over time (days) following intravenous inoculation of tumor cells and treatment with formulation buffer (FB), 10 mg/kg 6H3.m2a beginning on day 10 (10 mg/kg-10); 1 mg/kg 6H3.m2a beginning on day 10 (1 mg/kg-10); 10 mg/kg 6H3.m2a beginning on day 14 (10 mg/kg-14); or 1 mg/kg 6H3.m2a beginning on day 14 (1 mg/kg-14).

The efficacy of 6H3 antibodies was tested in a CT26-B7H4 metastatic lung tumor model. The growth kinetics of tumors over time in the absence of treatment is illustrated in FIG. 29A. In the experimental assay, mice were inoculated with CT26-B7H4 (1E05) via tail vein injection on day 0, and treated with 10 mg/kg or 1 mg/kg of mouse 6H3.m1 (mouse IgG1) or 6H3.m2a (mouse IgG2a) beginning or days 10 or 14. In general, there were no significant changes in body weight, except for one mouse that had been given formulation buffer, losing 6% body weight and showing sickness on day 24. The number of metastatic tumor was significantly decreased with 6H3.mIgG2a treatment (p<0.001) (FIG. 29B).

Example 13

Evaluation of Toxicity

Materials and Methods

BALB/c mice, 7-9 weeks old, 8/group were treated with 6H3.mIgG1, 6H3.mIgG2a, or formulation buffer at a dosage of 100 mg/kg once a week for a month (5 doses). Blood glucose was tested after 4$^{th}$ dose.

Serum was collected for initial evaluation of PK (peak and trough post 4$^{th}$ dose). Antibody was captured from serum with a B7-H4-Ig fusion protein, and detected with biotin-anti-mouse IgG1 (6H3.mIgG1) or IgG2a (6H3.mIgG2a) and detected with Europium-Streptavidin.

Organs were collected for histopathology: heart, liver, spleen, lung, kidney (especially glomeruli), intestine (ileum, duodenum, jejunum, cecum, colon), uterus, salivary gland, gall bladder and pancreas (with special attention to islets).

Results

Figure 30:
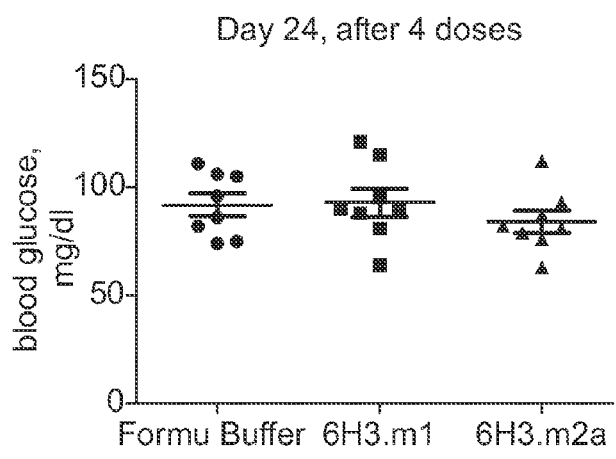
FIG. 30 is a dot plot showing the blood glucose (mg/dl) in mice on day 24, following four, once weekly doses of formulation buffer, or 100 mg/kg of 6H3.m1 or 6H3.m2.
Figure 31:
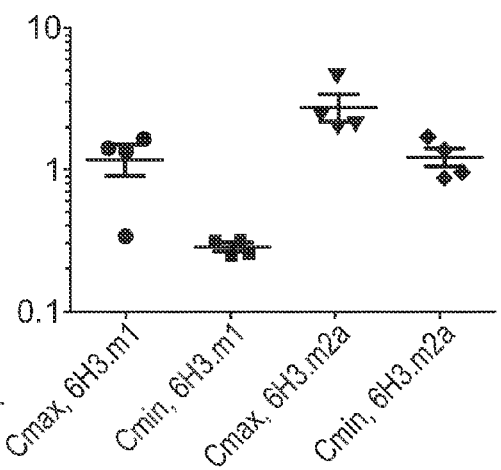
FIG. 31 is a dot plot showing the antibody level in the serum of mice (mg/ml) for peak (Cmax) and trough (Cmin) of 6H3.m1 or 6H3.m2 after the fourth of once weekly doses of 100 mg/kg of 6H3.m1 or 6H3.m2.
Figure 32A:
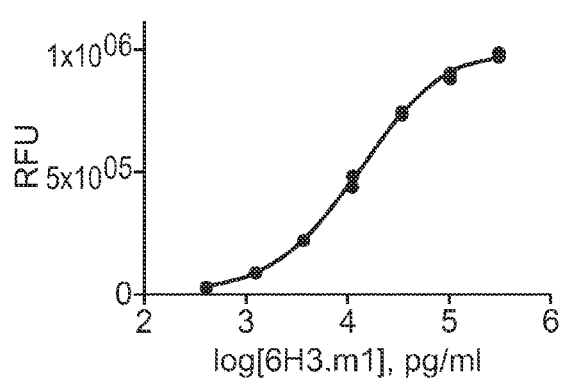
FIGS. 32A-32B are line graphs showing the relative fluorescent units (RFU) as a function of serum antibody concentration (log [antibody], µg/ml) for 6H3.m1 (32A) or 6H3.m2 (32B).
Figure 32B:
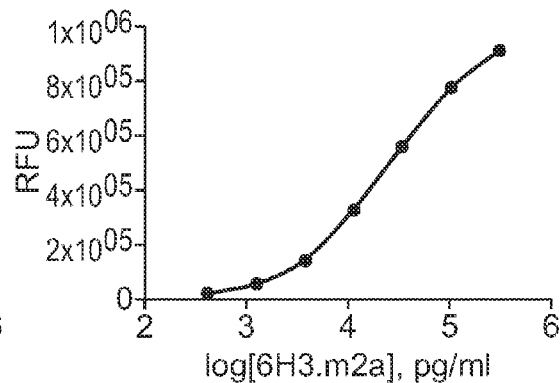

A toxicology study was conducted to provide a preliminary evaluation of the toxicity of anti-B7-H4 antibodies with vs. without the potential for immune effector function. All mice survived until scheduled sacrifice. Blood glucose levels were unaffected (FIG. 30). No test-article-related toxic effects were detected. Peak and trough antibody concentrations were evaluated following the 4th dose. High serum concentrations were confirmed, and modest differences were observed between Cmax and Cmin (FIGS. 31 and 32A-32B).

No test article-related microscopic findings were noted during histopathology analysis. The microscopic findings observed were considered incidental, of the nature commonly observed in this strain and age of mice, and/or were of similar incidence and severity in animals receiving formulation buffer and animals receiving 6H3.m1 and 6H3.m2a and, therefore, were considered unrelated to administration of 6H3.m1 and 6H3.m2a. No differences were noted in kidney glomeruli or pancreatic islets among the groups.

Some of the lung and many of the intestine sections showed evidence of autolysis. The few autolytic tissues that could not be evaluated and few tissues that were unavailable for evaluation were not considered to have impacted the assessment of microscopic changes related to administration of 6H3.m1 and 6H3.m2a.

Example 14

Binding Characterization of Humanized Variants of 6H3

Materials and Methods

100 µl 1 µg/ml B7-H4ECD his-tagged protein (Sinobiologics) diluted in PBS was immobilized on flat bottom 96 well plate (Costar 9017) overnight at 4° C. Plates were washed twice with PBS+0.1% PS-20 and blocked with 200 µl/well PBS 10% FBS at RT for 1 hr. 100 µl chimeric 6H3 and 14 selected 6H3 humanized variants diluted in PBS 10% FBS were added to each well and incubated at RT for 1 hr. Plates were washed three times and 100 µl 1 µg/ml anti-human Ig HRP (Sigma) was added to each well and incubated at RT for 1 hr. Plates were washed six times and 100 µl TMB substrate (SurModics) was added to each well for 5-15 mins 100 µl stop solution (0.1M Sulfuric acid) was added to each well. Plates were read at Absorbance 450 nm by PerkinElmer EnVision 2104 Multilabel Reader.

Results

An ELISA assay was designed to characterize the binding of humanized variant 6H3 antibodies to the B7-H4 extracellular domain relative to human chimeric 6H3.

Figure 33:
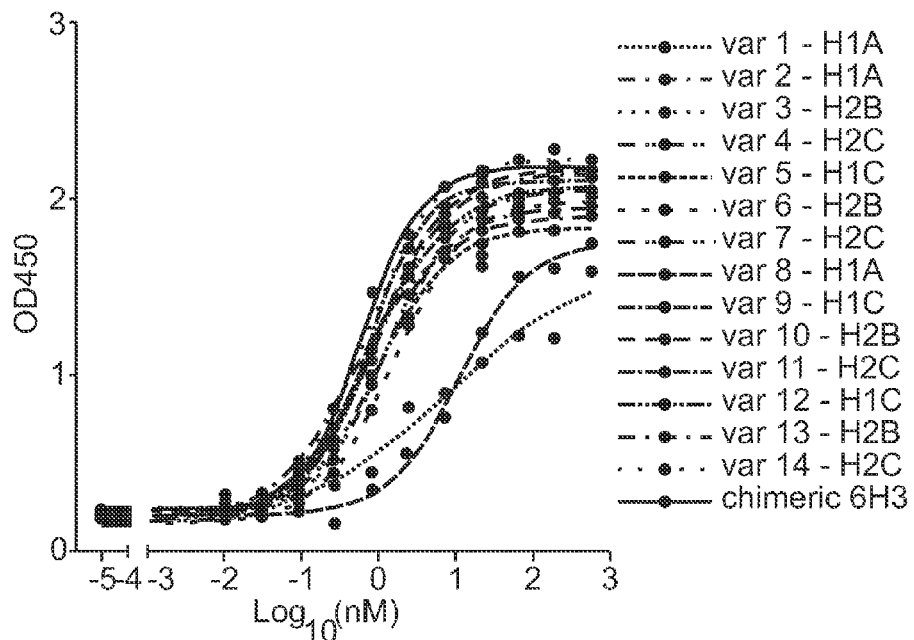
FIG. 33 is a binding curve showing the results of an ELISA assay (OD450 as a function of antibody concentration (Log 10 (nM)) measuring human chimeric 6H3 and fourteen humanized variant binding to the extracellular domain of B7-H4.

The results are presented in FIG. 33 and Table 8 and show that 14 tested humanized variants maintain plus or minus 2-fold affinity for human B7-H4 compared to human chimeric 6H3.

TABLE 8

EC50 of mAB 6H3 antibodies to B7-H4

| ANTIBODY | $EC_{50}$ (nM) |
|---|---|
| hc6H3 | 0.62 |
| V1 | 8.67 |
| V2 | 0.51 |
| V3 | 1.19 |
| V4 | 1.16 |
| V5 | 0.95 |
| V6 | 1.64 |
| V7 | 1.07 |
| V8 | 11.44 |
| V9 | 0.75 |
| V10 | 0.89 |
| V11 | 0.97 |
| V12 | 0.78 |
| V13 | 0.92 |
| V14 | 0.68 |

Example 15

Competition Binding Characterization of Humanized 6H3

Materials and Methods

A 12-point, 3-fold dilution series of 14 humanized 6H3 antibody variants was prepared ranging from 100 μg/ml to 0.5 ng/ml. Dilutions were prepared in assay diluent containing biotinylated mouse anti-human B7-H4 6H3 (SEQ ID NOS:3 and 5 for light chain variable region and heavy chain variable region respectively) at 5 ng/ml. Antibodies were allowed to bind to B7-H4-Ig-coated assay plates (200 ng/well) for 1 hour at room temperature and detected with streptavidin HRP.

B7-H4-Ig is a fusion protein having the sequence:

```
                                          (SEQ ID NO: 31)
GFGISGRHSI  TVTTVASAGN  IGEDGIQSCT  FEPDIKLSDI

VIQWLKEGVL  GLVHEFKEGK  DELSEQDEMF  RGRTAVFADQ

VIVGNASLRL  KNVQLTDAGT  YKCYIITSKG  KGNANLEYKT

GAFSMPEVNV  DYNASSETLR  CEAPRWFPQP  TVVWASQVDQ

GANFSEVSNT  SFELNSENVT  MKVVSVLYNV  TINNTYSCMI

ENDIAKATGD  IKVTESEIKR  RSEPKSCDKT  HTCPPCPAPE

LLGGPSVFLF  PPKPKDTLMI  SRTPEVTCVV  VDVSHEDPEV

KFNWYVDGVE  VHNAKTKPRE  EQYNSTYRVV  SVLTVLHQDW

LNGKEYKCKV  SNKALPAPIE  KTISKAKGQP  REPQVYTLPP

SRDELTKNQV  SLTCLVKGFY  PSDIAVEWES  NGQPENNYKT

TPPVLDSDGS  FFLYSKLTVD  KSRWQQGNVF  SCSVMHEALH

NHYTQKSLSL  SPGK.
```

Results

A competition ELISA assay was carried out on 14 humanized 6H3 antibody variants (V1-V14). An advantage of competition binding is that the mAbs under comparison are not labeled or detected directly, and so differences in labeling or binding to secondary antibody cannot impact relative affinity.

Figure 34A:
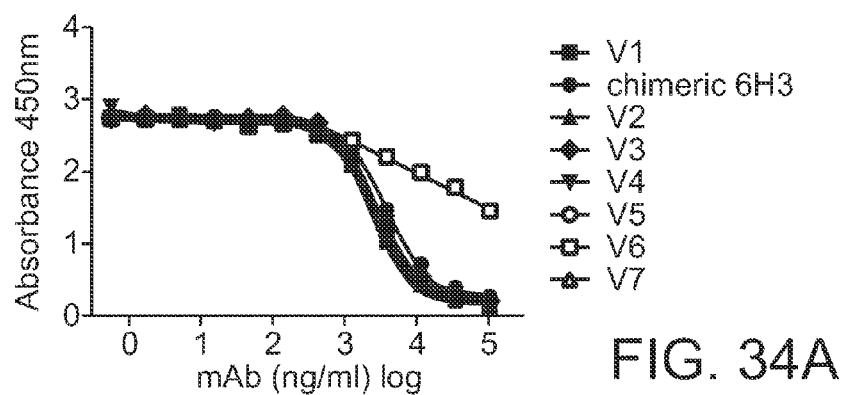
FIG. 34A-34B are binding curves showing the raw results of a competition ELISA assay (absorbance at 450 nm as a function of antibody concentration ((ng/ml) log)) measuring chimeric 6H3 and humanized variants V1-V7 (FIG. 34A) and V8-V14 (FIG. 34B) binding to B7-H4-Ig.
Figure 34B:
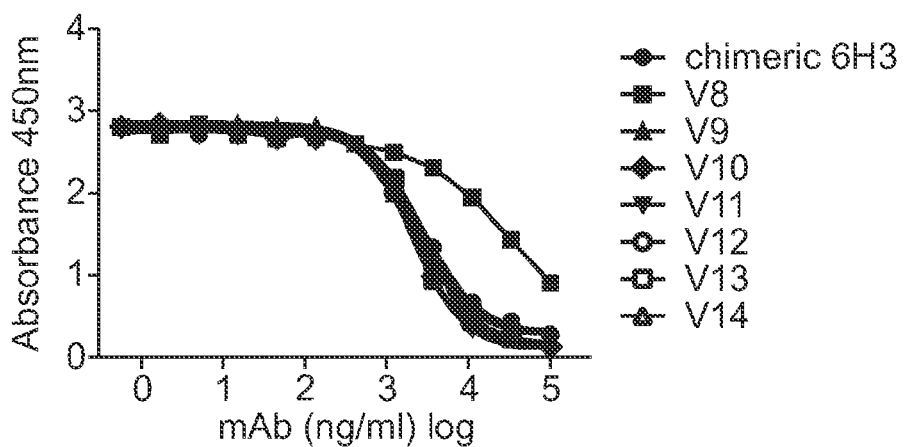

As shown in Table 9 and FIGS. 34A and 34B, variants V1 and V8 have markedly reduced binding affinities for B7-H4-Ig. All other variants have EC50 values within 1.5 fold of the human chimeric form of antibody 6H3. These findings are consistent with non-competitive results which also showed that Variants 1 and 8 exhibit poor binding affinity for B7-H4-Ig. All other variants are within 2-fold of chimeric 6H3.

TABLE 9

Binding Characteristics of Humanized Variant Antibodies V1-V14

| Plate 1 | | | Plate 2 | | |
|---|---|---|---|---|---|
| 6H3 variant | EC50 ng/mL | nM | 6H3 variant | EC50 ng/mL | nM |
| chimeric | 2437 | 16.2 | chimeric | 2259 | 15.1 |
| V1 | 23387 | 155.9 | V8 | 54719 | 364.8 |
| V2 | 2462 | 16.4 | V9 | 2687 | 17.9 |
| V3 | 3088 | 20.6 | V10 | 2126 | 14.2 |
| V4 | 2949 | 19.7 | V11 | 2199 | 14.7 |
| V5 | 3625 | 24.2 | V12 | 3005 | 20.0 |
| V6 | 2532 | 16.9 | V13 | 2112 | 14.1 |
| V7 | 2631 | 17.5 | V14 | 2491 | 16.6 |

Example 16

Saturation Binding Characterization of Humanized 6H3

Materials and Methods

A saturation binding experiment was carried out on 624mel/B7-H4 cells using the chimeric 6H3 mAb and humanized variants of 6H3. Briefly, 50,000 cells were pretreated with 0.1% azide on ice for 30 minutes to inhibit B7-H4 internalization then stained for 30 minutes with biotinylated anti-B7-H4 mAbs. The mAbs were diluted in a 12-point, 3-fold dilution series ranging from 200 μg/ml down to 1 ng/ml. Cell were stained with streptavidin PE for 10 minutes, washed, fixed and analyzed by flow cytometry.

Results

Figure 35A:
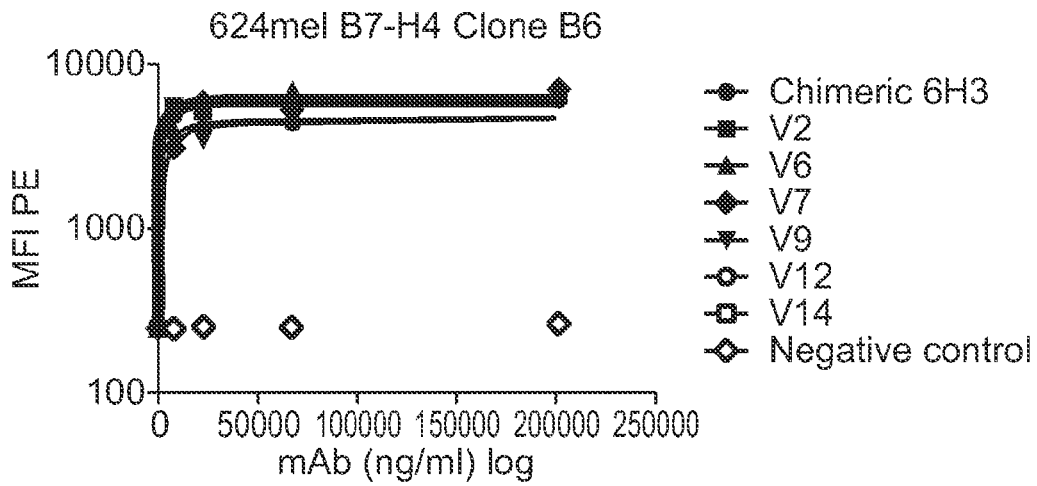
FIGS. 35A-35B are binding curves showing the raw (FIG. 35A) and background subtracted (FIG. 35B) results of a competition ELISA assay (absorbance at 450 nm as a function of antibody concentration ((ng/ml) log)) measuring chimeric 6H3, humanized variants V2, V6, V7, V9, V12, V14, and a negative control anti-PD-1 antibody (FIG. 34A only) binding to cells expressing B7-H4.
Figure 35B:
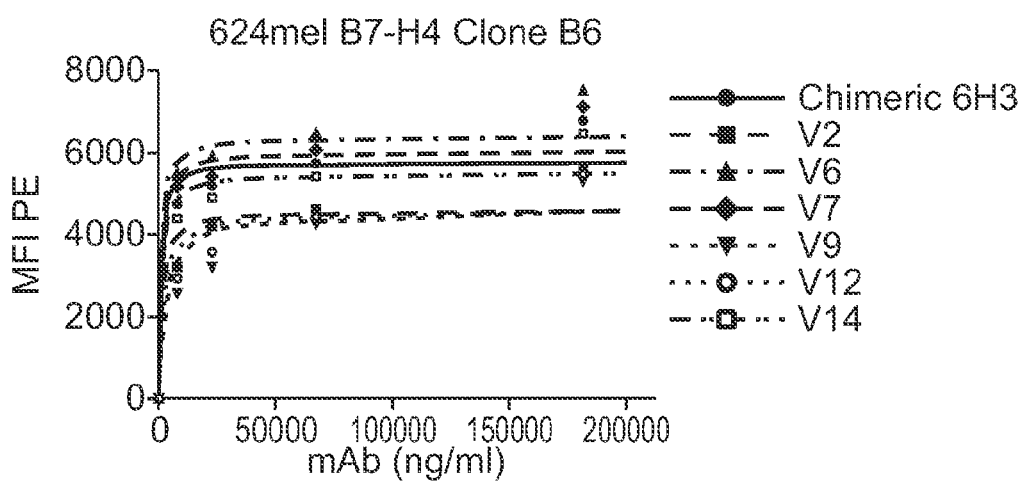

FIGS. 35A-35B are binding curves for the raw (FIG. 35A) and background subtracted data (FIG. 35B). The background subtracted data was generated by subtracting the average signal from an anti-PD-1 antibody (245 MFI) from all other points. The subtracted values were used to determine the Kd and Bmax. The antibodies appear to fall into two groups based on Kd values (Table 10).

TABLE 10

Anti-B7-H4 Antibody Binding Kinetics

| mAb | Kd | Std. Error | Bmax | Std. Error |
|---|---|---|---|---|
| AM P-841 | 578 | 145 | 5811 | 256 |
| 6H3 V2 | 1320 | 543 | 4649 | 365 |
| 6H3 V6 | 787 | 152 | 6420 | 225 |
| 6H3 V7 | 803 | 151 | 6080 | 208 |
| 6H3 V9 | 3306 | 1352 | 4612 | 402 |

TABLE 10-continued

Anti-B7-H4 Antibody Binding Kinetics

| mAb | Kd | Std. Error | Bmax | Std. Error |
|---|---|---|---|---|
| 6H3 V12 | 2177 | 837 | 4584 | 356 |
| 6H3 V14 | 920 | 193 | 5575 | 215 |

Example 17

Internalization Impacts Binding and Kd Estimation

Materials and Methods

For each staining, 0.2 million HEK293.hB7-H4 transfectants were resuspended in 100 µl flow cytometry buffer (PBS+2% FBS). A serial dilution of chimeric 6H3 and 14 humanized variants of 0, 0.1 ng, 0.3 ng, 1 ng, 3 ng, 10 ng, 30 ng, 100 ng, 300 ng, 1 µg, 3 µg and 10 µg were added to the cells and incubated at 4° C. for 30 min. Cells were then washed twice with 2 ml flow cytometry buffer, and resuspended in 100 µl flow cytometry buffer. 1 µl anti-hIg PE secondary antibody (Biolegend) was added and incubated with the cells for 15 mins Samples were then washed and resuspended in 100 µl flow cytometry buffer. Flow Cytometry data was acquired using BD Canto (BD Biosciences) in plate format and analyzed by FlowJo software. Staining data (MFI) was then input into Prism 5 software to generate binding curve. Curve-fit using one-site specific binding algorithm calculates individual $K_D$ for each variant.

Results

Figure 36:
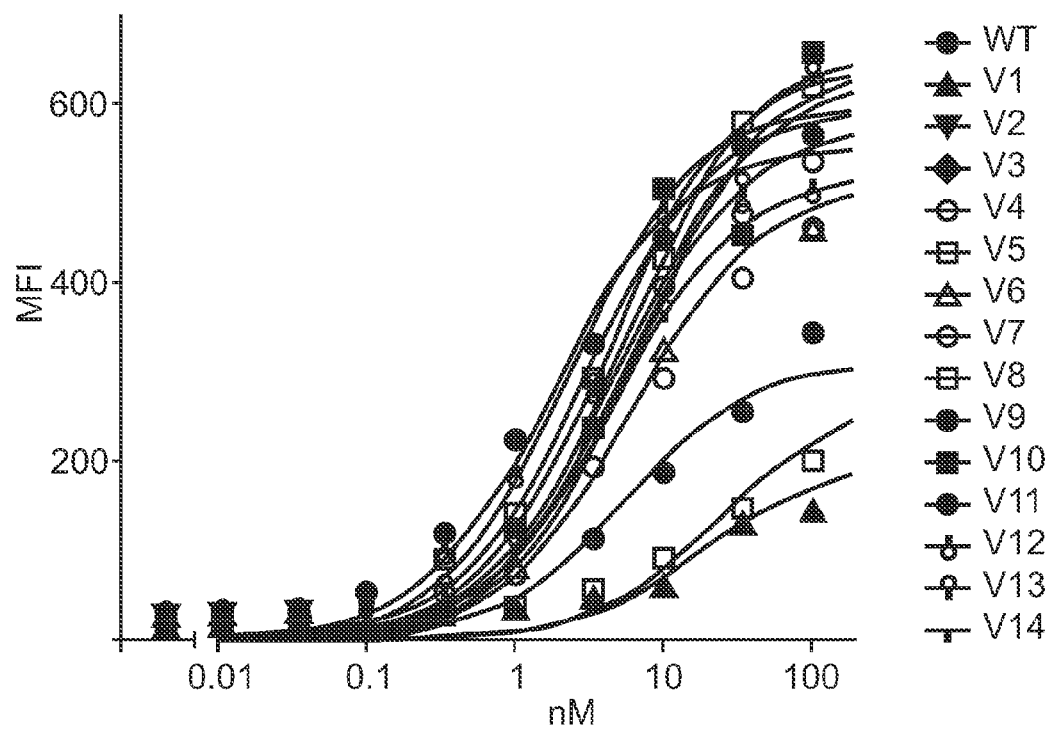
FIG. 36 is a binding curve showing antibody binding (mean fluorescent intensity (MFI) as a function of antibody concentration (nM)) of humanized variants of 6H3 binding to HEK293 transfectants expressing B7-H4.

An assay was designed to determine the kinetics of humanized variants of 6H3 binding to HEK293 transfectants cells expressing B7-H4. The results are presented in Table 11 below and FIG. 36. The results indicate that cell internalization of the antibodies has an impact on cell-binding and Kd estimation.

TABLE 11

Binding Kinetics of Humanized Variants of 6H3 to HEK293 Cells Expressing B7-H4

| ANTIBODY | $K_D$ (nM) | Bmax(MFI) |
|---|---|---|
| Chimeric 6H3 | 5.8 | 316 |
| V1 | 18.8 | 204 |
| V2 | 2.4 | 603 |
| V3 | 6.0 | 583 |
| V4 | 5.2 | 580 |
| V5 | 4.2 | 646 |
| V6 | 5.0 | 526 |
| V7 | 6.5 | 513 |
| V8 | 24.3 | 273 |
| V9 | 1.8 | 553 |
| V10 | 5.5 | 662 |
| V11 | 6.9 | 648 |
| V12 | 3.2 | 597 |
| V13 | 7.0 | 648 |
| V14 | 5.8 | 629 |

Example 18

6H3 Binds to Mouse B7-H4

Materials and Methods

100 µl 1 µg/ml mouse B7-H4ECD mIgG2a Fc fusion protein diluted in PBS was immobilized on flat bottom 96 well plate (Costar 9017) overnight at 4° C. Plates were washed twice with PBS+0.1% PS-20 and blocked with 200 µl/well PBS 10% FBS at RT for 1 hr. 100 µl chimeric 6H3 and 14 selected 6H3 humanized variants diluted in PBS 10% FBS were added to each well and incubated at RT for 1 hr. Plates were washed three times and 100 µl 1 µg/ml anti-human Ig HRP (Sigma) was added to each well and incubated at RT for 1 hr. Plates were washed six times and 100 µl TMB substrate (SurModics) was added to each well for 5-15 mins 100 µl stop solution (0.1M Sulfuric acid) was added to each well. Plates were read at Absorbance 450 nm by PerkinElmer EnVision 2104 Multilabel Reader.

Results

Figure 37:
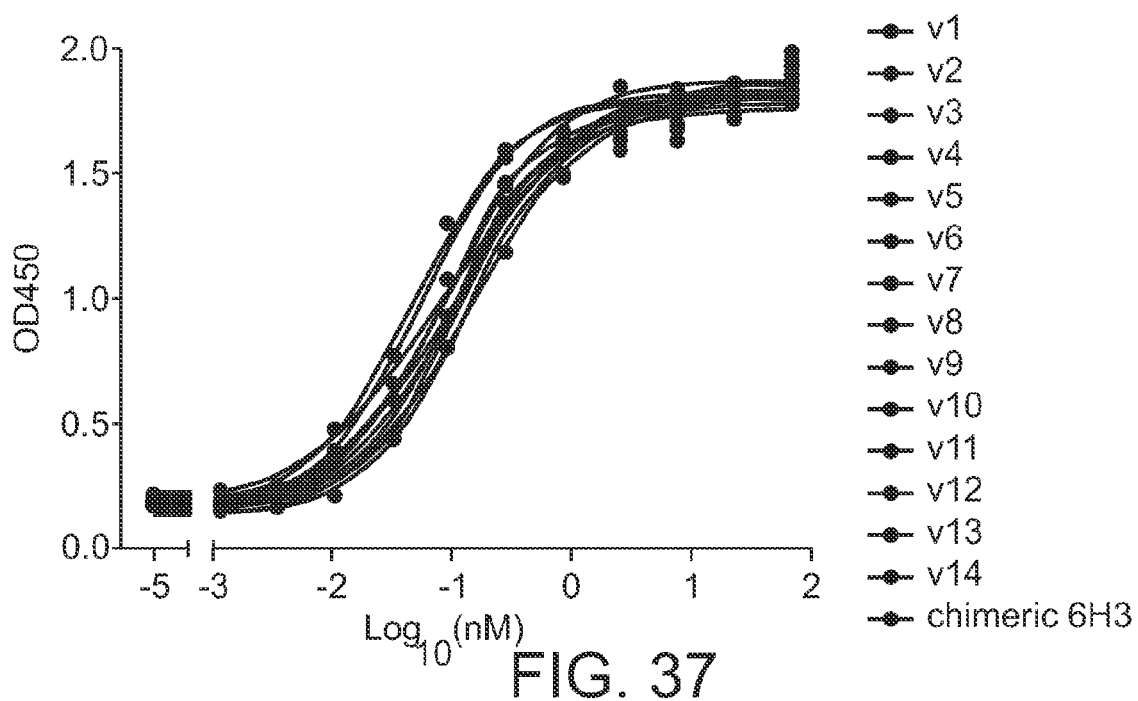
FIG. 37 is a binding curve showing the results of an ELISA assay (OD450 as a function of antibody concentration (log 10 (nM)) measuring antibody chimeric 6H3 and humanized variants of 6H3 binding to mouse B7-H4-mIg fusion protein.

An ELISA assay was designed to determine if humanized variants of 6H3 bind to mouse B7-H4 based on their ability to bind to a mouse B7-H4-mIg fusion protein. The results are presented in Table 12 below and FIG. 37. All 14 of the tested variants maintained plus or minus 2-fold affinity to mouse B7-H4 when compared to human chimeric 6H3 binding. These results indicate that functional analysis of human variants of 6H3 can be carried out using the murine model system, in which cells and/or animals express mouse B7-H4 protein.

TABLE 12

Binding Characteristics of Humanized Variants of 6H3 to Mouse B7-H4-mouse-Ig Fusion Protein

| ANTIBODY | $EC_{50}$ (nM) |
|---|---|
| Chimeric 6H3 | 0.09 |
| V1 | 0.10 |
| V2 | 0.08 |
| V3 | 0.10 |
| V4 | 0.08 |
| V5 | 0.05 |
| V6 | 0.13 |
| V7 | 0.11 |
| V8 | 0.06 |
| V9 | 0.07 |
| V10 | 0.13 |
| V11 | 0.11 |
| V12 | 0.09 |
| V13 | 0.13 |
| V14 | 0.11 |

Example 19

6H3 Reverses the Effects of B7-H4-Ig

Materials and Methods

Mouse lymph nodes (LN) were harvested from $PLP_{139-451}$ immunized SJL mice on day 8 post immunization. LN T cells were stimulated with 10 µg/mL of $PLP_{139-451}$ and 10 µg/mL of B7-H4 Ig (SEQ ID NO: 31) or control Ig plus various concentrations of humanized variants of 6H3 (10, 3.33, 1.11 & 0 µg/mL). [$^3$H]-thymidine was added into the culture for the last 48 hours of culture for T cell proliferation assessment. Conditioned culture media was analyzed for IL-17, IFN' and IL-10 production.

Results

An assay was designed to test the effect of humanized variants of 6H3 on treatment of cell with B7-H4-Ig. FIGS. 38A-38D show the results of the assay. Incubation of B7-H4-Ig treated cells with 6H3, or humanized variants 2, 6, 7, 11, 12, or 14 increase secretion of proinflammatory cytokines such as IL-17 (FIG. 38A) and IFNγ (FIG. 38B), increase cell proliferation ([3H]-thymidine incorporation) (FIG. 38C), and reduce secretion of anti-inflammatory cytokines such as IL-10 (FIG. 38D). These results indicate 6H3 and humanized variants reverse B7-H4-Ig mediated immune inhibitory responses.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. A molecule, comprising an antigen-binding fragment of a humanized variant of anti-human B7-H4 antibody 6H3, wherein said molecule immunospecifically binds to human B7-H4, and wherein said antigen-binding fragment comprises:
   (1) a light chain variable region of a humanized variant of anti-human B7-H4 antibody 6H3, wherein said light chain variable region has the amino acid sequence of any of SEQ ID NOS: 18-23; and
   (2) a heavy chain variable region of a humanized variant of anti-human B7-H4 antibody 6H3, wherein said heavy chain variable region has the amino acid sequence of any of SEQ ID NOS:24-29.

2. The molecule of claim 1, wherein said molecule immunospecifically binds to human B7-H4:
   (I) arrayed on the surface of a cell;
   (II) arrayed on the surface of a live cell at an endogenous concentration;
   (III) arrayed on the surface of a live cell, and modulates binding between B7-H4 and its cellular receptor;
   (IV) arrayed on the surface of a live cell, and inhibits immune suppression by tumor-associated macrophages;
   (V) arrayed on the surface of a live cell, and modulates an activity of a tumor-associated macrophage;
   (VI) arrayed on the surface of a live tumor cell and inhibits tumor-mediated suppression; or
   (VII) arrayed on the surface of a live tumor cell and causes tumor-specific cell lysis.

3. The molecule of claim 2, wherein said molecule is capable of being internalized into said cell and of mediating the death of said cell.

4. The molecule of claim 2, wherein said live cell is a tumor cell, a pathogen-infected cell or a macrophage.

5. The molecule of claim 1 wherein the molecule comprises
   (1) a light chain variable region of a humanized variant of anti-human B7-H4 antibody 6H3 comprising the amino acid sequence SEQ ID NO: 19 and a heavy chain variable region of a humanized variant of anti-human B7-H4 antibody 6H3 comprising the amino acid sequence SEQ ID NO:24;
   (2) a light chain variable region of a humanized variant of anti-human B7-H4 antibody 6H3 comprising the amino acid sequence SEQ ID NO: 19 and a heavy chain variable region of a humanized variant of anti-human B7-H4 antibody 6H3 comprising the amino acid sequence SEQ ID NO:26;
   (3) a light chain variable region of a humanized variant of anti-human B7-H4 antibody 6H3 comprising the amino acid sequence SEQ ID NO: 19 and a heavy chain variable region of a humanized variant of anti-human B7-H4 antibody 6H3 comprising the amino acid sequence SEQ ID NO:28;
   (4) a light chain variable region of a humanized variant of anti-human B7-H4 antibody 6H3 comprising the amino acid sequence SEQ ID NO: 19 and a heavy chain variable region of a humanized variant of anti-human B7-H4 antibody 6H3 comprising the amino acid sequence SEQ ID NO:29;
   (5) a light chain variable region of a humanized variant of anti-human B7-H4 antibody 6H3 comprising the amino acid sequence SEQ ID NO:20 and a heavy chain variable region of a humanized variant of anti-human B7-H4 antibody 6H3 comprising the amino acid sequence SEQ ID NO:26;
   (6) a light chain variable region of a humanized variant of anti-human B7-H4 antibody 6H3 comprising the amino acid sequence SEQ ID NO:20 and a heavy chain variable region of a humanized variant of anti-human B7-H4 antibody 6H3 comprising the amino acid sequence SEQ ID NO:28;
   (7) a light chain variable region of a humanized variant of anti-human B7-H4 antibody 6H3 comprising the amino acid sequence SEQ ID NO:20 and a heavy chain variable region of a humanized variant of anti-human B7-H4 antibody 6H3 comprising the amino acid sequence SEQ ID NO:29;
   (8) a light chain variable region of a humanized variant of anti-human B7-H4 antibody 6H3 comprising the amino acid sequence SEQ ID NO:22 and a heavy chain variable region of a humanized variant of anti-human B7-H4 antibody 6H3 comprising the amino acid sequence SEQ ID NO:24;
   (9) a light chain variable region of a humanized variant of anti-human B7-H4 antibody 6H3 comprising the amino acid sequence SEQ ID NO:22 and a heavy chain variable region of a humanized variant of anti-human B7-H4 antibody 6H3 comprising the amino acid sequence SEQ ID NO:26;
   (10) a light chain variable region of a humanized variant of anti-human B7-H4 antibody 6H3 comprising the amino acid sequence SEQ ID NO:22 and a heavy chain variable region of a humanized variant of anti-human B7-H4 antibody 6H3 comprising the amino acid sequence SEQ ID NO:28;
   (11) a light chain variable region of a humanized variant of anti-human B7-H4 antibody 6H3 comprising the amino acid sequence SEQ ID NO:22 and a heavy chain variable region of a humanized variant of anti-human B7-H4 antibody 6H3 comprising the amino acid sequence SEQ ID NO:29;
   (12) a light chain variable region of a humanized variant of anti-human B7-H4 antibody 6H3 comprising the amino acid sequence SEQ ID NO:23 and a heavy chain variable region of a humanized variant of anti-human B7-H4 antibody 6H3 comprising the amino acid sequence SEQ ID NO:26;
   (13) a light chain variable region of a humanized variant of anti-human B7-H4 antibody 6H3 comprising the amino acid sequence SEQ ID NO:23 and a heavy chain variable region of a humanized variant of anti-human B7-H4 antibody 6H3 comprising the amino acid sequence SEQ ID NO:28; or
   (14) a light chain variable region of a humanized variant of anti-human B7-H4 antibody 6H3 comprising the amino acid sequence SEQ ID NO:23 and a heavy chain variable region of a humanized variant of anti-human B7-H4 antibody 6H3 comprising the amino acid sequence SEQ ID NO:29.

6. The molecule of claim 1, wherein said molecule is detectably labeled or comprises a conjugated toxin, drug, receptor, enzyme, receptor ligand.

7. The molecule of claim 1, wherein said molecule is an antibody, and wherein said antibody is:
   (I) a monoclonal antibody, a chimeric antibody or a humanized antibody; or
   (II) a bispecific, trispecific or multispecific antibody.

8. The molecule of claim 1, wherein said molecule is an IgG1 or IgG4 antibody.

9. The molecule of claim 1, wherein said molecule has ADCC activity and is capable of direct tumor or TAM killing activity and/or inhibiting TAM- or tumor mediated-suppression.

10. The molecule of claim 1, wherein said molecule is a bispecific, trispecific or multispecific antibody that is capable of binding B7-H4 and a different molecule on the same cell.

11. A pharmaceutical composition for the treatment of cancer or infectious disease, comprising a therapeutically effective or prophylactically effective amount of the molecule of claim 1, and a physiologically acceptable carrier or excipient, wherein said molecule antagonizes a B7-H4-mediated suppression to up-modulate an immune response.

12. The pharmaceutical composition of claim 11 wherein said composition for the treatment of a chronic viral disease and said use is the treatment of said chronic viral disease.

13. A method for enhancing or inducing an immune response in a subject in need thereof comprising: administering an effective amount of the pharmaceutical composition according to claim 11.

14. A molecule, comprising an antigen-binding fragment of a mouse anti-human B7-H4 antibody 6H3, wherein said molecule immunospecificaily binds to human B7-H4, and wherein said antigen-binding fragment comprises:
(1) a light chain variable region of a mouse of anti-human B7-H4 antibody 6H3, wherein said light chain variable region has the amino acid sequence of SEQ ID NOS:3; and
(2) a heavy chain variable region of a mouse of anti-human B7-H4 antibody 6H3, wherein said heavy chain variable region has the amino acid sequence of SEQ ID NOS:5.

15. The molecule of claim 14, wherein said molecule is a bispecific, trispecific or multispecific antibody that is capable of binding B7-H4 and a different molecule on the same cell.

* * * * *

UNITED STATES PATENT AND TRADEMARK OFFICE
CERTIFICATE OF CORRECTION

PATENT NO. : 9,574,000 B2
APPLICATION NO. : 14/654074
DATED : February 21, 2017
INVENTOR(S) : Solomon Langermann et al.

Page 1 of 1

It is certified that error appears in the above-identified patent and that said Letters Patent is hereby corrected as shown below:

In the Specification

Column 1 Line 14 insert the following paragraph:
-- STATEMENT OF GOVERNMENTAL INTEREST
This invention was made with government support under grant number CA097085, awarded by the National Institutes of Health. The government has certain rights in the invention. --

Signed and Sealed this
Sixth Day of February, 2018

Joseph Matal
*Performing the Functions and Duties of the*
*Under Secretary of Commerce for Intellectual Property and*
*Director of the United States Patent and Trademark Office*

```
                            SEQUENCE LISTING

<160> NUMBER OF SEQ ID NOS: 31

<210> SEQ ID NO 1
    <211> LENGTH: 282
    <212> TYPE: PRT
    <213> ORGANISM: Homo sapiens

<400> SEQUENCE: 1

Met Ala Ser Leu Gly Gln Ile Leu Phe Trp Ser Ile Ile Ser Ile Ile
    1               5                   10                  15

Ile Ile Leu Ala Gly Ala Ile Ala Leu Ile Ile Gly Phe Gly Ile Ser
                20                  25                  30

Gly Lys His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
    65                  70                  75                  80

His Glu Phe Lys Glu Gly Lys Asp Glu Leu Ser Glu Gln Asp Glu Met
                    85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
        130                 135                 140

Tyr Lys Thr Gly Ala Phe Ser Met Pro Glu Val Asn Val Asp Tyr Asn
    145                 150                 155                 160

Ala Ser Ser Glu Thr Leu Arg Cys Glu Ala Pro Arg Trp Phe Pro Gln
                    165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
    225                 230                 235                 240

Thr Glu Ser Glu Ile Lys Arg Arg Ser His Leu Gln Leu Leu Asn Ser
                    245                 250                 255

Lys Ala Ser Leu Cys Val Ser Ser Phe Phe Ala Ile Ser Trp Ala Leu
                260                 265                 270

Leu Pro Leu Ser Pro Tyr Leu Met Leu Lys
                275                 280

<210> SEQ ID NO 2
    <211> LENGTH: 283
```

```
<212> TYPE: PRT
<213> ORGANISM: Homo sapiens

<400> SEQUENCE: 2

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ala Phe Val Ala Gly Trp Ala
            260                 265                 270

Leu Leu Ser Leu Ser Cys Cys Leu Met Leu Arg
        275                 280

<210> SEQ ID NO 3
<211> LENGTH: 112
<212> TYPE: PRT
<213> ORGANISM: Artificial Sequence
<220> FEATURE:
<223> OTHER INFORMATION: Peptide

<400> SEQUENCE: 3

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ile
            20                  25                  30

Asn Gly Asn Thr Tyr Leu His Trp Tyr Leu Gln Lys Pro Gly Gln Ser
        35                  40                  45

Pro Lys Val Leu Ile Tyr Lys Val Ser Asn Arg Phe Ser Gly Val Pro
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 4
<211> LENGTH: 337
<212> TYPE: DNA
<213> ORGANISM: Homo sapiens

<400> SEQUENCE: 4
gatgttgtga tgacccaaac tcctctctcc ctgcctgtca gtcttggaga tcaagcctcc    60
atctcttgca gatctagtca gagccttgta cacattaatg aaacaccta tttacattgg    120 tacctgcaga agccaggcca gtctccaaag gtcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
ctcacgttcg gtgctgggac caagctggag ctgaaac                              337

<210> SEQ ID NO 5
<211> LENGTH: 115
<212> TYPE: PRT
<213> ORGANISM: Artificial Sequence
<220> FEATURE:
<223> OTHER INFORMATION: Peptide

<400> SEQUENCE: 5

Glu Val Gln Leu Gln Gln Ser Gly Pro Val Leu Val Lys Pro Gly Thr
1               5                   10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Val Ile Asn Pro Tyr Asn Gly Asp Thr Thr Tyr Asn Gln Lys Phe
        50                  55                  60

Lys Gly Lys Ala Thr Leu Thr Val Asp Lys Ser Ser Thr Ala Tyr
65                  70                  75                  80

Met Glu Val Asn Ser Leu Thr Phe Glu Asp Ser Ala Val Tyr Tyr Cys
                85                  90                  95

Ala Arg Tyr Pro Glu Ser Thr Tyr Trp Gly Gln Gly Thr Leu Val Thr
            100                 105                 110

Val Ser Ala
        115

<210> SEQ ID NO 6
<211> LENGTH: 345
<212> TYPE: DNA
<213> ORGANISM: Homo sapiens

<400> SEQUENCE: 6
gaggtccagc tgcaacagtc tggacctgta ctggtgaagc ctgggacttc agtgaagatg    60
tcctgtaagg cttctggata cacattcact gactactata tgaactgggt gaagcagagc    120
catggaaaga gtcttgagtg gattggagtt attaatcctt acaacggtga cactacctac    180

```
aaccagaagt tcaagggcaa ggccacattg actgttgaca gtcctccag cacagcctac    240 atggaggtca acagcctgac atttgaggac tctgcagtct attactgtgc aagatacccg    300
gagagtactt actggggcca agggactctg gtcactgtct ctgca                    345
```

<210> SEQ ID NO 7
<211> LENGTH: 8
<212> TYPE: PRT
<213> ORGANISM: Artificial Sequence
<220> FEATURE:
<223> OTHER INFORMATION: Peptide

<400> SEQUENCE: 7

```
Lys Arg Arg Ser Lys Gln Gln Ser
1               5
```

<210> SEQ ID NO 8
<211> LENGTH: 110
<212> TYPE: PRT
<213> ORGANISM: Artificial Sequence
<220> FEATURE:
<223> OTHER INFORMATION: Peptide

<400> SEQUENCE: 8

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Ile Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Phe Cys Gln Gln Ser Asp
                85                  90                  95

Glu Gly Arg Thr Phe Gly Gly Gly Thr Lys Leu Glu Ile Lys
            100                 105                 110
```

<210> SEQ ID NO 9
<211> LENGTH: 118
<212> TYPE: PRT
<213> ORGANISM: Artificial Sequence
<220> FEATURE:
<223> OTHER INFORMATION: Peptide

<400> SEQUENCE: 9

```
Glu Val Gln Leu Val Glu Ser Gly Gly Asn Leu Val Lys Pro Gly Gly
1               5                   10                  15

Ser Leu Lys Leu Ser Cys Ala Ala Ser Gly Phe Thr Phe Ser Asn Ser
            20                  25                  30

Ala Met Ser Trp Val Arg Gln Thr Pro Glu Lys Arg Leu Glu Trp Val
        35                  40                  45

Ala Thr Ile Ser Asp Gly Gly Arg Tyr Thr Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Leu Tyr Tyr Cys
                85                  90                  95

Ala Arg Asp Arg Pro His Trp Tyr Phe Asp Val Trp Gly Thr Gly Ala
```

```
Thr Val Thr Val Ser Ser
        115

<210> SEQ ID NO 10
<211> LENGTH: 112
<212> TYPE: PRT
<213> ORGANISM: Artificial Sequence
<220> FEATURE:
<223> OTHER INFORMATION: Peptide

<400> SEQUENCE: 10

Asp Val Val Met Thr Gln Thr Pro Leu Ser Leu Pro Val Ser Leu Gly
1               5                   10                  15

Asp Gln Ala Ser Ile Ser Cys Arg Ser Ser His Ser Leu Val His Ser
            20                  25                  30

Asn Gly Asn Thr Tyr Leu His Trp Tyr Leu Gln Lys Pro Gly Gln Ser
        35                  40                  45

Pro Asn Leu Leu Ile Tyr Ile Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ala Gly Thr Lys Leu Glu Leu Lys
            100                 105                 110

<210> SEQ ID NO 11
<211> LENGTH: 116
<212> TYPE: PRT
<213> ORGANISM: Artificial Sequence
<220> FEATURE:
<223> OTHER INFORMATION: Peptide

<400> SEQUENCE: 11

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn Ser His
            20                  25                  30

Gly Met Ser Trp Val Arg Gln Thr Pro Glu Lys Arg Leu Asp Trp Val
        35                  40                  45

Ala Thr Ile Ser Asp Gly Gly Thr Tyr Thr Tyr Tyr Pro Val Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Asp Gly Gly Gly Gly Ala Tyr Trp Gly Gln Gly Thr Leu Val
            100                 105                 110

Thr Val Ser Ala
        115

<210> SEQ ID NO 12
<211> LENGTH: 113
<212> TYPE: PRT
<213> ORGANISM: Artificial Sequence
<220> FEATURE:
<223> OTHER INFORMATION: Peptide

<400> SEQUENCE: 12
```

-continued

```
Asp Ile Val Met Ser Gln Ser Pro Ser Ser Leu Ala Val Ser Val Gly
1               5                   10                  15

Glu Lys Val Thr Val Ser Cys Lys Ser Ser Gln Ser Leu Leu Tyr Ser
                20                  25                  30

Thr Asn Gln Arg Thr Tyr Leu Ala Trp Phe Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Thr Gly Thr Lys Leu Glu Leu
            100                 105                 110

Lys
```

<210> SEQ ID NO 13
<211> LENGTH: 115
<212> TYPE: PRT
<213> ORGANISM: Artificial Sequence
<220> FEATURE:
<223> OTHER INFORMATION: Peptide

<400> SEQUENCE: 13

```
Glu Val Lys Leu Val Glu Ser Gly Gly Leu Val Gln Pro Gly Ser
1               5                   10                  15

Ser Met Lys Leu Ser Cys Thr Ala Ser Gly Phe Lys Phe Thr Asp Tyr
                20                  25                  30

Tyr Met Ala Trp Val Arg Gln Val Pro Glu Lys Gly Leu Glu Trp Val
            35                  40                  45

Ala Asn Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Asn Ser Leu Lys Ser Glu Asp Thr Ala Thr Tyr Tyr Cys
                85                  90                  95

Ala Arg Lys Gly Tyr Phe Asp Tyr Trp Gly Gln Gly Thr Thr Leu Thr
            100                 105                 110

Val Ser Ser
        115
```

<210> SEQ ID NO 14
<211> LENGTH: 40
<212> TYPE: PRT
<213> ORGANISM: Homo sapiens

<400> SEQUENCE: 14

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Asn Trp
            35                  40
```

<210> SEQ ID NO 15
<211> LENGTH: 40
<212> TYPE: PRT

```
<213> ORGANISM: Homo sapiens

<400> SEQUENCE: 15

Asp Ile Val Met Thr Gln Thr Pro Leu Ser Leu Pro Val Thr Leu Gly
1               5                   10                  15

Gln Pro Ala Ser Ile Ser Cys Arg Ser Ser Arg Gly Leu Val His Ser
            20                  25                  30

Asp Gly Asn Thr Tyr Leu Asn Trp
        35                  40

<210> SEQ ID NO 16
<211> LENGTH: 40
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala
        35                  40

<210> SEQ ID NO 17
<211> LENGTH: 40
<212> TYPE: PRT
<213> ORGANISM: Homo sapiens

<400> SEQUENCE: 17

Pro Gly Gln Ser Leu Glu Trp Met Gly Trp Ile Asn Pro Gly Asp Gly
1               5                   10                  15

Asp Thr Lys Tyr Ser Gln Lys Phe Gln Gly Arg Val Thr Val Ala Arg
            20                  25                  30

Asp Thr Ser Ala Thr Thr Ala Tyr
        35                  40

<210> SEQ ID NO 18
<211> LENGTH: 112
<212> TYPE: PRT
<213> ORGANISM: Artificial Sequence
<220> FEATURE:
<223> OTHER INFORMATION: Antibody

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ile
            20                  25                  30

Asn Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gly Gly Thr Lys Val Glu Ile Lys
            100                 105                 110
```

-continued

<210> SEQ ID NO 19
<211> LENGTH: 112
<212> TYPE: PRT
<213> ORGANISM: Artificial Sequence
<220> FEATURE:
<223> OTHER INFORMATION: Antibody

<400> SEQUENCE: 19

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ile
            20                  25                  30

Asn Gly Asn Thr Tyr Leu His Trp Tyr Gln Gln Arg Pro Gly Gln Ser
        35                  40                  45

Pro Arg Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gly Gly Thr Lys Val Glu Ile Lys
            100                 105                 110
```

<210> SEQ ID NO 20
<211> LENGTH: 112
<212> TYPE: PRT
<213> ORGANISM: Artificial Sequence
<220> FEATURE:
<223> OTHER INFORMATION: Antibody

<400> SEQUENCE: 20

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ile
            20                  25                  30

Asn Gly Asn Thr Tyr Leu His Trp Tyr Leu Gln Arg Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gly Gly Thr Lys Val Glu Ile Lys
            100                 105                 110
```

<210> SEQ ID NO 21
<211> LENGTH: 112
<212> TYPE: PRT
<213> ORGANISM: Artificial Sequence
<220> FEATURE:
<223> OTHER INFORMATION: Antibody

<400> SEQUENCE: 21

```
Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val His Ile
            20                  25                  30

Asn Gly Asn Thr Tyr Leu Asn Trp Phe Gln Gln Arg Pro Gly Gln Ser
        35                  40                  45
```

Pro Arg Arg Leu Ile Tyr Lys Val Ser Asn Arg Asp Ser Gly Val Pro
        50                  55                  60

Asp Arg Phe Ser Gly Ser Gly Ser Gly Ala Asp Phe Thr Leu Lys Ile
 65                  70                  75                  80

Ser Arg Val Glu Ala Glu Asp Val Gly Val Tyr Tyr Cys Ser Gln Ser
                     85                  90                  95

Thr His Val Pro Leu Thr Phe Gly Gln Gly Thr Lys Val Glu Ile Lys
                100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Antibody

<400> SEQUENCE: 22

Asp Ile Val Met Thr Gln Thr Pro Leu Ser Leu Pro Val Thr Leu Gly
 1               5                  10                  15

Gln Pro Ala Ser Ile Ser Cys Arg Ser Ser Gln Ser Leu Val His Ile
                20                  25                  30

Asn Gly Asn Thr Tyr Leu His Trp Tyr Gln Gln Arg Pro Gly Gln Ser
            35                  40                  45

Pro Arg Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                     85                  90                  95

Thr His Val Pro Leu Thr Phe Gly Gln Gly Thr Lys Val Glu Ile Lys
                100                 105                 110

<210> SEQ ID NO 23
<211> LENGTH: 112
<212> TYPE: PRT
<213> ORGANISM: Artificial Sequence
<220> FEATURE:
<223> OTHER INFORMATION: Antibody

<400> SEQUENCE: 23

Asp Ile Val Met Thr Gln Thr Pro Leu Ser Leu Pro Val Thr Leu Gly
 1               5                  10                  15

Gln Pro Ala Ser Ile Ser Cys Arg Ser Ser Gln Ser Leu Val His Ile
                20                  25                  30

Asn Gly Asn Thr Tyr Leu His Trp Tyr Leu Gln Arg Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                     85                  90                  95

Thr His Val Pro Leu Thr Phe Gly Ala Gly Thr Lys Val Glu Ile Lys
                100                 105                 110

<210> SEQ ID NO 24
<211> LENGTH: 115
<212> TYPE: PRT

<213> ORGANISM: Artificial Sequence
<220> FEATURE:
<223> OTHER INFORMATION: Antibody

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Ile Ile Asn Pro Tyr Asn Gly Asp Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Pro Glu Ser Thr Tyr Trp Gly Gln Gly Thr Leu Val Thr
            100                 105                 110

Val Ser Ser
        115

<210> SEQ ID NO 25
<211> LENGTH: 115
<212> TYPE: PRT
<213> ORGANISM: Artificial Sequence
<220> FEATURE:
<223> OTHER INFORMATION: Antibody

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Ile Ile Asn Pro Tyr Asn Gly Asp Thr Ser Tyr Asn Gln Lys Phe
    50                  55                  60

Gln Gly Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Pro Glu Ser Thr Tyr Trp Gly Gln Gly Thr Leu Val Thr
            100                 105                 110

Val Ser Ser
        115

<210> SEQ ID NO 26
<211> LENGTH: 115
<212> TYPE: PRT
<213> ORGANISM: Artificial Sequence
<220> FEATURE:
<223> OTHER INFORMATION: Antibody

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

```
Tyr Met Asn Trp Val Arg Gln Ala Pro Gly Gln Gly Leu Glu Trp Ile
            35                  40                  45

Gly Ile Ile Asn Pro Tyr Asn Gly Asp Thr Ser Tyr Asn Gln Lys Phe
        50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Pro Glu Ser Thr Tyr Trp Gly Gln Gly Thr Leu Val Thr
            100                 105                 110

Val Ser Ser
        115

<210> SEQ ID NO 27
<211> LENGTH: 115
<212> TYPE: PRT
<213> ORGANISM: Artificial Sequence
<220> FEATURE:
<223> OTHER INFORMATION: Antibody

<400> SEQUENCE: 27

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Ser Leu Glu Trp Met
            35                  40                  45

Gly Trp Ile Asn Pro Tyr Asn Gly Asp Thr Lys Tyr Ser Gln Lys Phe
        50                  55                  60

Gln Gly Arg Val Thr Val Ala Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Pro Glu Ser Thr Tyr Trp Gly Gln Gly Thr Leu Val Thr
            100                 105                 110

Val Ser Ser
        115

<210> SEQ ID NO 28
<211> LENGTH: 115
<212> TYPE: PRT
<213> ORGANISM: Artificial Sequence
<220> FEATURE:
<223> OTHER INFORMATION: Antibody

<400> SEQUENCE: 28

Glu Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Ser Leu Glu Trp Met
            35                  40                  45

Gly Val Ile Asn Pro Tyr Asn Gly Asp Thr Thr Tyr Asn Gln Lys Phe
        50                  55                  60

Gln Gly Arg Val Thr Val Ala Val Asp Lys Ser Ala Thr Thr Ala Tyr
65                  70                  75                  80

Met Glu Leu Ser Ser Leu Arg Ser Glu Asp Thr Ala Val Tyr Tyr Cys
```

```
                85                  90                  95
Ala Arg Tyr Pro Glu Ser Thr Tyr Trp Gly Gln Gly Thr Leu Val Thr
            100                 105                 110

Val Ser Ser
        115

<210> SEQ ID NO 29
<211> LENGTH: 115
<212> TYPE: PRT
<213> ORGANISM: Artificial Sequence
<220> FEATURE:
<223> OTHER INFORMATION: Antibody

<400> SEQUENCE: 29

Glu Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Ser Leu Glu Trp Ile
        35                  40                  45

Gly Val Ile Asn Pro Tyr Asn Gly Asp Thr Thr Tyr Asn Gln Lys Phe
50                  55                  60

Gln Gly Arg Val Thr Val Thr Val Asp Lys Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Pro Glu Ser Thr Tyr Trp Gly Gln Gly Thr Leu Val Thr
            100                 105                 110

Val Ser Ser
        115

<210> SEQ ID NO 30
<211> LENGTH: 8
<212> TYPE: PRT
<213> ORGANISM: Artificial Sequence
<220> FEATURE:
<223> OTHER INFORMATION: Peptide

<400> SEQUENCE: 30

Ser Ile Ile Asn Phe Glu Lys Leu
1               5

<210> SEQ ID NO 31
<211> LENGTH: 454
<212> TYPE: PRT
<213> ORGANISM: Artificial Sequence
<220> FEATURE:
<223> OTHER INFORMATION: Fusion Protein

<400> SEQUENCE: 31

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Lys Asp Glu Leu Ser
50                  55                  60

Glu Gln Asp Glu Met Phe Arg Gly Arg Thr Ala Val Phe Ala Asp Gln
65                  70                  75                  80
```

```
Val Ile Val Gly Asn Ala Ser Leu Arg Leu Lys Asn Val Gln Leu Thr
                 85                  90                  95
Asp Ala Gly Thr Tyr Lys Cys Tyr Ile Ile Thr Ser Lys Gly Lys Gly
            100                 105                 110
Asn Ala Asn Leu Glu Tyr Lys Thr Gly Ala Phe Ser Met Pro Glu Val
            115                 120                 125
Asn Val Asp Tyr Asn Ala Ser Ser Glu Thr Leu Arg Cys Glu Ala Pro
130                 135                 140
Arg Trp Phe Pro Gln Pro Thr Val Val Trp Ala Ser Gln Val Asp Gln
145                 150                 155                 160
Gly Ala Asn Phe Ser Glu Val Ser Asn Thr Ser Phe Glu Leu Asn Ser
                165                 170                 175
Glu Asn Val Thr Met Lys Val Val Ser Val Leu Tyr Asn Val Thr Ile
            180                 185                 190
Asn Asn Thr Tyr Ser Cys Met Ile Glu Asn Asp Ile Ala Lys Ala Thr
            195                 200                 205
Gly Asp Ile Lys Val Thr Glu Ser Glu Ile Lys Arg Arg Ser Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
            290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
            355                 360                 365
Gln Val Ser Leu Thr Cys Leu Val Lys Gly Phe Tyr Pro Ser Asp Ile
            370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro Gly Lys
450
```